United States Patent
Marcotrigiano et al.

(10) Patent No.: US 9,758,794 B2
(45) Date of Patent: Sep. 12, 2017

(54) HCV E2 CONSTRUCT COMPOSITIONS AND METHODS

(71) Applicants: Rutgers, The State University of New Jersey, New Brunswick, NJ (US); Emory University, Atlanta, GA (US)

(72) Inventors: Joseph Marcotrigiano, New Brunswick, NJ (US); Jillian L. Whidby, Pilesgrove, NJ (US); Arash Grakoui, Dectaur, GA (US)

(73) Assignees: Rutgers, The State University of New Jersey, New Brunswick, NJ (US); Emory University, Atlanta, GA (US)

( * ) Notice: Subject to any disclaimer, the term of this patent is extended or adjusted under 35 U.S.C. 154(b) by 0 days.

(21) Appl. No.: 14/267,012

(22) Filed: May 1, 2014

(65) Prior Publication Data

US 2015/0368668 A1    Dec. 24, 2015

Related U.S. Application Data

(63) Continuation-in-part of application No. 12/988,864, filed as application No. PCT/US2009/002502 on Apr. 22, 2009, now abandoned.

(60) Provisional application No. 61/046,944, filed on Apr. 22, 2008.

(51) Int. Cl.
| | |
|---|---|
| C12Q 1/70 | (2006.01) |
| A61K 39/29 | (2006.01) |
| C12N 15/40 | (2006.01) |
| C12N 15/79 | (2006.01) |
| C12N 15/86 | (2006.01) |
| C07K 16/10 | (2006.01) |
| A61K 39/00 | (2006.01) |

(52) U.S. Cl.
CPC ............ *C12N 15/86* (2013.01); *C07K 16/109* (2013.01); *A61K 2039/505* (2013.01); *C07K 2317/76* (2013.01); *C12N 2770/24222* (2013.01); *C12N 2770/24233* (2013.01); *C12N 2770/24251* (2013.01)

(58) Field of Classification Search
None
See application file for complete search history.

(56) References Cited

U.S. PATENT DOCUMENTS

| | | |
|---|---|---|
| 6,326,171 B1 | 12/2001 | Selby et al. |
| 7,659,103 B2 | 2/2010 | Wakita et al. |
| 7,935,676 B2 | 5/2011 | Wakita et al. |
| 8,216,834 B2 | 7/2012 | Colloca et al. |
| 8,535,686 B2 | 9/2013 | McCaffrey et al. |
| 2001/0016351 A1 | 8/2001 | Sorge et al. |
| 2002/0182706 A1 | 12/2002 | Maertens et al. |
| 2005/0042721 A1* | 2/2005 | Fang .................. C07K 16/00 435/69.1 |
| 2005/0069865 A1* | 3/2005 | Neville ............. G01N 33/5767 435/5 |
| 2005/0261224 A1 | 11/2005 | Kuchroo et al. |
| 2006/0246090 A1 | 11/2006 | Brett et al. |
| 2006/0275323 A1 | 12/2006 | Depla et al. |
| 2007/0059820 A1 | 3/2007 | Fang et al. |
| 2007/0065912 A1 | 3/2007 | Carson et al. |
| 2007/0231875 A1 | 10/2007 | Chohan et al. |

FOREIGN PATENT DOCUMENTS

WO    WO 2009/131681 A2 * 10/2009

OTHER PUBLICATIONS

Martyn JC, Dong X, Holmes-Brown S, Pribul P, Li S, Drummer HE, Gowans EJ. Transient and stable expression of the HCV envelope glycoproteins in cell lines and primary hepatocytes transduced with a recombinant baculovirus. Arch Virol. Feb. 2007;152(2):329-43. Epub Oct. 6, 2006.*
Lee KJ, Suh YA, Cho YG, Cho YS, Ha GW, Chung KH, Hwang JH, Yun YD, Lee DS, Kim CM, Sung YC. Hepatitis C virus E2 protein purified from mammalian cells is frequently recognized by E2-specific antibodies in patient sera. J Biol Chem. Nov. 28, 1997;272(48):30040-6.*
Bukh J. Polyprotein [Hepatitis C virus genotype 2]. NCBI Reference Sequence: YP_001469630.1. Dep. Oct. 1, 2007.*
Shao S, Zhou H, Tong Y, Ren Y, Chen Z. [Study of neutralization antibodie induced by DNA vaccine of HCV envelope protein 2 in mice]. Wei Sheng Van Jiu. May 2011;40(3):295-8.
Krey T, d'Aiayer J, Kikuti CM, Saulnier A, Damier-Piolle L, Petitpas I, Johansson OX, Tawar RG, Baron B, Robert B, England P, Persson MA, Martin A, Rey FA. "The disulfide bonds in glycoprotein E2 of hepatitis C virus reveal the tertiary organization of the molecule." PLoS Pathog. Feb. 19, 2010;6(2):e1 000762.
Whidby J, Mateu G, Scarborough H, Demeler B, Grakoui A, Marcotrigiano J. Blocking hepatitis C virus infection with recombinant form of envelope protein 2 ectodomain. J Virol. Nov. 2009;83(21):11078-89. doi: 10.1128/JVI.00800-09. Epub Aug. 26, 2009.
Michalak JP, Wychowski C, Choukhi A, Meunier JC, Ung S, Rice CM, Dubuisson J. "Characterization of truncated forms of hepatitis C virus glycoproteins." J Gen Virol. Sep. 1997;78 ( Pt 9):2299-306.
Liu J, Zhang XX, Zhang SY, Lu M, Kong YY, Wang Y, Li GO. "Expression of hepatitis C virus E2 ectodomain in *E. coli* and its application in the detection of anti-E2 antibodies in human sera." Acta Biochim Biophys Sin (Shanghai). Jan. 2004;36(1):57-63.
Liu J, Kong Y, Zhu L, Wang Y, Li G. "High-level expression of the C-terminal hydrophobic region of HCV E2 protein ectodomain in *E. coli*." Virus Genes. 2002;25(1):5-13.
Wunschmann S, Muller HM, Stipp CS, Hemler ME, Stapleton JT. "In vitro interaction between hepatitis C virus (HCV) envelope glycoprotein E2 and serum lipoproteins (LPs) results in enhanced cellular binding of both HCV E2 and LPs", J. Infect Dis. Oct. 15, 2006:194(8):1 058-67. Epub Sep. 8, 2006.

(Continued)

Primary Examiner — Stacy B Chen
(74) Attorney, Agent, or Firm — Licata & Tyrrell P.C.

(57) ABSTRACT

Methods of producing and using Hepatitis C virus (HCV) eE2 polypeptides are described.

16 Claims, 35 Drawing Sheets
(19 of 35 Drawing Sheet(s) Filed in Color)

(56) References Cited

OTHER PUBLICATIONS

Lee KJ, Suh YA, Cho YG, Cho YS, Ha GW, Chung KH, Hwang JH, Yun YO, Lee OS, Kim CM, Sung YC. "Hepatitis C virus E2 protein purified from mammalian cells is frequently recognized by E2-specific antibodies in patient sera." J Bioi Chem. Nov. 28, 1997;272(48):30040-6.

Drummer et al. "Cell Surface Expression of Functional Hepatitis C Virus E1 and E2 Glycoproteins." FEBS Lett. vol. 546 (Nos. 2-3), pp. 385-390, 2003.

InvivoGen. pFUSE-Fc Vectors. www.invivogen.com via WayBack Machine, Internet archive (www.web.archive.org). Website as of Oct. 13, 2007.

Kapp et al., "Post-Targeting Functions of Signal Peptides", Madame Curie Bioscience Database, 2000. Available from: http://www.ncbi.nlm.nih.gov/books/NBK6322/.

Santolini E, Pacini L, Fipaldini C, Migliaccio G, Monica N. "The NS2 protein of hepatitis C virus is a transmembrane polypeptide." J Virol. Dec. 1995;69(12):7461-71.

PcDNA-4-HisMax. Manual. Invitrogen (Life Technologies). Cat. No. V864-20. Publication revision date Nov. 8, 2011.

Austral Biologicals. "Recombinant E2 protein." www.australbiologicals.com via WayBack Machine, Internet archive (www.web.archive.org). Website as of Mar. 2, 2007.

Yanagi M, Purcell RH, Emerson SU, Bukh J. "Hepatitis C virus: an infectious molecular clone of a second major genotype (2a) and lack of viability of intertypic 1 a and 2a chimeras." Virology. Sep. 15, 1999;262(1):250-63. PubMed PMID: 10489358.

McKeating et al. "Diverse Hepatitis C Virus Glycoproteins Mediate Viral Infection in a CD81-Dependent Manner." J. Virol., vol. 78 (No. 16) pp. 8496-8505, 2004.

Lesniewski et al., Antibody to Hepatitis C Virus Second Envelope (HCV-E2) Glycoprotein: A new marker of HCV Infection Closely Associated with Viremia, Journal of Medical virology; 1995: vol. 45, pp. 415-422.

Yagnik et al., "A Model for the Hepatitis C Virus Envelope Glycoprotein E2" In: Proteins: Structure, Function and Genetics; 2000; vol. 40; p. 355-366.

International Search Report and Written Opinion, dated Nov. 19, 2009, in connection with corresponding International Application No. PCT/US09/02502.

Office Action from the Canadian Patent Office, dated Sep. 17, 2013, in connection with corresponding Canadian Patent Application No. 2,722,423.

\* cited by examiner (384)R*THT*VGGSAAQTTGRLTSLFDMG
PRQKIQLVNTNGSWHINRTALNCNDSL
HTGFIASLFYTHSFNSSGCPERMSACR
SIEAFRVGWGALQYEDNVTNPEDMRP
YCWHYPPRQCGVVSAKTVCGPVYCF*T*
*PS*PVVVGT*TDR*LGAPTYTWGENETDV
FLLNSTRPPLGSWFGCTWMNSSGYTK
TCGAPPCRTRADFNASTDLLCPTDCFR
KHPDTTYLKCGSGPWLTPRCLIDYPYR
LWHYPCTVNYTIFKIRMYVGGVEHRLTA
ACNFTRGDRCNLEDRDRS(664)

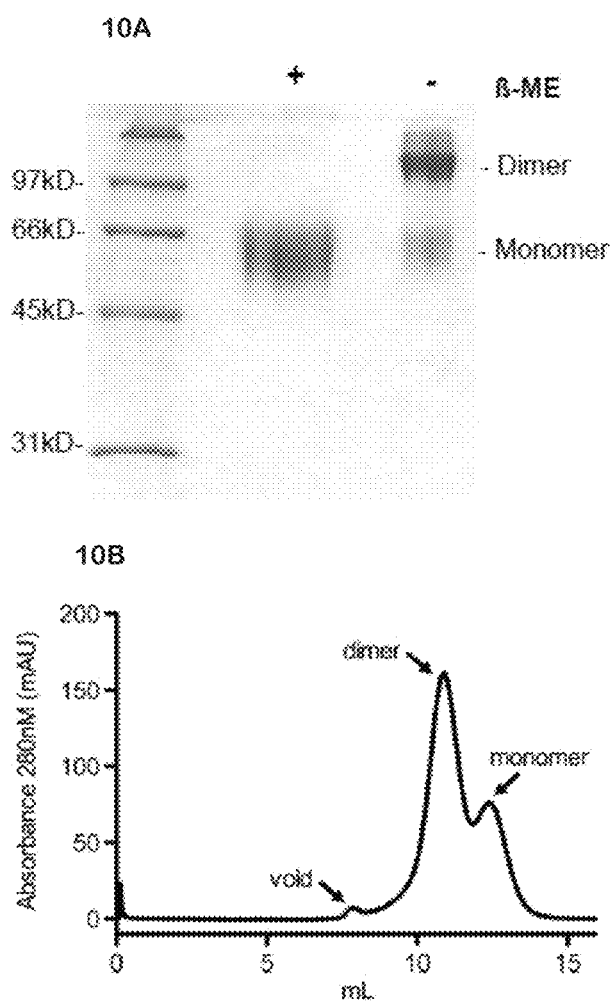

Figure 11
11A
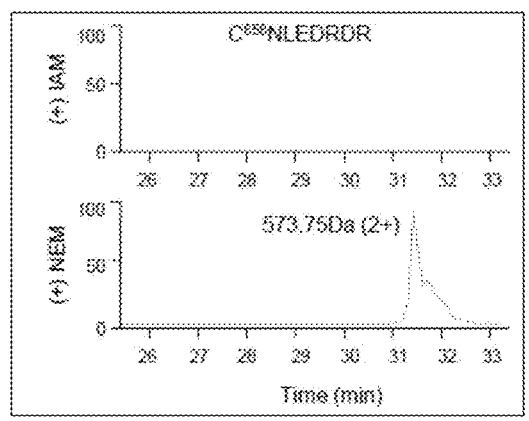
11B
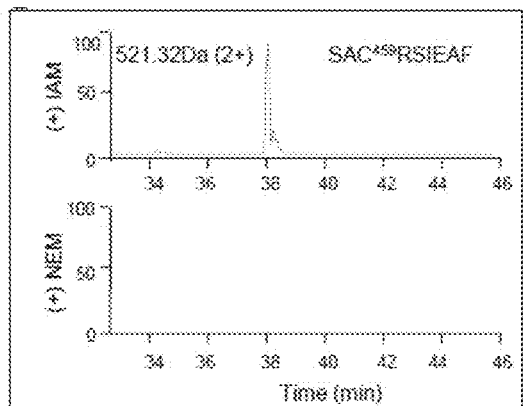
11C
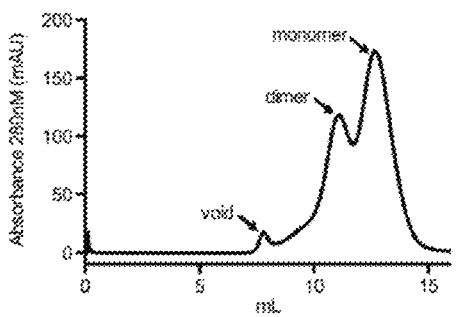

Figure 12
12A
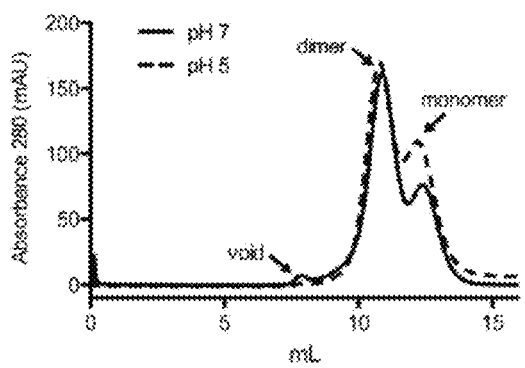
12B
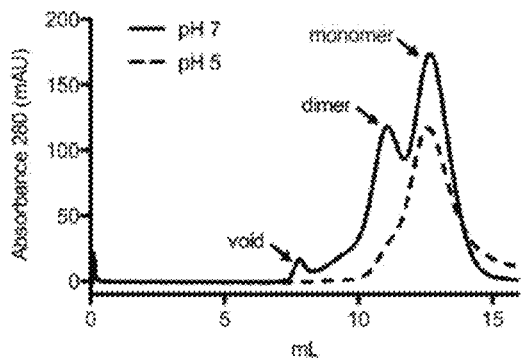

Figure 14
14A
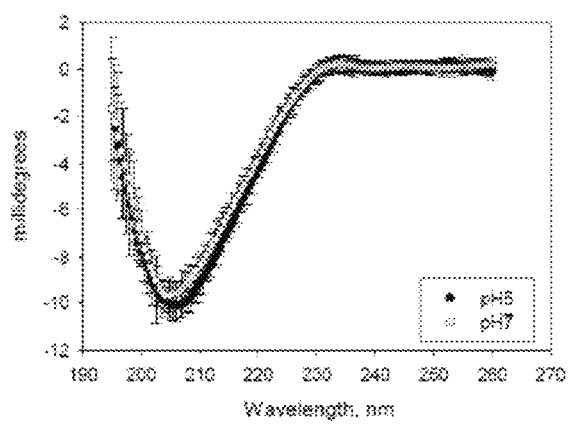
14B
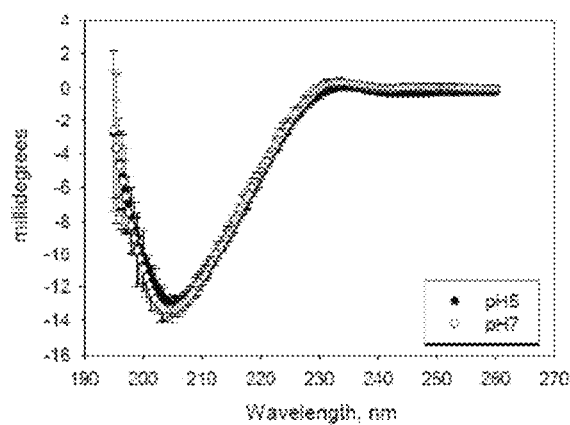

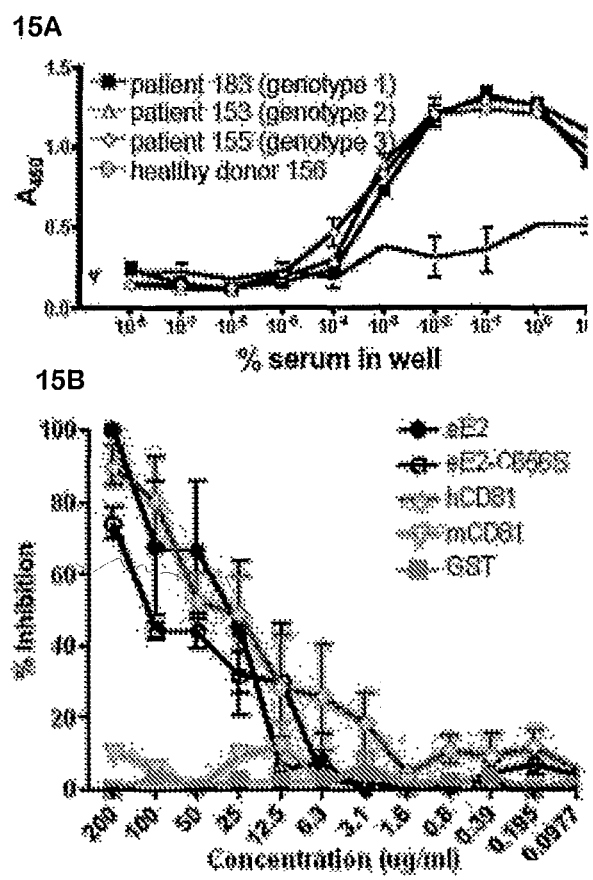

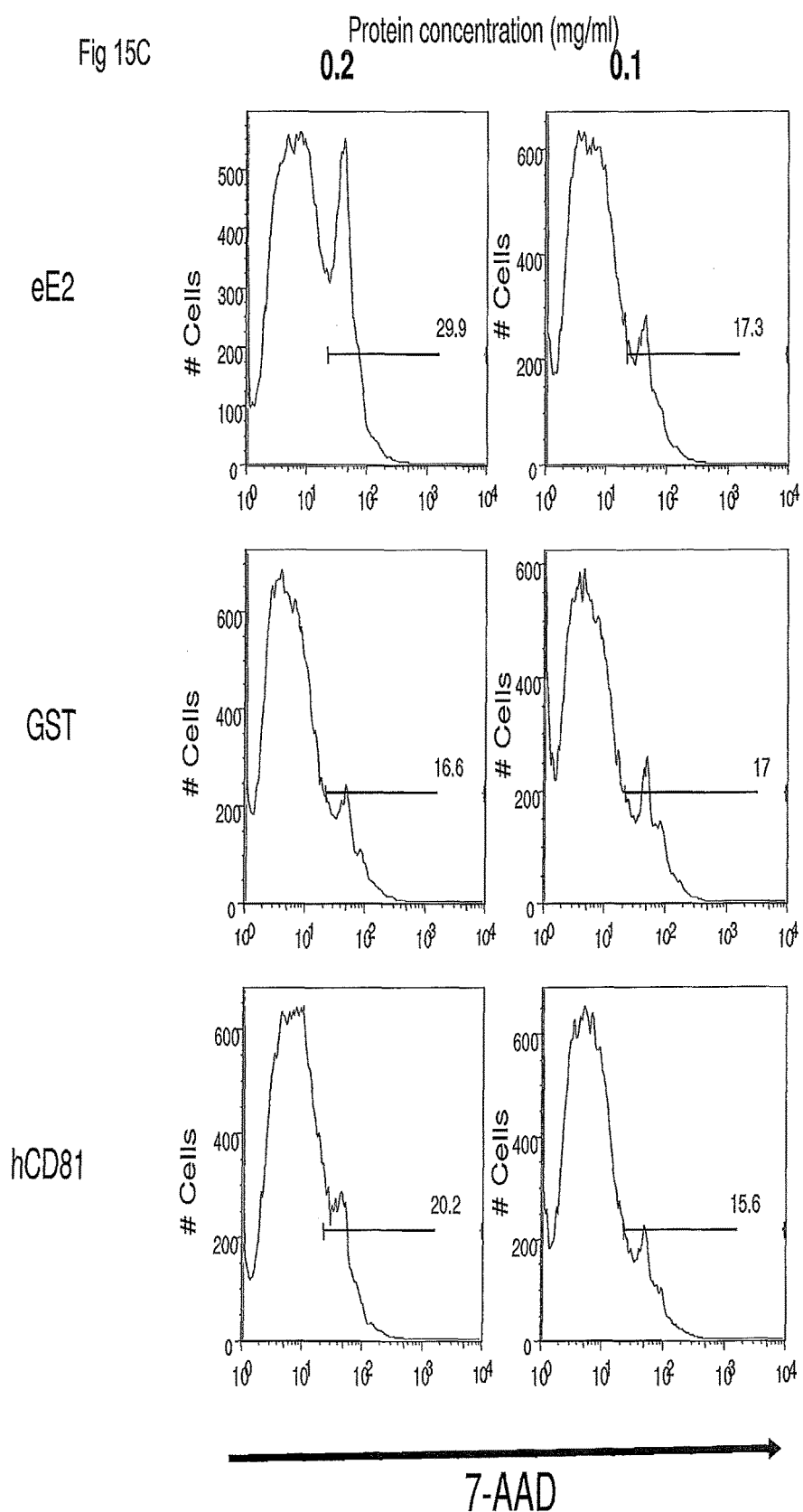

Extended Data Table 1 | Summary of the X-ray crystallographic analyses

| | |
|---|---|
| Data collection | |
| Wavelength | 0.979 Å |
| Space group | P2₁2₁2 |
| Cell dimensions | |
| a, b, c (Å) | 85.96, 194.67, 37.93 |
| α, β, γ (°) | 90, 90, 90 |
| Resolution (Å) | 24.69-2.40 (2.49-2.40)* |
| $R_{merge}$ | 0.118 (1.042) |
| $R_{pim}$ | 0.054 (0.490) |
| I/σ | 9.6 (1.9) |
| Completeness (%) | 100 (100) |
| Redundancy | 5.7 (5.3) |
| Refinement | |
| Resolution (Å) | 24.69-2.40 |
| No. unique reflections | 24349 (2517) |
| $R_{work}/R_{free}$ | 0.217/0.269 |
| No. atoms | |
|   Protein/glycans | 4182 |
|   Solvent | 137 |
|   Ions | 18 |
| B-factors (Å²) | |
|   Protein/glycan | 54 |
|   Solvent | 45 |
|   Ions | 47 |
| R.M.S deviations | |
|   Bond lengths (Å) | 0.006 |
|   Bond angles (°) | 1.14 |
| Ramachandran favored (%) | 96.0 |
| Ramachandran outliers (%) | 0.2 |

*Highest resolution shell is shown in parenthesis.

FIGURE 25

Extended Data Table 2 | Summary of SAXS analyses

| Protein | $R_g$ (Å) | $D_{max}$ (Å) | NSD |
|---|---|---|---|
| E2 core | 27.8±0.03 | 95 | 0.705±0.026 |
| eE2(ΔHVR1) | 28.9±0.05 | 101 | 0.696±0.075 |
| eE2 | 28.2±0.02 | 84 | 0.702±0.054 |
| eE2(ΔHVR1) + CD81 | 36.8±0.22 | 127 | 0.714±0.026 |
| CD81 | 18.8±0.04 | 64 | 0.554±0.007 |
| E2 core pH 5.0 | 27.8±0.07 | 95 | - |
| eE2 pH 5.0 | 27.8±0.07 | 95 | - |

FIGURE 28

HCV E2 CONSTRUCT COMPOSITIONS AND METHODS

CROSS-REFERENCE TO RELATED APPLICATIONS

This application is a continuation-in-part of U.S. patent application Ser. No. 12/988,864, which is a National Stage Entry of International Application No. PCT/US09/02502, filed on Apr. 22, 2009, which claims priority to U.S. Provisional Patent Application No. 61/046,944, filed on Apr. 22, 2008, the disclosures of which are hereby incorporated by reference in their entireties.

BACKGROUND OF THE INVENTION

Hepatitis C virus (HCV) continues to be a global epidemic. In most cases, HCV infection becomes chronic and can persist for decades, leading to cirrhosis, end-stage liver disease and hepatocellular carcinoma. Currently, 2% of the human population—approximately 123 million people—is infected with HCV. In fact, there are 3-4 times more individuals infected with HCV than HIV, making virus transmission a major public health concern. In the United States, HCV infection is the most common cause of liver transplantation and results in 10,000 to 20,000 deaths a year. There is no vaccine, and current HCV therapy, pegylated interferon-alpha in combination with ribavirin, leads to a sustained response in only 50% of genotype 1-infected patients, the prevalent genotype in the United States. The current HCV treatment stimulates the patient's immune system to clear the virus, but numerous side effects cause many patients to prematurely stop treatment. Two new protease inhibitors now used to improve treatment outcomes do not eliminate the need for interferon-alpha and ribavirin. Given the high prevalence of infection and poor response rate, inhibitors that specifically target HCV proteins with fewer side effects are desperately needed. In addition, an effective vaccine would greatly reduce the spread of the virus.

International Patent Publication No. WO 2008/022401 to Mc Caffrey, et. al, describes preparing an HCV E2 polypeptide having internal deletions of the regions within E2. However, this reference does not describe a stable cell line that expresses E2. The cells perform transient expression, which is only good for a few days. The E2 DNA is not incorporated into the genome of the cell and after several days, the cells will remove the gene. This method is inefficient. This publication also does not utilize a construct containing an Fc or protein-A tags.

U.S. Pat. No. 6,326,171 to Chiron describes preparing an HCV E2 polypeptide involving a specific region of E2 that ends at amino acid 715. The construct used does not contain a tag. The cells used for expression are non-human, and included BSC40 (African Green monkey) and F503 (chimpanzee fibroblasts).

U.S. Pat. No. 6,020,122 to Abbott Laboratories describes preparing an HCV E2 polypeptide without the use of a tag. The cells used for expression are CHO (Chinese Hampster Ovary) cells.

However, there still exists a need in the art for more efficient methods of preparing HCV E2 polypeptides, expression of higher levels and higher quality HCV E2 polypeptides, HCV vaccines and inhibitors of HCV infection.

SUMMARY OF THE INVENTION

The invention provides methods for preparing HCV E2 ectodomain (eE2) polypeptides, methods of preparing HCV vaccines, methods of preparing HCV cell entrance inhibitors, and models which could be used to assist with, e.g., development of HCV vaccines and new HCV inhibitors. HCV eE2 polypeptides of the invention include full-length ectodomains of HCV envelope 2 surface protein (E2) and fragments of ectodomains of HCV envelope 2 surface protein (E2). Full length ectodomains of HCV envelope 2 surface protein (E2) include aa 384-656 of HCV J6 [2a] genotype and corresponding sequences of other HCV genotypes. Fragments of HCV envelope 2 surface protein include, e.g., eE2 (DHVR1) and E2 core domains. eE2 (DHVR1) includes, e.g., aa413-656 of HCV J6 [2a] genotype and corresponding sequences of other HCV genotypes. E2 core domain includes, e.g., aa 456-656 of HCV J6 [2a] genotype and corresponding sequences of other HCV genotypes.

A method of producing a hepatitis C virus (HCV) eE2 polypeptide in accordance with the present invention may comprise: (i) providing a construct comprising: a cytomegalovirus (CMV) promoter, a fragment of HCV envelope 2 surface protein (E2), and a cleavage site (e.g., a PreScission Protease cleavage site); (ii) introducing the construct into HEK293T cells; (iii) selecting cells stably expressing the HCV eE2 polypeptide; (iv) incubating the cells stably expressing the HCV eE2 polypeptide in a supernatant, and recovering and purifying the HCV eE2 polypeptide. A fragment of HCV envelope 2 protein may, e.g., be selected from the group consisting of full length ectodomains of E2 (eE2) and fragments of eE2. Full length eE2 may have a sequence identical to or homologous with a sequence selected from the group consisting of SEQ ID No. 1, SEQ ID No. 14, SEQ ID No. 15, SEQ ID No. 16, SEQ ID No. 17, SEQ ID No. 18, SEQ ID No. 19, SEQ ID No. 20, SEQ ID No. 21, and fragments of any one of the foregoing (e.g., fragments of from about 50 to about 270 or from about 70 to about 250 amino acids in length).

In certain embodiments, the construct may further comprise a C-terminal tag (e.g., a human Fc domain or protein-A (ProtA) tag). If a human Fc domain is used as a C-terminal tag, the recovered and purified HCV eE2 polypeptide in some of the preferred embodiments is substantially free from large disulfide-bonded aggregates and comprises a mixture of dimers and monomers of the HCV eE2 polypeptide, the dimers comprising a greater proportion of the mixture and each having an approximate molecular weight of about 120 kDa. If a protein-A (ProtA) tag is used as a C-terminal tag, in some of the preferred embodiments, the recovered and purified HCV eE2 polypeptide comprises or consists essentially of monomers of the HCV eE2 polypeptide having an approximate molecular weight ranging from about 28 kDa to about 50 kDa (e.g., about 32 kDa, about 42 kDa or about 46 kDa).

In some of the preferred embodiments the recovered and purified HCV eE2 polypeptide is conformationally similar to the E2 present on infectious HCV particles, is recognized by antibodies from chronically infected patients and is capable of one or more of the following: competing with $HCV_{cc}$, inhibiting HCV cell entry and/or inducing production of HCV antibodies in a mammal (e.g., a human). In some of these embodiments, the recovered and purified HCV eE2 polypeptide can specifically bind the large extracellular loop of human CD81.

Methods for preparing a HCV E2 peptide in accordance with the invention in some of the preferred embodiments yield more than 15 mg, more than 20 mg, more than 25 mg, or more than 29 mg of the hepatitis C virus (HCV) eE2 polypeptide per liter of the supernatant. Thus, in some of the preferred embodiments, yield, e.g., from about 20 mg to about 300 mg, from about 25 mg to about 300 mg, from about 29 mg to about 275 mg, from about 29 mg to about 250 mg, from about 29 mg to about 200 mg, from about 20 mg to about 200 mg, from about 20 mg to about 150 mg, from about 25 mg to about 100 mg, or from about 29 mg to about 50 mg of the hepatitis C virus (HCV) eE2 polypeptide.

The invention also provides a construct comprising the ectodomain of the hepatitis C virus (HCV) E2 sequence and a mammalian expression system. More particularly, the invention relates to a construct comprising the CMV promoter, prolactin signal sequence, the ectodomain of HCV E2 sequence truncated at a position corresponding to aa 664 of J6[2a] genotype, a thrombin cleavage site and a human Fc domain or ProtA tag. The invention also relates to an expression system for the construct, which is stably expressed in human embryonic kidney 293T cells. In some of the embodiments, continuous protein expression in a bioreactor allows for 4 mg, 5 mg, 8 mg, 10 mg, 12 mg 15 mg, 20 mg, 22 mg, 25 mg, 30 mg, 35 mg, 40 mg, 50 mg or 60 mg of purified protein per liter of cell supernatant.

In a first embodiment, the invention is directed to recombinant HCV E2 ectodomain expression without the production of mostly large, disulfide-bonded aggregates. This process is used to make large quantities of the envelope glycoproteins applicable for a variety of commercial applications including but not limited to: 1) Vaccine design—The recombinant protein can be a subunit vaccine to elicit a strong immune response, protecting individuals from future infection; 2) Therapeutic vaccine—The administration of the protein to patients who are chronically infected with HCV to help the individual develop a more robust immune response either by administration alone or in combination with other medications such as IFN and ribavirin; 3) Diagnostics—enzyme-linked immunoassays can be developed using the purified, recombinant protein to screen patient sera for antibodies against these proteins. Although there are commercial screens currently available for this purpose, the proteins used therein were made in yeast or other expression systems and may not be properly folded and would have different post-translational modifications. Since the present protein is produced in human cells, the post-translational modifications are more similar to those seen on the virus; 4) Small molecule inhibitors—The ability to make a properly folded E2 could be an important reagent for finding small molecules that bind to E2. (As shown in FIG. 7B, the ectodomain of E2 can bind with high specificity and affinity to a cellular receptor CD81. A similar assay could be used to identify small molecules that prevent this interaction; and 5) Production of neutralizing antibodies against HCV E2.

In accordance with the above objects, the invention in some of the embodiments is directed to a construct comprising an ectodomain of the hepatitis C virus (HCV) E2 sequence, or a fragment thereof, and a mammalian expression system. The construct may comprise a CMV promoter, prolactin signal sequence, an ectodomain of J6 HCV E2 truncated at amino acid 664 or a corresponding ectodomain of another HCV genotype, a thrombin cleavage site and a human Fc domain or ProA tag. The construct may be specific for the J6 HCV genotype, or another known HCV genotype. In other embodiments, the construct is a mutant form of eE2 in which C656 was mutated from a cysteine amino acid to a different amino acid. In other embodiments, the amino acid is serine.

In accordance with the above objects, the invention is also directed to an expression system for a construct comprising an ectodomain of HCV E2 sequence, which is stably expressed in human embryonic kidney (HEK) 293T cells.

In accordance with the above objects, the invention is also directed to a method of producing HCV eE2 polypeptide comprising: the ectodomain of the hepatitis C virus (HCV) E2 sequence, or a fragment thereof, and a mammalian expression system. The construct may comprise a CMV promoter, a prolactin signal sequence, an ectodomain of HCV E2 truncated at amino acid 664 of J6 HCV E2 or a corresponding ectodomain of another HCV genotype, a thrombin cleavage site and the human Fc domain, introducing the construct into HEK293T cells, selection of cells stably expressing the polypeptide, incubating the cells stably expressing the polypeptide in a supernatant, and recovering and purifying the polypeptide from the supernatant. In other embodiments, the method produces about 0.5 mg to about 15 mg or from about 10 mg to about 40 mg of polypeptide per liter of supernatant. In other embodiments, the method produces about 0.5 mg to about 4 mg of polypeptide per liter of supernatant. In other embodiments, the method produces about 0.5 to about 2 mg of polypeptide per liter of supernatant. In other embodiments, the method produces the HCV eE2 HCV J6 genotype polypeptide. In other embodiments, the construct is a mutant form of eE2 in which C656 was mutated from a cysteine amino acid to a different amino acid. In other embodiments, the different amino acid is serine. In other embodiments, the incubation occurs in one or more vessels suitable for providing an environment for the cells to express the polypeptide. In other embodiments, the vessels are in a rotating bottle apparatus. In other embodiments, the vessel is a bioreactor.

In accordance with any of the above objects, the invention is also directed to a method wherein the produced polypeptide is folded and sequesters human HCV receptor sites (i.e., blocks HCV binding to these sites). In other embodiments, the amount of polypeptide in monomer and dimer form exceeds the amount of polypeptide existing in higher orders, and is recognized by antibodies in the sera of patients infected with HCV. In other embodiments, the polypeptide contains 16 preserved cysteine residues.

In accordance with any of the above objects, the invention is also directed to a method of vaccinating a patient comprising administering to a patient in need thereof, a sufficient amount of a polypeptide produced by a method of the embodiments above to produce a strong immune response protecting the patient from future HCV infection.

In accordance with any of the above objects, the invention is also directed to a method of vaccinating a patient chronically infected with HCV comprising administering to a patient in need thereof, a sufficient amount of a polypeptide produced by a method of the embodiments above to produce a more robust immune response. In other embodiments, an additional therapeutic agent that provides a more robust immune response.

In accordance with any of the above objects, the invention is also directed to a method of inhibiting HCV infection in a human patient comprising administering to a patient in need thereof, a sufficient amount of a polypeptide produced by a method of the embodiments above to effectively block entry into the entry site of human cells. In other embodiments, the sufficient amount of polypeptide is non-toxic to a human patient. In other embodiments, a sufficient amount of an active fragment of the polypeptide is administered.

In accordance with any of the above objects, the invention is also directed to a method for detection of antibodies to HCV in human sera comprising contacting the sera with the polypeptide as prepared herein.

In accordance with any of the above objects, the invention is also directed to a method of producing antibodies comprising introducing the polypeptide as prepared herein to achieve a response that leads to production of antibodies to said polypeptide.

The invention is also directed to methods of preparing HCV cell entrance inhibitors. Cell entrance inhibitors may comprise a hepatitis C virus (HCV) eE2 polypeptide according to the present invention or have a structure conformationally similar to the hepatitis C virus (HCV) eE2 polypeptide.

The invention is also directed to a model or crystal of an E2 core comprising a structure of an E2 core domain of HCV J6 genotype, the E2 core domain comprising: (i) a four-stranded antiparallel N-terminal β-sheet comprising an N-terminal loop, a first strand, a second strand, a third strand, a fourth strand, and a first loop between the second and third strands, the four strands of the N-terminal β-sheet stabilized by two disulfide bonds between the first strand and the third strand (C7 (510) and C8 (554)) and the N-terminal loop with the fourth strand (C5 (496) and C9 (566)), the first loop between the second and the third strands is flexible and comprises amino acid sequences implicated in CD81 binding; (ii) a four-stranded antiparallel β-sheet comprising a fifth strand, a sixth strand, a seventh strand and an eighth strand and an α-helix (H2) loop between the sixth strand and the seventh strand, the four-stranded antiparallel β-sheet B stabilized by a disulfide bond (C14 (611) and C16 (648)) between the sixth strand and the eighth strand, the seventh and the eighth stands comprising approximately nine amino acids each and together encompassing an epitope of 2A12 antibody; and (iii) a second loop after the fourth strand, the second loop followed by a first short helix loop (H1); wherein the first short helix is followed by the four-stranded β-sheet B; a plane of the four-stranded antiparallel N-terminal β-sheet and a plane of the four-stranded antiparallel β-sheet are approximately perpendicular to each other; and the two β-sheets held together by two disulfide bonds, connecting the N-terminal loop with the α-helix loop (H2) (C4 (488) with C15 (624)) and the second loop with the first short helix (H1) (C10 (571) and C13 (601)). In some of the preferred embodiments, the model is used to identify polypeptides, which are conformationally similar to the structure of the E2 core domain of HCV J6 genotype, or a different known genotype of HCV. The identified polypeptides may then be tested as potential inhibitors of HCV cell entry.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 10. (A) Shows SDS-PAGE analysis of purified eE2 in the presence and absence of β-mercaptoethanol (β.-ME) and stained with Coomassie blue. (B) Is a graphical depiction of purified eE2 applied to a Superdex 200 size exclusion column equilibrated with 50 mM HEPES pH 7.5, 150 mM KCl, 5% glycerol. The arrows denote the position of the void, dimer, and monomer.

FIG. 11. Shows differential labeling of free and disulfide-linked cysteines. Free and disulfide bonded cysteines were labeled with NEM (an addition of 57 Da) and IAM (an addition or 125 Da), respectively. LC-MS data for peptides containing C656 (A) (SEQ ID No. 12) and C459 (B) (SEQ ID No. 13) are shown. The top spectra correspond to labeling with NEM and the bottom spectra with IAM. C656 is free, while C459 is found in a disulfide bond. All of the other cysteine residues were labeled with IAM (data not shown), suggesting the formation of eight disulfide bonds. (C) Is a graphical depiction of purified eE2-C656S applied to a Superdex 200 size exclusion column equilibrated with 50 mM HEPES pH 7.5, 150 mM KCl, 5% glycerol. The arrow denotes the position of the void, dimer, and monomer.

FIG. 12. Shows size exclusion chromatography of eE2 and eE2-C656S at pH7 and pH5. eE2 samples were applied to a Superdex 200 column equilibrated with 25 mM sodium phosphate pH 5.0 or 7.0, and 50 mM KCl. The location of void, dimer and monomer are noted.

FIG. 14. Is a graphical depiction of circular dichroism spectroscopy of eE2 and eE2-C656S at pH 7 and pH 5. CD spectra are shown as millidegrees versus wavelength (nm). Error bars for each data point are given.

FIG. 25 shows summary of the X-ray crystallographic analyses.

FIG. 28 shows summary of SAXS analyses.

FIG. 29a shows an overlay of E2 core (a) and eE2. The expected void volume and observed elution positions of individual proteins are indicated.

FIG. 29b shows elution profiles from Superdex 200 gel filtration at pH 7.5 (blue) and pH 5.0 (red). The expected void volume and observed elution positions of individual proteins are indicated.

FIG. 29c shows the SAXS envelope of CD81-LEL fit with a dimer crystal structure (PDB 1G8Q). The individual proteins of the CD81-LEL dimer are colored red and blue.

DETAILED DESCRIPTION OF THE INVENTION

Hepatitis C virus (HCV) is a significant public health concern with approximately 160 million people infected worldwide[101].

Figure 1:
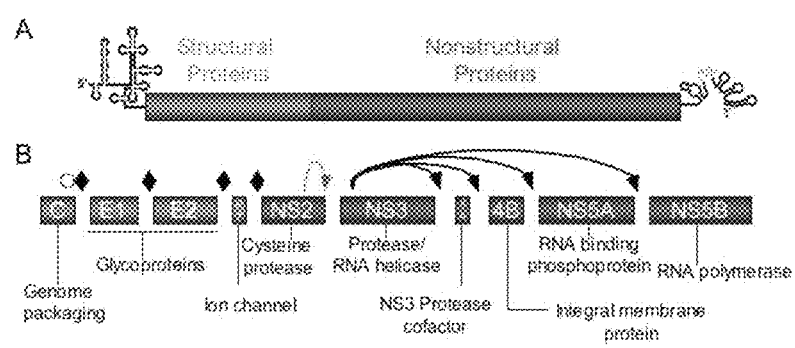
FIG. 1. (A) is a diagram showing the organization of the HCV genome showing the 5' and 3' NTRs. The open reading frame is represented by the rectangle and is colored light grey for the structural proteins and dark grey for the non-structural proteins. (B) Polyprotein processing scheme. The black diamonds and open circle denote the cleavage sites for signal peptidase and signal peptide peptidase, respectively. The arrows signify the cleavages performed by the viral encoded NS3-4A (black) and NS2-3 (red). A brief description of each protein is given.
Figure 2:
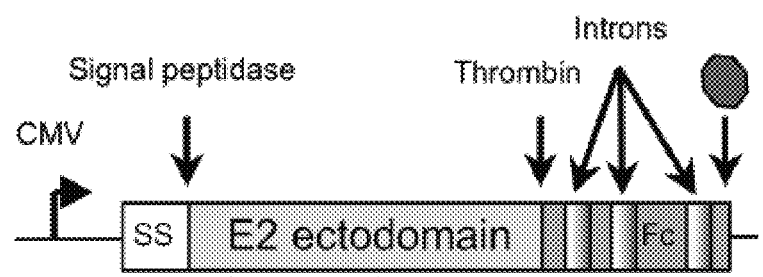
FIG. 2. is a schematic representation of the mammalian expression constructs. Expression is driven by the CMV promoter. The protein consists of an N-terminal signal sequence, the ectodomain of HCV E2, the Fc tag for protein purification and the Fc introns.

Since its identification in 1989, phylogenetic analysis of various isolates has resulted in the classification of seven distinct genotypes that are further divided into a number of subtypes (e.g. 1a, 1b, 1c, etc.). The HCV virion consists of an enveloped nucleocapsid containing the viral genome, a single-stranded, positive sense RNA that encodes a single, open-reading frame (FIG. 1).

HCV belongs to the genus Hepacivirus of the Flaviviridae family. Other members of the family include the flavivirus and pestivirus genera, which consist of arthropod-borne viruses and important livestock pathogens, respectively[116].

Once the virus penetrates a permissive cell, the HCV genome is released into the cytosol where the viral RNA is translated in a cap-independent manner by an internal ribosome entry site (IRES) located within the 5' nontranslated region (NTR). Translation generates a viral polyprotein that is proteolytically processed by cellular and viral encoded proteases into ten proteins (FIG. 1). The N-terminal region is cleaved by cellular signal peptidase and signal peptide peptidase to yield the structural components of the virus particle (Core, envelope proteins E1 and E2) and an ion channel (p7). The mature nonstructural proteins (NS2, NS3, NS4A, NS4B, NS5A, and NS5B) are liberated by two essential viral enzymes: the NS2-3 cysteine protease and the NS3-4A serine protease. NS3-5B comprise the minimal viral proteins necessary to form the RNA replication machinery or replicase. HCV replication occurs in association with the perinuclear and ER membranes, utilizing both cellular and viral proteins. Replication involves the synthesis of a genome-length, minus strand that serves as a template for the production of new positive strands for packaging. Not much is known about HCV assembly and egress, since a system to study these processes has not been available until recently, however extrapolations have been made from comparison with other flaviviruses. HCV virion assembly is thought to occur on the ER membrane. Newly synthesized, genomic RNAs are encapsulated by core. These nucleocapids bud into the ER, encircling it with the envelope membrane and HCV glycoproteins. The virions travel through the secretory pathway and are released at the cell membrane.

HCV infection often results in chronic hepatitis, liver cirrhosis and hepatocellular carcinoma. Little is known about the molecular mechanism that mediates cell entry and membrane fusion, although E2 is predicted to be a class II viral fusion protein. No vaccine is available and current therapies are effective against some, but not all, genotypes.

HCV is an enveloped virus with two surface glycoproteins (E1 and E2). E2 binds to the host cell through interactions with scavenger receptor class B type I (SR-BI) and CD81, and serves as a target for neutralizing antibodies[102-4].

Described below, e.g., is the structure of the E2 core domain in complex with an antigen-binding fragment (Fab) at 2.4A° resolution.

HCV Envelope Glycoprotein 2 (E2)

The flavivirus envelope glycoprotein (E) is a class II fusion protein and HCV E2 was expected to have a similar fold[113,117,118]. All class II fusion proteins have a common elongated structure, consisting of predominantly β-sheets, and exist as homo- or heterodimers with the membrane-fusion, hydrophobic peptide buried at the dimer interface at neutral pH. On receptor binding and/or exposure to low pH, these proteins undergo self-rearrangement into stable trimers, exposing the fusion peptide and resulting in viral and host membrane fusion. Despite containing a similar extended organization, the recent structure of the pestivirus bovine viral diarrhoea virus (BVDV) E2 glycoprotein does not represent a typical class II fusion protein fold and lacks an apparent fusion peptide, indicating that it is unlikely to be a class II fusion protein[119,120].

HCV envelope glycoprotein 2 (E2) is a type I transmembrane protein with an amino-terminal ectodomain connected to a carboxy-terminal transmembrane helix through an amphipathic, α-helical stem (FIG. 16a)[105,106].

E2 is highly modified post-translationally with 9-11 N-linked glycosylation sites and 18 cysteine residues that are conserved across all genotypes. For ease of comparison with other genotypes, we refer to the cysteines and N-linked glycosylation sites as C1 to C18 and N1 to N11, respectively, with residue numbers from the J6 genotype (2a) given in parentheses.

HCV E2 is modified by N-linked glycosylation, which is necessary for proper folding and immune invasion.

E2 from the J6 genotype has 11 glycosylation sites.

Figure 30:
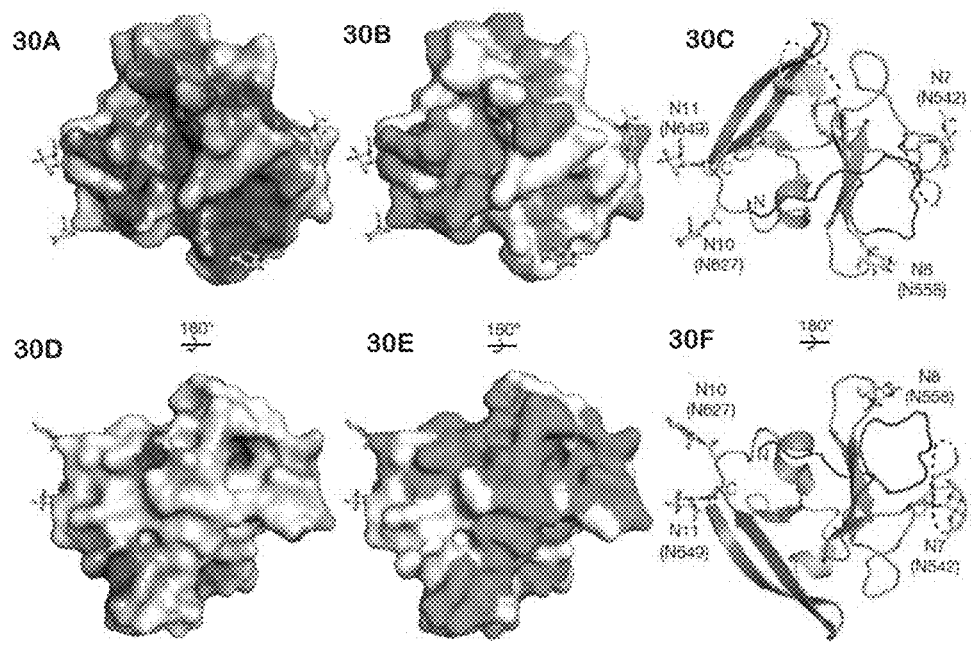
FIG. 30 shows surface features of E2. The surface of the E2 core domain colored for electrostatic potential (a and d)-blue (basic), white (neutral), red (acidic) at ±5 kT $e^{-1}$—and sequence identity (b and e) (green) from the alignment in FIG. 18c, (F) Ribbon diagrams highlighting the location of the N-linked glycosylation sites. The orientations of d-f as well as a-c are identical. The orientation in d-f is rotated 180° about a horizontal axis from the view in a-c.
Figure 31:
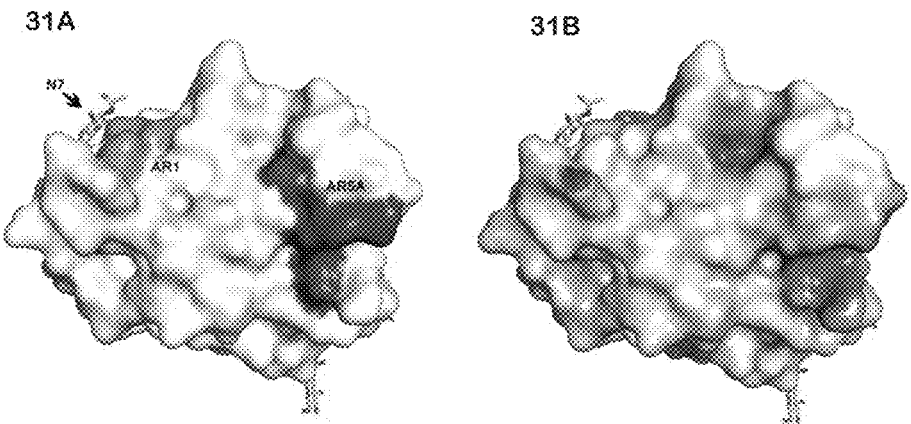
FIG. 31 shows epitope mapping of conformational antibodies on E2 core surface. (A) Surface epitopes of AR1 (orange) are shown. AR1 blocks the E1E2 heterodimer binding to CD81. AR5A (purple) inhibits E1E2 heterodimerization and is mapped on a well-conserved hydrophobic surface of the core. (B) Surface of E2 core colored by electrostatic potential. The view in a and b is identical.
Figure 32:
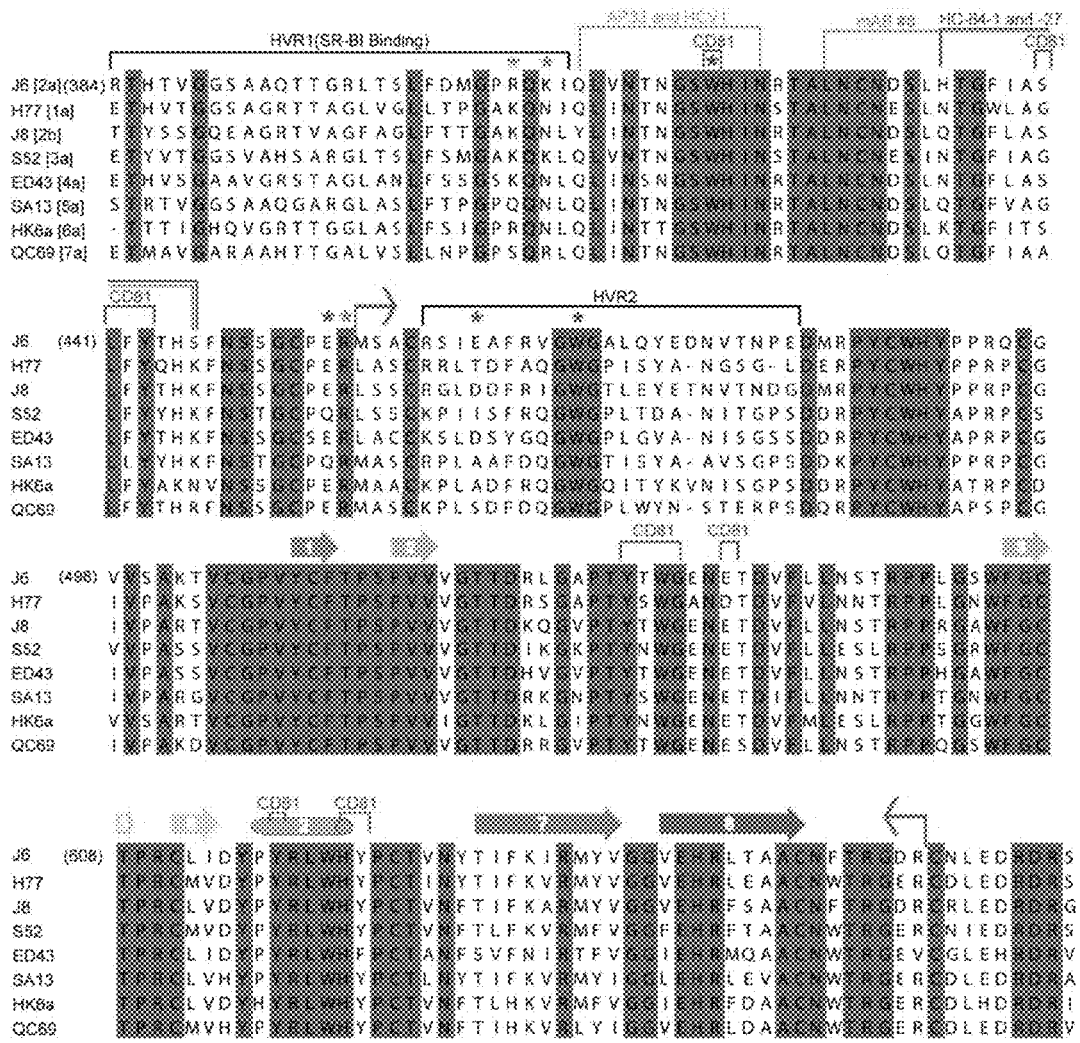
FIG. 32 shows eE2 sequence alignments of J6 [2a] (SEQ ID No. 14), H77 [1a] (SEQ ID No. 15), J8 [2b] (SEQ ID No. 16), S52[3a] (SEQ ID No. 17), ED43 [4a] (SEQ ID No. 18), SA13 [5a] (SEQ ID No. 19), HK6a [6a] (SEQ ID No. 20), and QC69 (SEQ ID No. 21). Red bent arrows indicate the N- and C-terminal boundaries of the E2 crystallization construct. Cylinders and arrows represent α-helices and β-strands, respectively, and are colored according to cartoon representation in FIG. 17. CD81 binding regions are bracketed in red; hypervariable regions are bracketed in black. SR-BI binds to HVR1. The asterisks indicate the location of trypsin (blue), chymotrypsin (green) and GluC (magenta) cleavage sites. The binding sites of neutralizing antibodies for which structural information is available are colored orange for HCV1 and AP33, blue for mAb 8, and purple for HC34-1 and HC34-17.
Figure 33A:
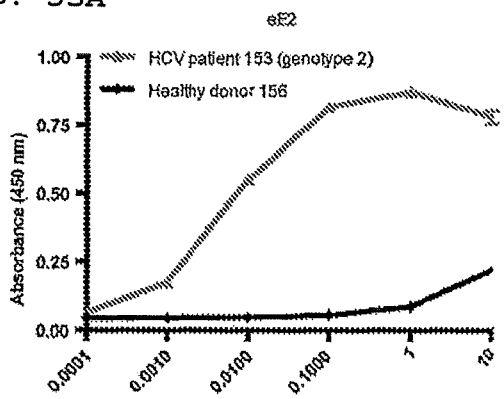
FIG. 33 shows functional analyses of eE2 and E2 core. (A) Antibodies from patient sera infected with HCV genotype 2 show a concentration-dependent binding to eE2 (red) whereas healthy donor sera exhibit only background binding (black). (B) Similar binding is observed for E2 core. The measurements were done in triplicate with the error bars representing the standard error of the mean (s.e.m.). (C) E2 core (light grey) shows reduced binding to CD81 when compared to eE2 (dark grey) by an ELISA. Bars with stripes indicate E2 binding to a negative control, BSA. The solid black bar indicates CD81 binding to PBS, used to verify the absence of background. The measurements were done in triplicate with the error bars representing the s.e.m. (D) eE2 (blue) and CD81-LEL (positive control, grey) inhibit the infection. E2 core (red) shows reduced inhibition. HIV gp140 (black) expressed in the same system was used as a negative control. The measurements were done in triplicate with the error bars representing the s.e.m. e, To rule out the possibility of toxic effects from the recombinant proteins, the cell viability was measured as described in Methods, using similar protein concentrations as in FIG. 33E. In an ELISA, 2A12 (red), and an irrelevant antibody, H113 (grey), fail to neutralize HCVcc infection. 2Cl (positive control, black), a mouse monoclonal antibody that binds to the disordered N-terminal region of eE2, blocks infection. The measurements were done in triplicate with the error bars representing the s.e.m.
Figure 33B:
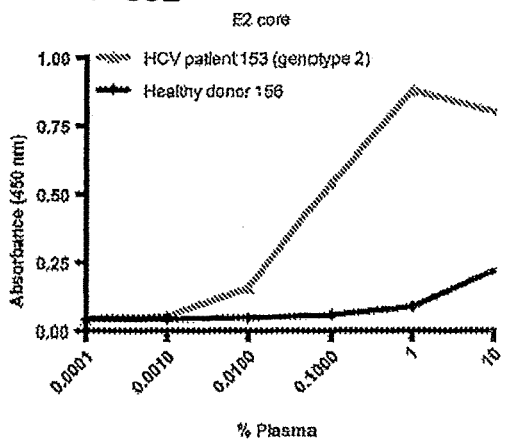
Figure 33C:
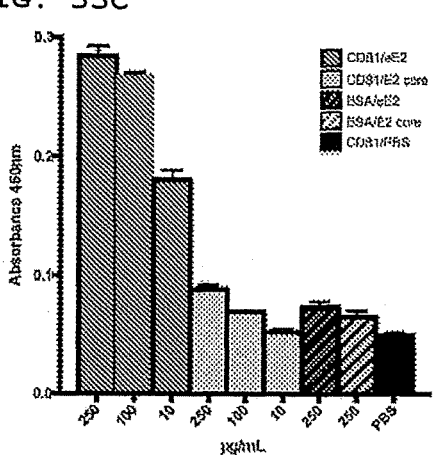
Figure 33D:
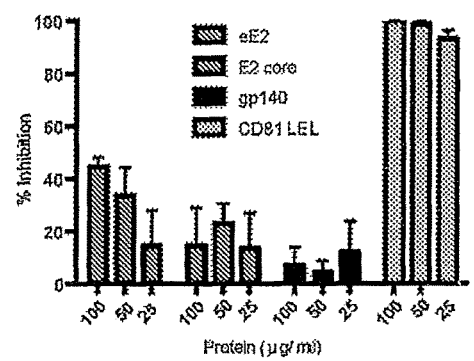
Figure 33E:
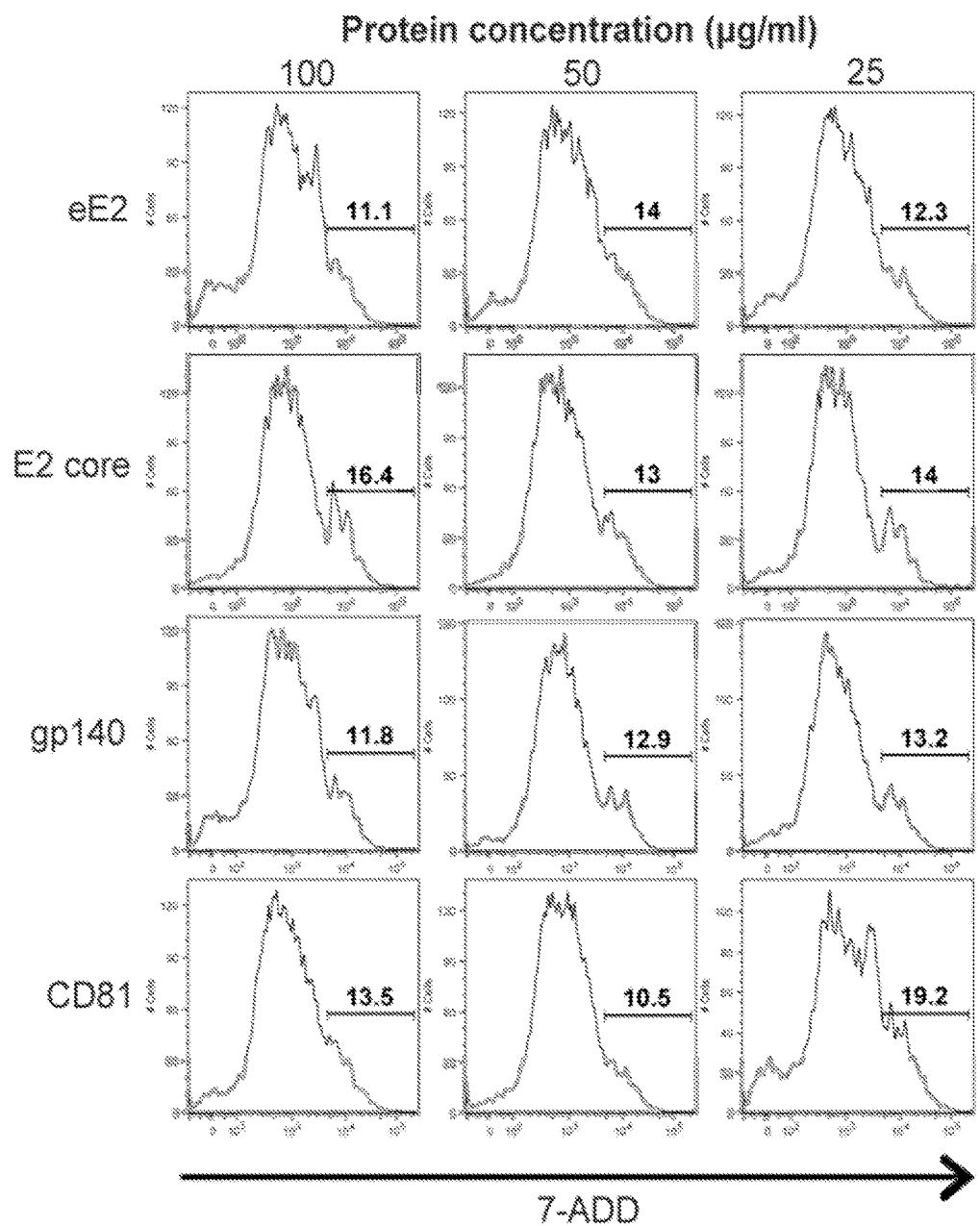

In certain embodiment, four of the glycosylation sites are in the flexible N-terminal region, which were deleted, and seven are in the core domain (N5-N11). The location of N7, N8, N10 and N11 are modelled in the final E2 core structure. All of these glycans are present in loop areas, indicating that these sites are solvent exposed and flexible. Mutagenesis studies in HCVcc have shown that N6, N8 and N10 are integral for virus infectivity. Removal of the N6 site results in improved CD81 binding, whereas N8 and N10 mutations destabilize the protein and cause defective particle production[122]. Both sheets have one critical glycosylation site: N8 in sheet A and N10 in sheet B. All four of the observed glycosylation sites are on the periphery of the core and are located on a highly basic surface (FIG. 30). The opposite surface is predominantly hydrophobic and highly conserved when compared to the basic surface. Furthermore, the epitope for antibodies (AR1, AR3A and AR3C) that inhibit E1E2 binding to CD81 is located at the interface of the hydrophobic and basic surfaces, including the N7 glycosylation site (FIG. 31). Interestingly, N7 is only 7 residues away from N6, which has a critical effect on CD81 binding. Epitopes for antibodies (that is, AR5) that block E1E2 heterodimerization are also found on the hydrophobic surface, making it highly plausible that this surface is interacting with E1 in the context of the viral particle[104]. The precise roles played by E1 and E2 in membrane fusion are not fully understood. It has been predicted that amino acids 262-290 in E1 as well as 416-430, 504-522 and 604-624 in E2 are important for fusion[113,123,124]. In the structure, the potential fusion regions in E2 (504-522 and 604-624) are located in secondary structure elements within the hydrophobic core and therefore unlikely to serve as the fusion peptide. Furthermore, size-exclusion chromatography and SAXS analyses at low pH indicate that E2 does not undergo oligomeric or structural rearrangement. Thus, it seems unlikely that E2 has a direct role in membrane fusion. However, it is possible that E1 alone or the E1E2 heterodimer has a major role in the fusion process.

Figure 17:
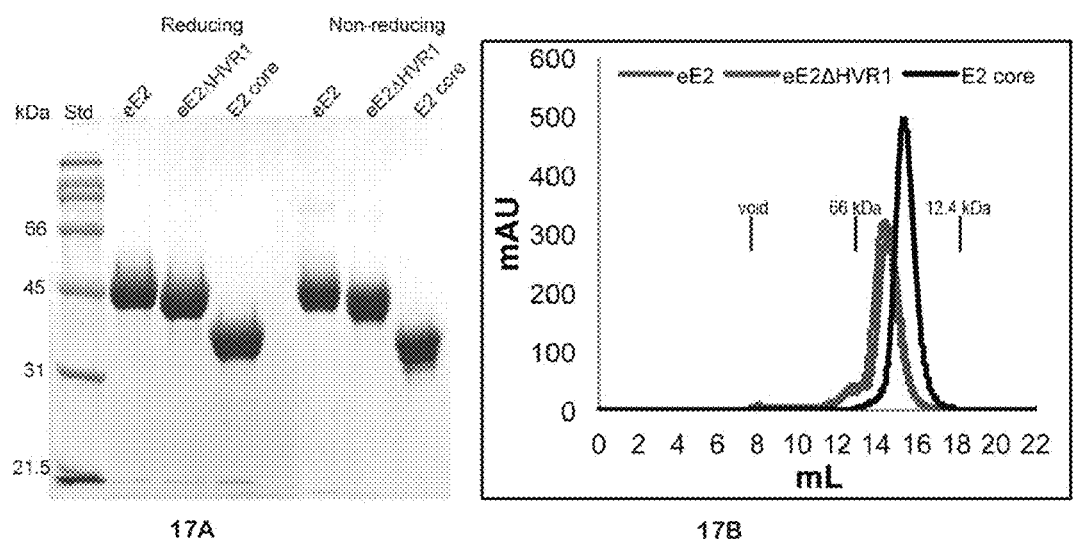
FIG. 17 shows eE2, eE2(DHVR1) and E2 core that are highly soluble and monomeric in solution. (A) A comparison of proteins under reducing and non-reducing conditions is shown by a 10% SDS-PAGE gel with protein standards (Std). (B) Size-exclusion chromatography of eE2, eE2 (DHVR1) and E2 core proteins on a Superdex200 gel filtration column. The elution positions of the void volume (>200 kDa), albumin (66 kDa) and cytochrome C (12.4 kDa) are indicated. Molecular masses of eE2, eE2(DHVR1) and E2 core are about 46 kDa, about 42 kDa and about 32 kDa, respectively.

Full-length, E2 ectodomain (eE2) (384-656) was produced in N-acetylglucosaminyltransferase I-negative (GnTI2)HEK293T cells by a lentiviral expression system and grown in an adherent cell bioreactor. The resulting eE2 protein is monomeric as determined by non-reducing SDS-polyacrylamide gel electrophoresis (PAGE) and size-exclusion chromatography (FIG. 17).

Figure 18:
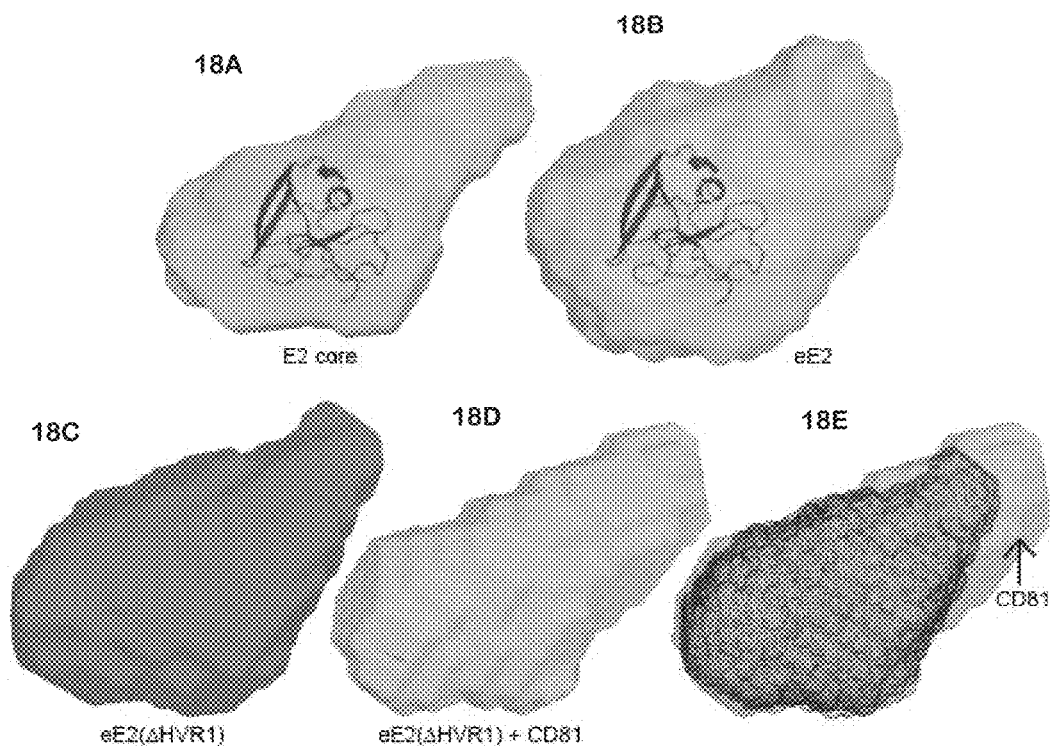
FIG. 18 shows Ab initio SAXS envelopes of E2 core, eE2(DHVR1) and eE2. (A-D) SAXS envelopes of glycosylated E2 core (a), eE2 (b), eE2(DHVR1) (c) and eE2 (DHVR1) in complex with CD81-LEL (d). The E2 core domain structure has been fitted into a and b. (E) Superposition of the SAXS envelopes of eE2(DHVR1) alone (c) and in complex with CD81-LEL (d), highlighting the approximate position of CD81-LEL.
Figure 19:
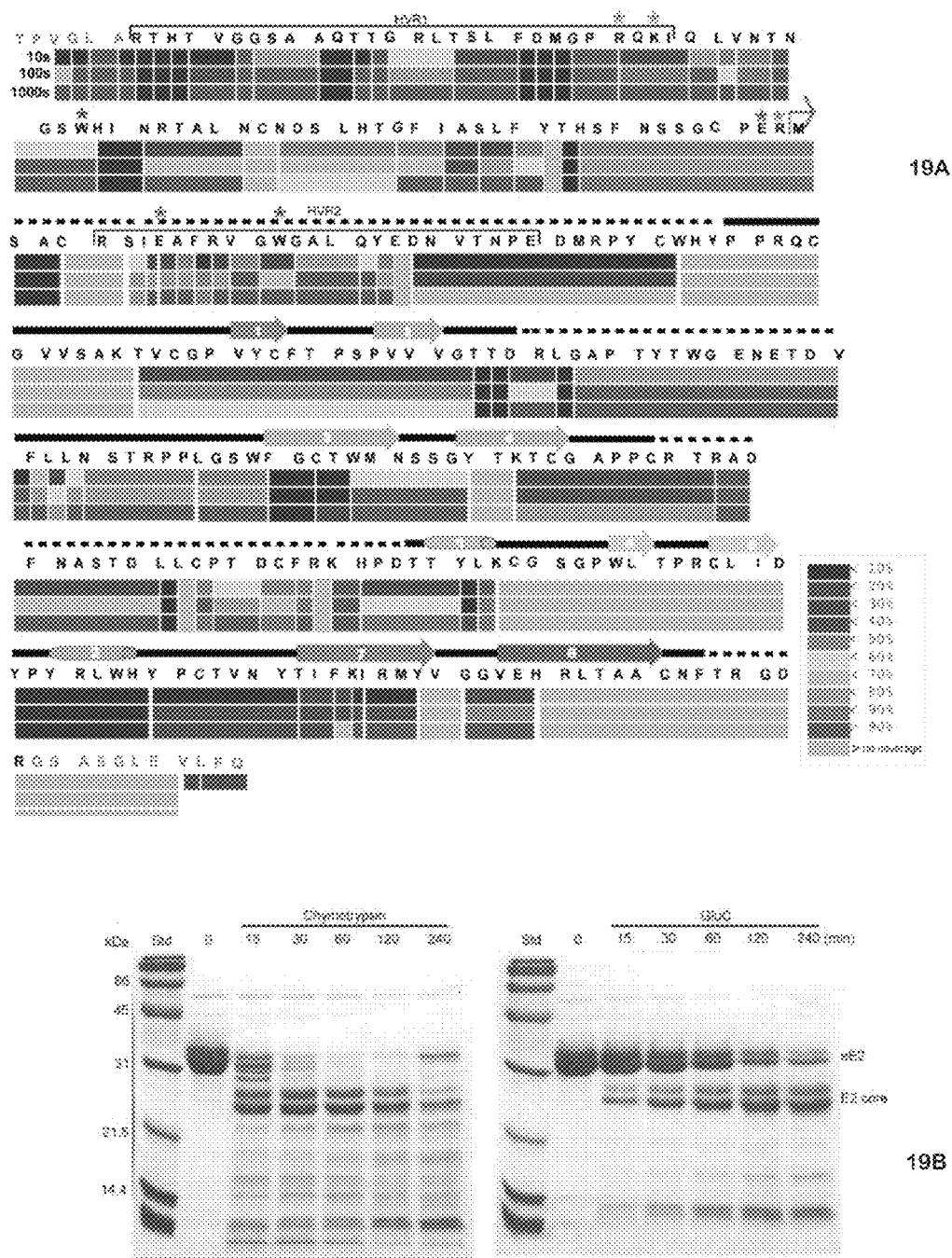
FIG. 19 shows hydrogen deuterium exchange and limited proteolysis of eE2. (A) The percentage hydrogen deuterium exchange shown at 10, 100 and 1,000s time points. The secondary structure of E2 core is placed above to emphasize flexible regions. A red arrow indicates the E2 core N terminus. Extra residues (grey) on N and C termini come from the vector. Potential cleavage sites for trypsin (blue), chymotrypsin (green) and Glue (magenta) are indicated by asterisks. The color pattern indicates the percentage of exchange. Grey areas are the regions of no coverage. (B) Digestion of deglycosylated eE2 with chymotrypsin (left) and Glue (right) reveals a shift from the 35-kDa untreated protein (0 min) to 25 kDa after digestion. Samples were taken at the indicated time points and analyzed by reducing 12% SDS-PAGE gel. Molecular mass protein standards (Std) are indicated. The bands were analyzed by N-terminal sequencing and mass spectrometry.

Solution-based studies using limited proteolysis and hydrogen deuterium exchange demonstrated that approximately 80 amino acids on the N terminus (384-463) from hypervariable region (HVR) 1 through to HVR2 are exposed and flexible. This region includes conserved sequences implicated in binding to the cellular receptors (SR-BI and CD81) as well as several epitopes for neutralizing antibodies (FIG. 16 and FIGS. 18 and 19)[107-111]. Various N-terminal deletions were produced to minimize regions of disorder while preserving an even number of cysteines, potentially allowing for intramolecular disulfide-bond formation. All constructs were screened for aggregation by non-reducing SDS-PAGE and size-exclusion chromatography. The results are described below.

HCV E2 Core

Similar to the flavivirus and pestivirus glycoproteins, the HCV E2 core secondary structure consists of predominantly β-sheets and random coil. However, E2 core is a monomer with a compact globular shape, in contrast to the extended structures reported in other viruses.

The E2 core has a compact, globular domain structure, consisting mostly of β-strands and random coil with two small α-helices. The strands are arranged in two, perpendicular sheets (A and B), which are held together by an extensive hydrophobic core and disulfide bonds. Sheet A has an IgG-like fold that is commonly found in viral and cellular proteins, whereas sheet B represents a novel fold.

Figure 16:
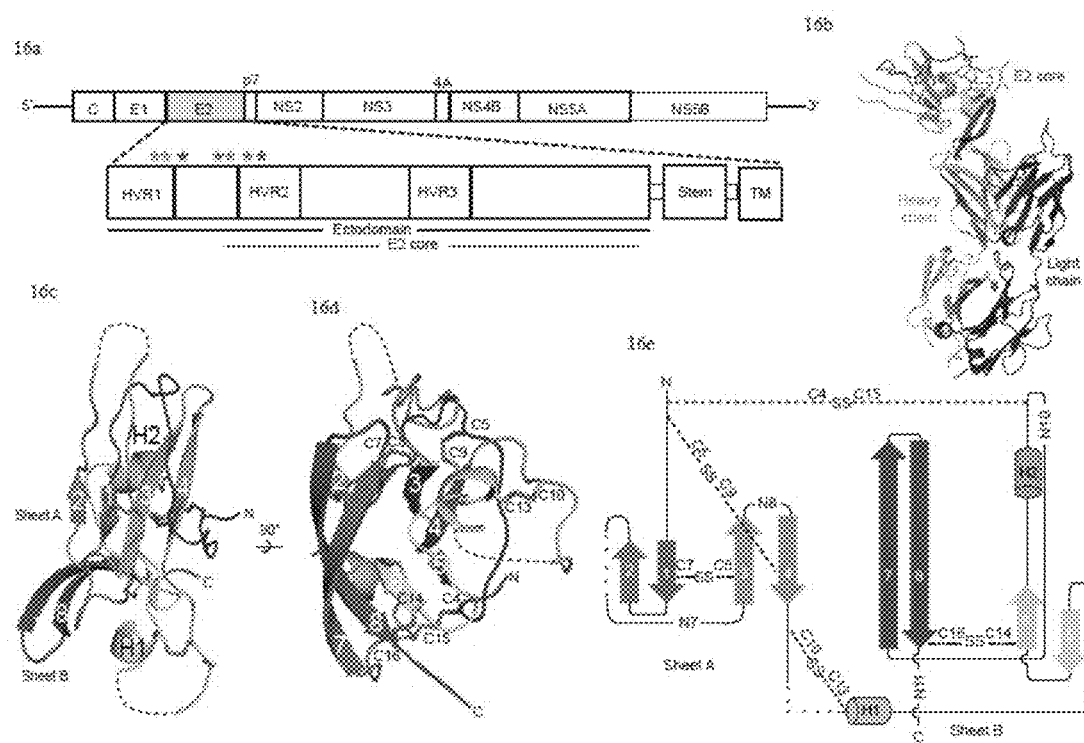
FIG. 16a shows schematic representation of the HCV genome and E2 domain organization. Full-length eE2 and the crystallization construct are indicated by the black and grey bars, respectively. C, capsid protein; non-structural protein (NS) 2-5B. Asterisks indicate the location of trypsin (blue), chymotrypsin (green) and GluC (magenta) cleavage sites.
FIG. 16b-d show ribbon diagram of the E2 core domain bound to Fab 2A12 (b) and alone (c and d). The view in d is a 90° rotation about a horizontal axis from c. The E2 polypeptide chain is colored from the N terminus (blue) to C terminus (red).
FIG. 16e shows topology diagram of E2 core domain, detailing secondary structure elements, disulfide bonds (dashed lines labelled with SS), N-linked glycosylation sites and regions of disordered polypeptide (dotted lines).
Figure 26:
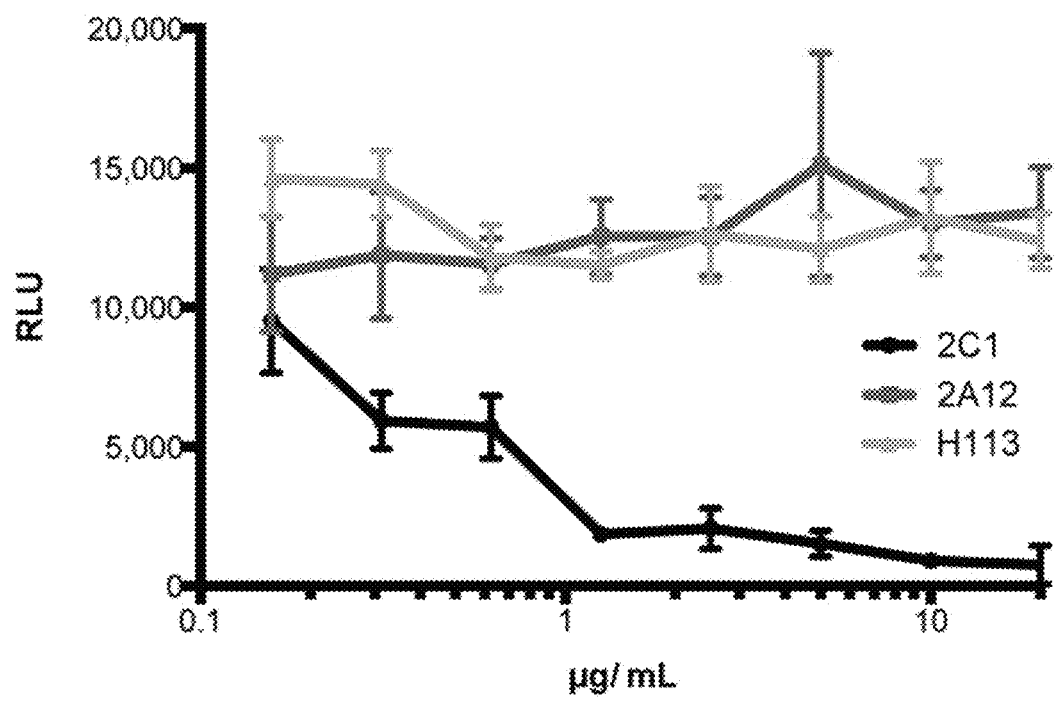
FIG. 26 shows an ELISA. In the ELISA, 2A12 (red), and an irrelevant antibody, H113 (grey), fail to neutralize HCVcc infection. 2Cl (positive control, black), a mouse monoclonal antibody that binds to the disordered N-terminal region of eE2, blocks infection. The measurements were done in triplicate with the error bars representing the s.e.m.
Figure 27:
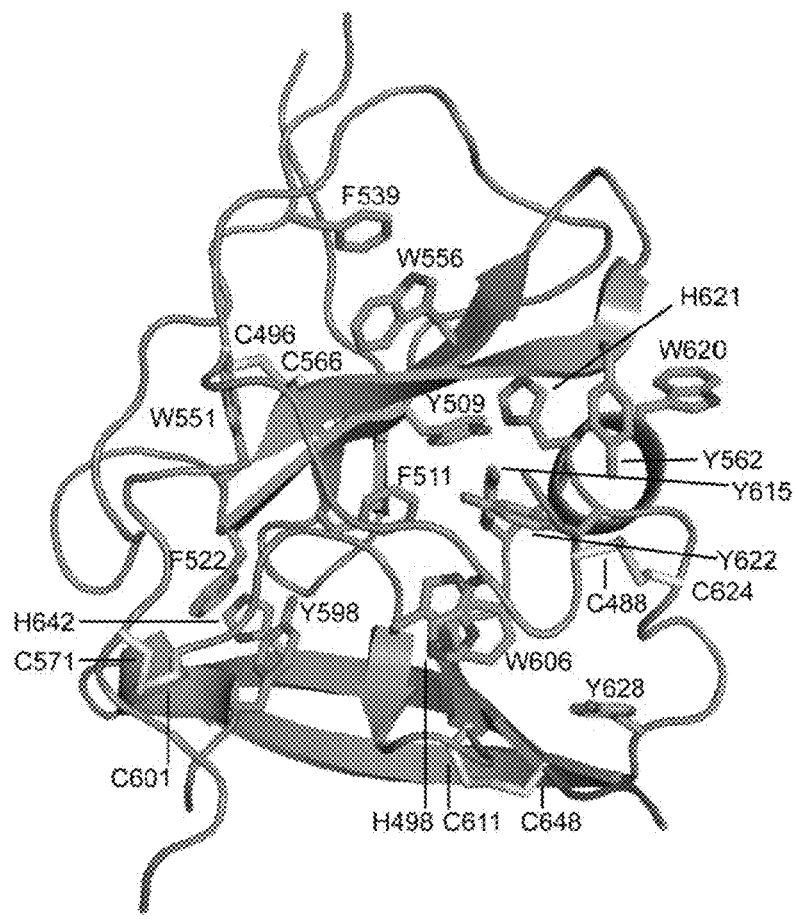
FIG. 27 shows E2 core containing an extensive hydrophobic core. Sheets A and B are held together by an extensive hydrophobic core composed of mostly aromatic amino acids (green) and five disulfide bonds (yellow).

Monoclonal antibodies were generated against recombinant eE2 and crystals of deglycosylated E2 core were produced in complex with a Fab (2A12) and diffracted to 2.4A° resolution (FIG. 16 and FIG. 25). The complex structure was determined by molecular replacement using a Fab structure followed by iterative rounds of model building and refinement, and showed that the E2 core domain has a globular fold, consisting of mostly β-strands and random coil with two short α-helices, which is consistent with previous spectroscopic studies of eE2 (refs 112, 113). The protein contains two, four-stranded antiparallel β-sheets (termed sheets A and B), the planes of which are approximately perpendicular to each other. The four strands of the N-terminal β-sheet (sheet A) are stabilized by two disulfide bonds, between strands 1 and 3 (C7 (510) and C8 (554)) and the N-terminal loop with strand 4 (C5 (496) and C9 (566)). The loop between strands 2 and 3 contains sequences implicated in CD81 binding and is flexible, similar to the N-terminal CD81 binding sites, which were deleted[114,115]. After strand 4, the polypeptide continues into a long, disordered loop before forming the first short helix (H1) followed by the second β-sheet (sheet B). A second short α-helix (H2) is located between strands 6 and 7. A disulfide bond (C14 (611) and C16 (648)) between strand 6 and the C-terminal strand 8 further stabilizes the fold. The C-terminal strands (7 and 8) are the longest within the protein with approximately nine amino acids each and encompass the 2A12-binding site. 2A12 does not neutralize HCV infection, indicating that the epitope is either buried within the particle or incapable of preventing entry (FIG. 26). The two β-sheets are held together by (1) two disulfide bonds, connecting the loops before strand 1 and after H2 (C4 (488) with C15 (624)) as well as the loops after strand 4 and before H1 (C10 (571) and C13 (601)), and (2) an extensive hydrophobic core consisting of numerous aromatic residues (FIG. 27).

Figure 20:
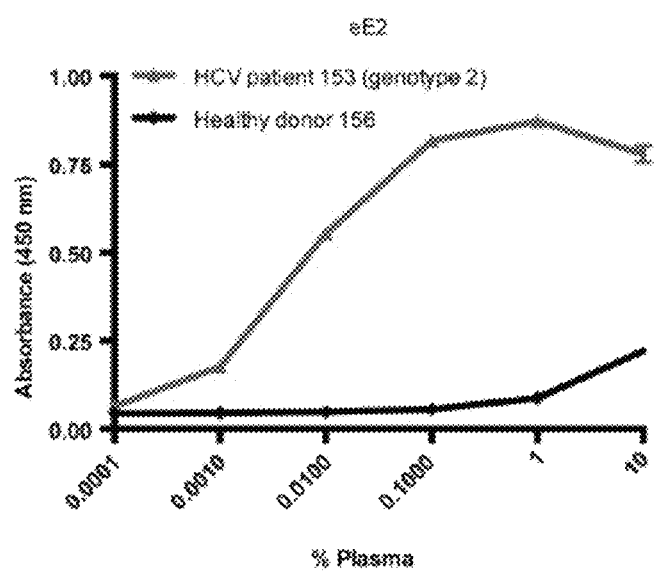
FIG. 20 shows that antibodies from patient sera infected with HCV genotype 2 exhibit concentration-dependent binding to eE2 (red) whereas healthy donor sera exhibit only background binding (black).
Figure 21:
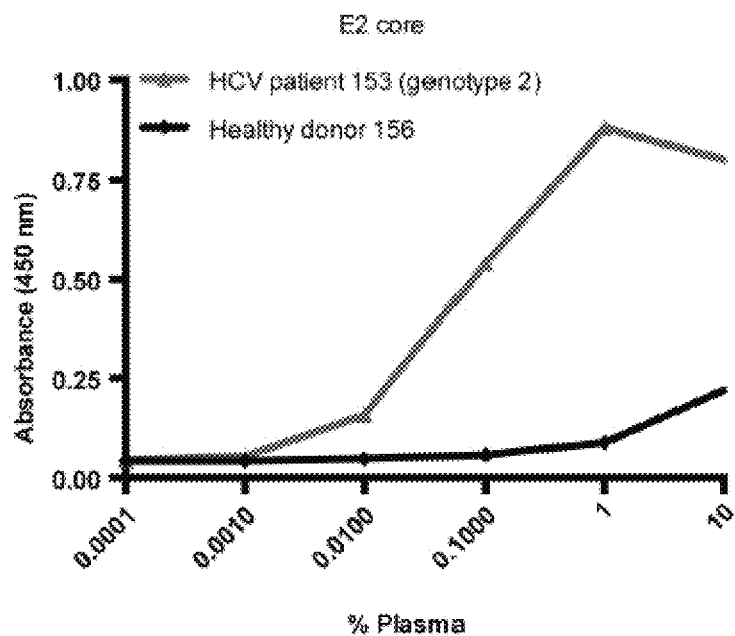
FIG. 21 shows similar binding, as compared to FIG. 20, is observed for E2 core. The measurements were done in triplicate with the error bars representing the standard error of the mean (s.e.m.).
Figure 22:
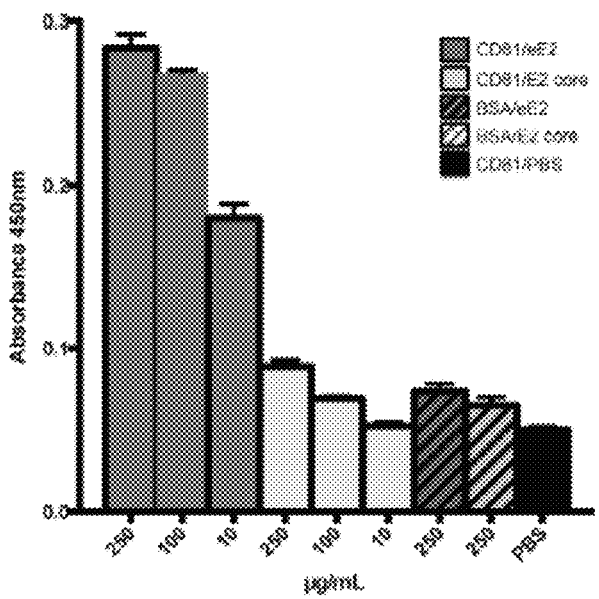
FIG. 22 shows E2 core (light grey) which shows reduced binding to CD81 when compared to eE2 (dark grey) by an ELISA. Bars with stripes indicate E2 binding to a negative control, BSA. The solid black bar indicates CD81 binding to PBS, used to verify the absence of background. The measurements were done in triplicate with the error bars representing the s.e.m.
Figure 23:
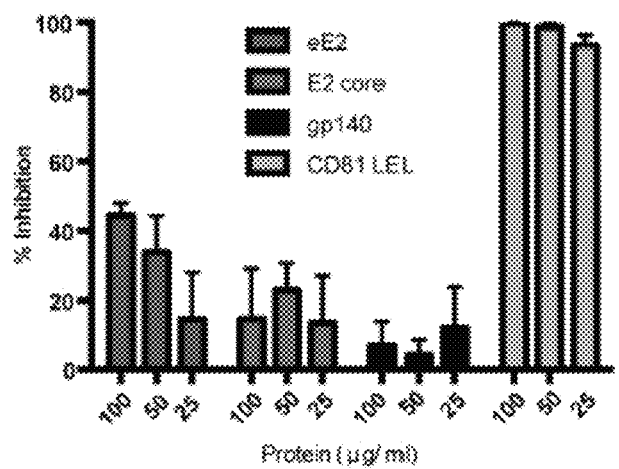
FIG. 23 shows that eE2 (blue) and CD81-LEL (positive control, grey) inhibit the infection. E2 core (red) shows reduced inhibition. HIV gp140 (black) expressed in the same system was used as a negative control. The measurements were done in triplicate with the error bars representing the s.e.m.
Figure 24:
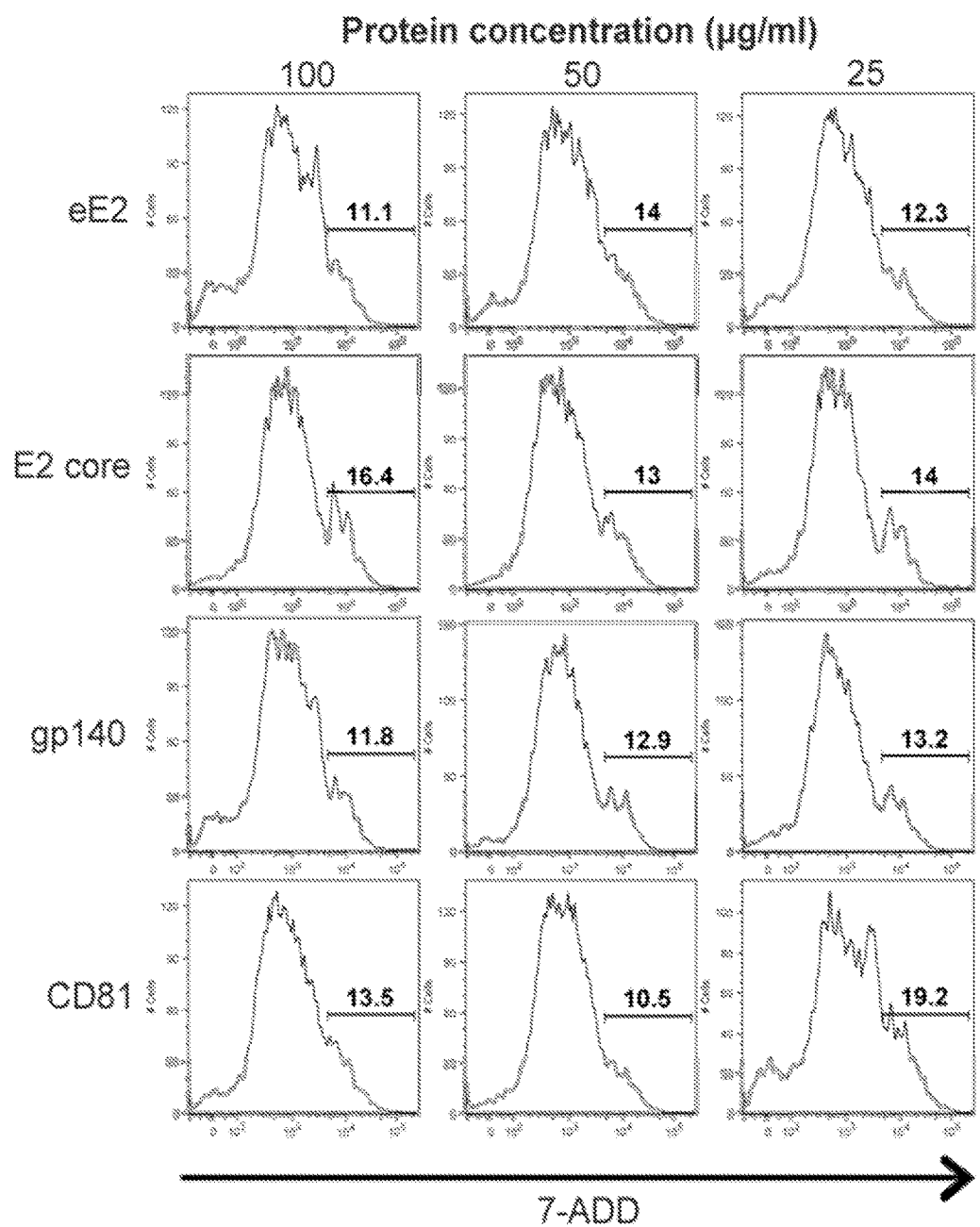
FIG. 24 shows the cell viability measurements as described in Example 21, using similar protein concentrations as in d. This was done to rule out the possibility of toxic effects from the recombinant proteins.

E2 core (456-656) is soluble, monomeric and maintains similar secondary structure content when compared with eE2 as determined by reactivity towards HCV infected patient sera (FIG. 20 and FIG. 21) and circular dichroism (data not shown). However, in contrast to eE2, CD81 binding affinity and the efficiency of inhibition of HCV cell culture (HCVcc) entry was diminished for the E2 core (FIGS. 22-23). This indicates that the N terminus of eE2 is critical for CD81 interaction and probably undergoes a transition from disorder to order on binding. Alternatively, the N-terminal region may also be ordered through interactions with other factors, for example, E1, apolipoproteins, lipids, cellular receptors, or antibodies.

Figure 29:
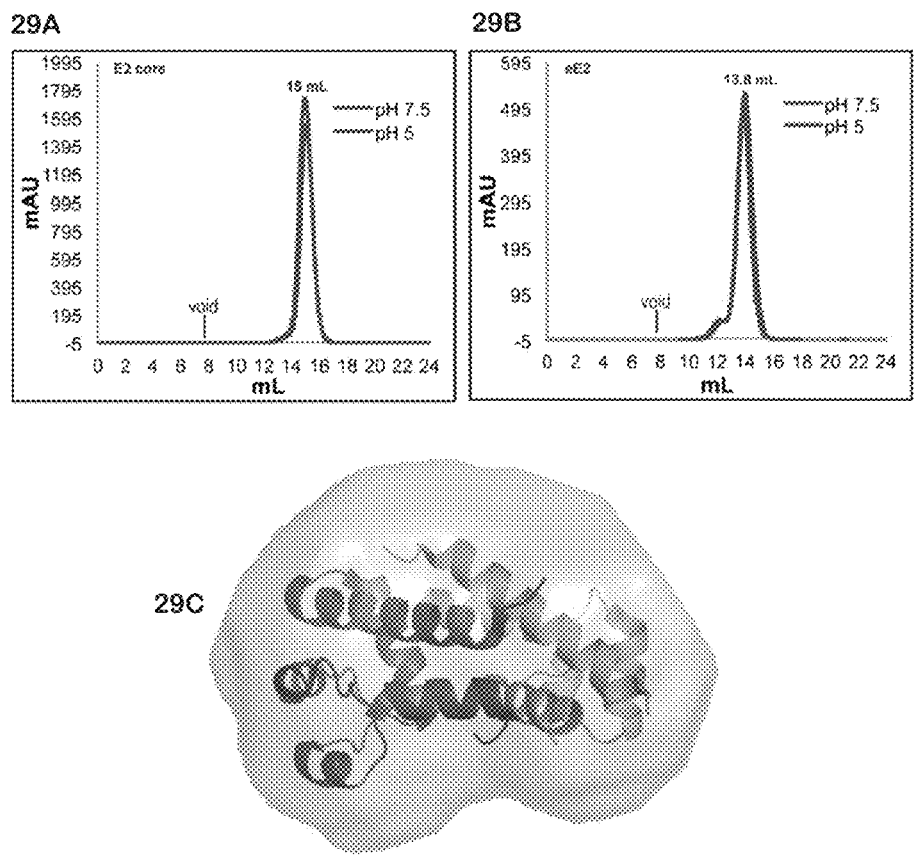
FIG. 29a-29c show that eE2 and E2 core do not undergo oligomeric changes at low pH. (A and B).

The ab initio SAXS envelopes of E2 core and eE2 are similar, with approximately the same radius of gyration ($R_g$) (FIGS. 18a-18b). Glycosylation, which is missing in the E2 core crystal structure, represents roughly one-third of the mass and accounts for the unmodelled areas of the envelopes. Notably, neither the $R_g$ nor the elution profiles on size-exclusion chromatography for fully glycosylated eE2 and E2 core changes significantly at pH5.0 (FIG. 29a and FIG. 29b). These results indicate that unlike class II membrane fusion proteins, E2 does not undergo significant structural rearrangements on exposure to low pH.

Solution-based studies demonstrate that the full-length E2 ectodomain has a similar globular architecture and does not undergo significant conformational or oligomeric rearrangements on exposure to low pH. Thus, the IgG-like fold is the only feature that E2 shares with class II membrane fusion proteins. These results provide unprecedented insights into HCV entry and assists, e.g., with developing an HCV vaccine and new HCV inhibitors.

Structural comparison of the HCV E2 core domain with all known folds in the Protein Data Bank using the Dali server 25 identified proteins with IgG-like folds similar to the N-terminal sheet A, none of which is a class II fusion protein, although IgG-like folds are common in these proteins. The server failed to identify any statistically significant structures to sheet B, suggesting a novel fold.

Subsequent to the present invention, a structure for HCV E2 from genotype 1a was reported[126]. The core domain of reported structure and the structure described herein is highly similar with a root mean squared deviation of 0.8 Å for similar carbon atoms.

Biochemical and structural data disclosed herein provide valuable information towards defining the role of E2 and establish a foundation for further studies in understanding HCV entry and infection.

CD81 Binding Region

SAXS was used to investigate the CD81 binding region on the E2 ectodomain. To simplify data interpretation, eE2 (DHVR1) was used, as HCV lacking HVR1 remains infectious[121]. The binding site of CD81 was identified by superimposing the SAXS envelopes of eE2(DHVR1) alone and in complex with CD81-LEL (FIG. 18c-e). Although CD81-LEL is a dimer in solution (FIG. 29c), the extra density in the SAXS envelope is more consistent with monomeric binding; however, a dimer cannot be ruled out.

Construct Design, Expression and Purification of HCV eE2

HCV E2 is a type I transmembrane protein with an amino-terminal ectodomain and a carboxy-terminal membrane-associating region. The protein is composed of 333 residues. E2 is glycosylated and contains intramolecular disulfide bonds, making it extremely challenging for structural, biochemical, and biophysical studies. However, we use E2 ectodomain (eE2) (amino acids 384-660 of the HCV polyprotein genotype 1a starting from position 1 in the HCV core and/or amino acids 384-664 of the HCV polyprotein genotype 2a) that is lacking the C-terminal membrane anchor, since this has been demonstrated to express well[11] and retain interactions with CD81 and SR-BI.

Biochemical, biophysical, and structural studies rely on the production of purified eE2. Studies on recombinant E1 and E2 expression have yielded two different forms of the molecules: a glycosylated protein with intramolecular disulfide bonds that is believed to be the active form and high molecular weight aggregates caused by intermolecular disulfide bonds. The formation of disulfide bonded aggregates and misfolded protein has hampered structural and biophysical studies on the HCV glycoproteins. Our approach was to explore three different variables (cell type, genotype and affinity tag) to determine which construct produced high levels of properly folded eE2.

Cell Type

The cell lines used for expression can have a pronounced effect on stability. Expression of viral glycoproteins in bacteria has proven to be a challenge and several reports document that expression of eE2 in *E. coli* leads to the formation of insoluble, inclusion bodies. This is not surprising given the large number of potential glycosylation sites and intramolecular disulfide bonds. Proteins with these posttranslational modifications are known to be difficult to express in bacteria. The unique properties of the mammalian cellular environment make this the ideal choice for homologous expression of eE2. HEK293T and Huh7 cells were the first cell lines tested, since these have been shown to produce active E1 and E2 in the form of HCVpp and HCVcc. Initially, HEK293T were chosen over Huh7 owing to ease of handling, robust growth rate, excellent transfectability, and high capacity for recombinant protein expression.

Genotype

Given that E2 forms the virus particle, the surface of the glycoproteins would be expected to undergo mutation to escape immune pressure; therefore the behavior of E2 from different genotypes might be markedly different. In fact, it has been shown that preparations of E2 from different genotypes can vary in binding to CD81 and the aggregation state of the glycoproteins. This approach of expressing the same protein from different genotypes was essential to defining constructs that would yield the highest amount of folded protein for functional studies. In fact the same protein from different genotypes behaved differently in terms of amount expressed, solubility and protein stability.

Affinity Tag

Protein tags are peptide sequences genetically grafted onto a recombinant protein. Often these tags are removable by chemical agents or by enzymatic means, such as proteolysis or intein splicing.

Tags are attached to proteins for various purposes. For example, affinity tags may be appended to proteins so that they can be purified from their crude biological source using an affinity technique.

The methods of the invention may or may not include an affinity tag. The affinity tag may, e.g., comprise Fc domain of human IgG or a protein-A.

In certain embodiments, protein-A is used as an affinity tag. Protein A is a surface protein of *S. aureus* which binds IgG molecules through the Fc region.

In certain embodiments, the addition of an affinity tag can permit rapid purification and added protein stability. In previous work relating to the expression and purification of eE2, a construct consisting of the E1 signal sequence followed by the ectodomain of E2 and a C-terminal, six histidine tag was made and expressed in HEK293T cells. The signal sequence would target eE2 to the ER where glycosylation and disulfide formation occur naturally and permit the protein to be secreted into the media. Expression levels were very low and supernatants stripped the Ni from the resin, resulting in poor retention of the eE2. Buffer exchange of the media inhibited the Ni stripping while promoting eE2 binding, however this approach would not be applicable for large-scale expression. Therefore, a better tag was needed which had high affinity and specificity to a resin, and could be used in the presence of media.

We sought to use the Fc domain of human IgG as an affinity tag. The Fc domain is glycosylated, contains an intermolecular disulfide bond, is very soluble, binds with high affinity to protein A resin, and can bind to the resin in the presence of tissue culture media. Our hypothesis was that since the Fc domain is glycosylated and disulfide bonded it might assist similar modifications found on eE2 and only a properly folded Fc domain is competent for secretion and protein A binding. These unique properties of the Fc domain seemed ideal for this situation.

The HCV eE2 was cloned as a fusion with the Fc domain into a modified pcDNA3.1 vector for constitutive expression in mammalian cell lines. A schematic representation of the expression construct is shown in FIG. 2. Amino-terminal to the gene of interest is the prolactin signal sequence that targets the ectodomains to the endoplasmic reticulum followed by a short linker region to allow for efficient cleavage by signal peptidase. On the carboxy-terminus is a thrombin cleavage site followed by the Fc domain to facilitate protein purification. The Fc domain construct contains several natural introns, which has been shown to increase protein expression by several fold. Initially, we constructed eE2 from genotypes 1a (H77) (amino acids 384-661) and 2a (J6) (amino acids 384-664) into the plasmids described above and expressed in HEK293T cells. The discrepancy between the numbers is due to a small insertion into HVR2 region in J6. These two genotypes were chosen since they have been demonstrated to be infectious in chimpanzees. The constructs were transiently transfected into HEK293T cells. Seventy-two hours posttransfection the cells and supernatants were harvested, separated by reducing (FIG. 3A) and nonreducing SDS-PAGE (FIG. 3C), and probed with anti-human Fc antibodies. Prolactin was used as a control and the ectodomain of HCV E1 was also expressed in this system. The E1 and E2 ectodomains yielded good expression levels without the production of disulfide-bonded aggregates, as determined by reducing and nonreducing SDS-PAGE (FIG. 3). For the E1 ectodomain the cell lysates contain six bands, which we believe correspond to 0-5 glycosylation events (FIG. 3B). This result is consistent with the prediction that eE1 contains 4 glycosylation sites and the Fc an additional site. The eE1 supernatants contain only a single band that migrates slightly slower than the top band seen in the cell lysate, suggesting that the eE1-Fc fusion has been fully processed and secreted through the secretory pathway. This result supports our hypothesis that the Fc domain might promote protein modification and secretion. When the identical samples were analyzed under nonreducing SDS-PAGE (FIG. 3C), the cell lysates from all constructs contain a faster and slower migrating band relative to the reduced form (compare similar lanes in FIGS. 3A and 3C). The Fc tag is an intermolecular, disulfide-bonded dimer while the HCV glycoproteins contain intramolecular, disulfide bonds. Therefore, the faster migrating band corresponds to a monomeric protein with intramolecular disulfide bonds, while the slower migrating band is a dimer stabilized by the intermolecular disulfide bond in the Fc tag. The slower migrating band is approximately double the molecular weight of the reduced form consistent with an intermolecular disulfide bond between two Fc molecules. Only the slower migrating band is present in the supernatant of the cells transfected with the HCV glycoproteins, suggesting that only those proteins with a fully formed Fc dimer are secreted. The supernatants from the prolactin control cells do show both bands. However, this could be due to the noticeable cell death that occurred with that population. The presence of the disulfide-bonded homodimer in supernatant supports our hypothesis that only a properly folded Fc domain can be secreted.

Encouraged by our preliminary expression results, we attempted to produce a stable cell line that constitutively secreted eE2. HEK293T cells were transfected with eE2 constructs from both genotypes and were placed under hygromycin B selection. We developed a quantitative enzyme-linked immunosorbent assay (ELISA) against the Fc domain to quickly identify and quantitate which drug resistant cells were expressing the most eE2. We have isolated HEK293T cells that constitutively express eE2 from J6 and H77 at levels comparable to transient transfection.

Figure 4:
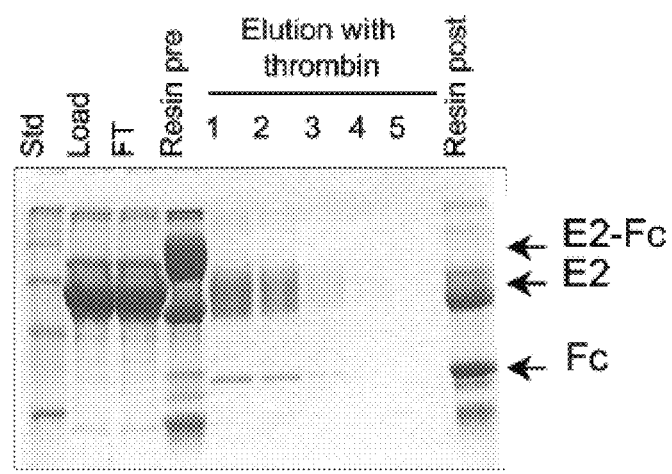
FIG. 4. shows purification of E2-Fc over protein A resin. Supernatants from cell lines expressing E2-Fc are clarified by centrifugation (load) and applied to the resin. After incubation, the column is extensively washed to remove unbound material (FT). E2 is eluted off the column in five fractions (1-5) by incubation with thrombin protease. The resin before (pre) and after (post) elution are also shown. Samples are analyzed by SDS-PAGE and stained with coomassie Blue.

With the creation of a stable cell line expressing eE2, we set out to determine purification conditions. The stable eE2 cell lines were expanded into 10 roller bottles with media containing fetal bovine serum to assist in cell attachment and growth. Once the cells become confluent, the supernatant is harvested, replaced with media without serum, and left for another two days. The media from both harvests is pooled together (approximately 1 L total volume) and incubated in the presence of protein A resin with agitation overnight in a cold room. The next morning the resin is harvested and washed extensively with buffer. The fusion protein can be eluted off the resin by either the addition of thrombin to cleave between eE2 and the Fc or by lowering the pH of elution buffer to disrupt the Fc/protein-A interaction. Since HCV and other viruses undergo a low pH triggered membrane fusion, eluting eE2 by low pH may cause a structural rearrangement in the glycoproteins. The resin can be washed with buffer to collect eE2, leaving the contaminants bound to the resin. Samples (5 µL) of each step of the purification are analyzed by SDS-PAGE and stained with Coomassie blue protein dye (FIG. 4). The presence of J6 eE2 was confirmed by a combination of N-terminal sequencing and tryptic digestion followed by mass spectrometry. The final protein yield is about 0.5-1 mg of eE2 per liter of supernatant in one preferred embodiment, in other embodiments, the yield is about 2 mg/liter, in other embodiments, the yield is about 4 mg/liter and in still other embodiments, the yield is about 15 mg/liter.

Properties of J6 eE2 Glycosylation

Figure 5:
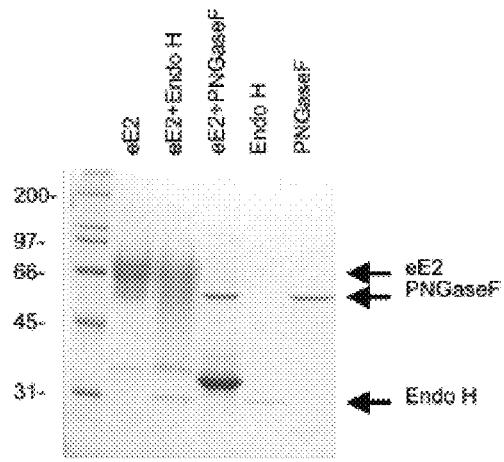
FIG. 5. shows deglycosylation of eE2 with PNGaseF and Endo H. Purified eE2 was deglycosylated with PNGase F or Endo H under denaturing and reducing conditions and analyzed by SDS-PAGE. The position of the enzymes is also shown.

The addition and modification of glycans onto proteins is one of the major biosynthetic pathways found in the lumen of the ER. During translation of a glycoprotein, an oligosaccharide composed of two N-acetylglucosamine, nine mannose, and three glucose molecules are transferred en bloc to a sequon of Asn-X-Ser/Thr (where X is any amino acid except Pro). Oligosaccharyl transferase (also known as N-acetylglucosaminyltransferase), is an ER membrane bound enzyme that characterizes the transfer to the $NH_2$ group of the Asn side chain. However, not every sequon is modified and the efficiency of transfer can vary for the same sequon, leading to a mixture of modified and unmodified protein. Once the oligosaccharide is on the protein, it can be trimmed and further glycans added as the protein travels through the ER and Golgi apparatus. The processing pathway is highly ordered and begins in the ER with the removal of all the glucose and certain mannose molecules. The remaining steps occur in the Golgi apparatus, where three more mannose molecules are removed and various sugars are added. Although the steps of processing and subsequent sugar addition are rigidly ordered, complex oligosaccharides can be heterogeneous. The end result is two broad classes of N-linked oligosaccharides, referred to as complex and high mannose oligosaccharides. Whether a given oligosaccharide remains high-mannose or is processed is largely determined by its configuration on the protein and if the site is accessible to the modifying enzymes. High mannose and complex oligosaccharides can be differentiated by endoglycosidase H (Endo H) sensitivity, since Endo H will only cleave high mannose glycans. Peptide-N-glycosidase F (PNGase F) will remove all types of N-linked glycosylation. eE2 appears as a smeary band by reducing SDS-PAGE (FIG. 4), which is consistent with what is seen with other glycosylated proteins. To confirm that the eE2 is glycosylated, the protein was denatured in the presence of SDS and reducing agent (dithiothreitol DTT), and incubated with endoglycosidases, Endo H or PNGase F (FIG. 5). PNGase F collapses the protein from 66 kDa to about 35 kDa. Each glycosylation event would increase the protein's molecular weight by about 2-2.5 kDa. The difference in molecular weight seen in the presence and absence of PNGase F can be explained if all 11 putative glycosylation sites are modified, resulting in an increase of approximately 22-27.5 kDa. Since eE2 is expressed by secretion into the media, the glycans would be predicted to be complex carbohydrates and insensitive to Endo H digestion. FIG. 5 documents that eE2 is mostly insensitive to Endo H treatment, consistent with its mode of expression.

Disulfide Bond Formation and Aggregation

Figure 3:
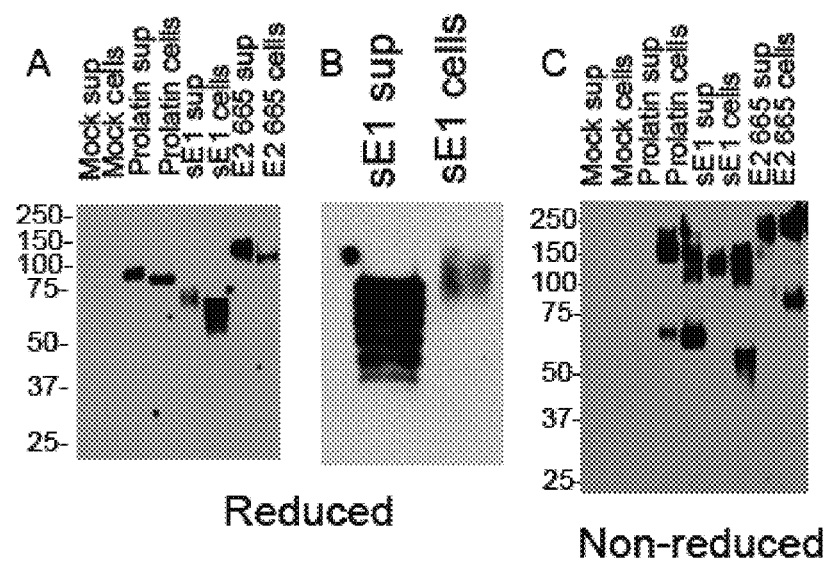
FIG. 3. shows expression of the HCV E1 and E2 ectodomains. C-terminal truncations of E1 and E2 were cloned into the mammalian prolactin Fc expression vector and transfected into HEK293T cells. The truncation of each protein relative to the translation start site in core is shown. Supernatants and cells were harvested 72 hours post transfection, separated by reducing (A) and nonreducing (C) SDS-PAGE, transferred to nitrocellulose and probed with an antibody against human Fc. Prolactin was used as a control for protein expression. Panel B is an enlargement of the E1 samples from the reducing gel (A). The cell lysate contains 6 bands, which correspond to basal and 5 additional glycosylation events, while the supernatant contains only the top band.
Figure 6:
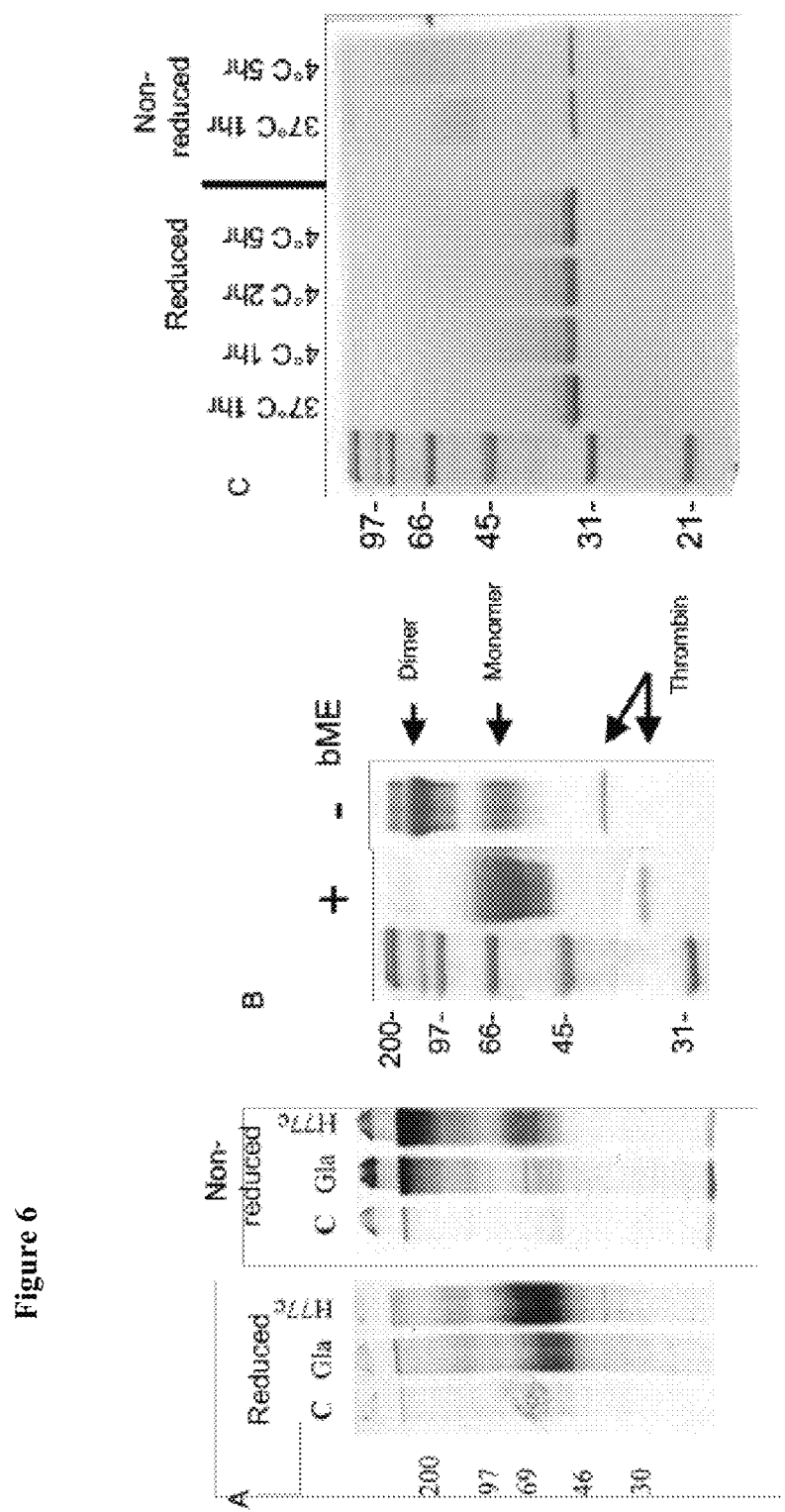
FIG. 6. shows reducing and non-reducing SDS-PAGE. (A) BHK cells were infected with the wild-type (wt) vaccinia virus strain WR, or recombinant vaccinia viruses expressing eE2 from two HCV strains (Gla or H77), in the presence of [35S]methionine. The radiolabelled proteins from the medium were immunoprecipitated, subjected to 10% SDS-PAGE under reducing and non-reducing conditions. (Image taken from FIG. 3 of Patel et al. 12.) (B) SDS-PAGE of our purified eE2 in the presence and absence of reducing agent and stained with coomassie blue. The samples were run on the same gel with several empty lanes as to prevent reducing agent spread during running. The intervening lanes are not shown for the sake of saving space. (C) Deglycosylation of eE2 with PNGase F under nondenaturing conditions without reducing agent. The time and incubation temperature is given above. Identical samples were analyzed on SDS-PAGE in the presence and absence of reducing agent and stained with Coomassie blue.
Figure 7:
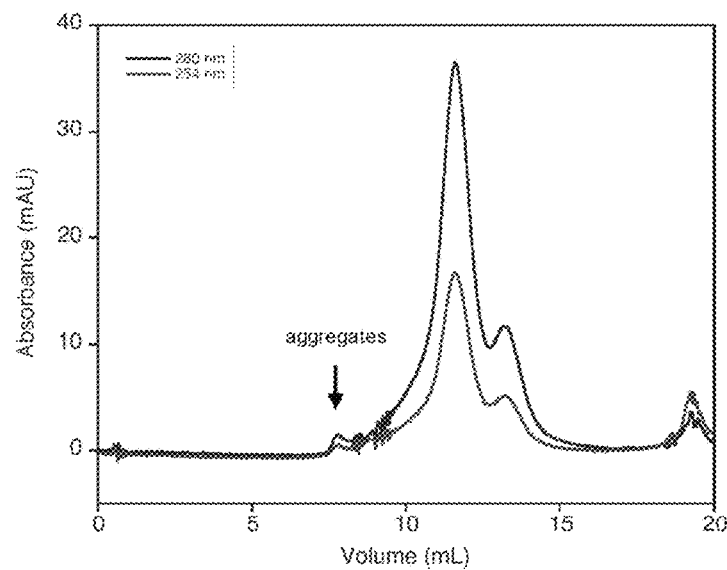
FIG. 7. Oligomeric state of eE2. (A) Purified eE2 was applied to Superdex 200 size exclusion column. The arrow denotes void volume where proteins larger than 200 kDa would be expected to elute. The blue (taller peak) and red (shorter peak) lines represent the absorption at 280 and 254 nm, respectively. (B) Enzyme-linked immunoassay for CD81 LEL binding. Tissue culture supernatants of eE2-Fc fusion (no dilution, 1:10 and 1:100 dilutions) were incubated in plates coated with either GST, GST-mouse CD81 LEL, or GST-human CD81 LEL. After washing, bound eE2-Fc was detected with anti-human Fc-HRP. PBS, media from wt HEK293T cells and wells without any coating were used as controls.
Figure 7:
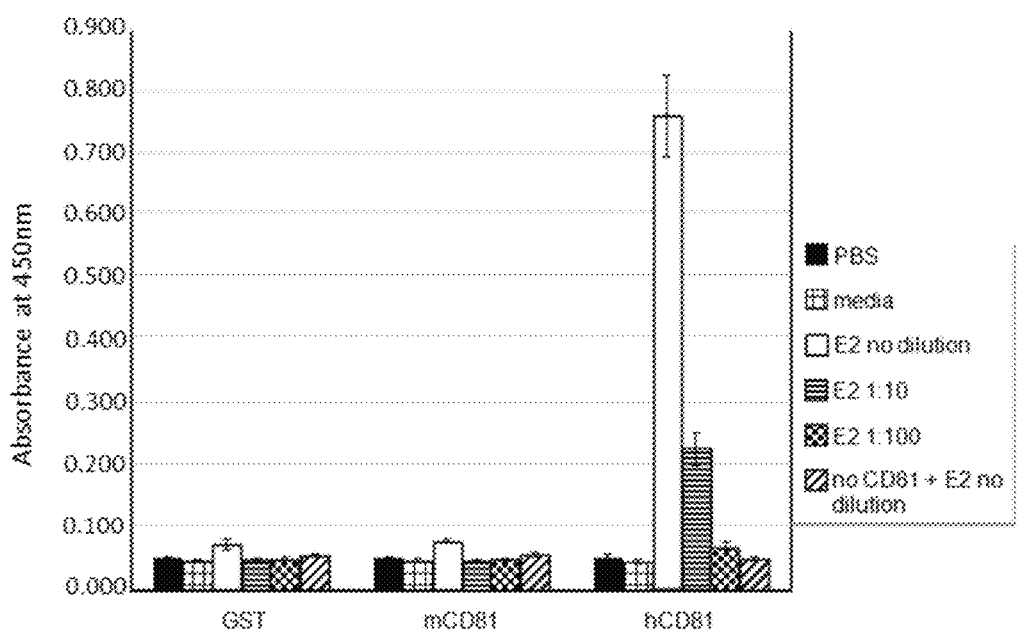
Figures 8A, 8B:
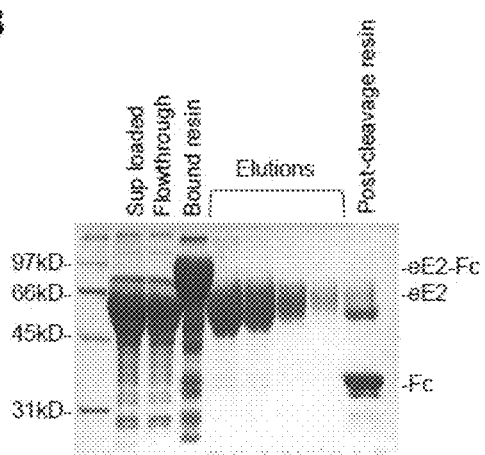
FIG. 8. (A) Is the sequence of J6 eE2 (residues 384-664) (SEQ ID NO. 1) highlighting the conserved cysteine residues (underlined), and the potential N-linked (Bold) and O-linked (Italics) glycosylation sites. (B) Shows purification of eE2-Fc over protein A-sepharose. Supernatants from cell lines expressing eE2-Fc are clarified by centrifugation (sup loaded) and applied to the resin. After incubation, the column is extensively washed to remove unbound material (flowthrough). E2 is eluted off the column in five fractions (elutions 1-5) by incubation with thrombin protease. The resin before (bound resin) and after elution are also shown (post-cleavage resin). Samples are analyzed by SDS-PAGE and stained with Coomassie blue.
Figure 9A:
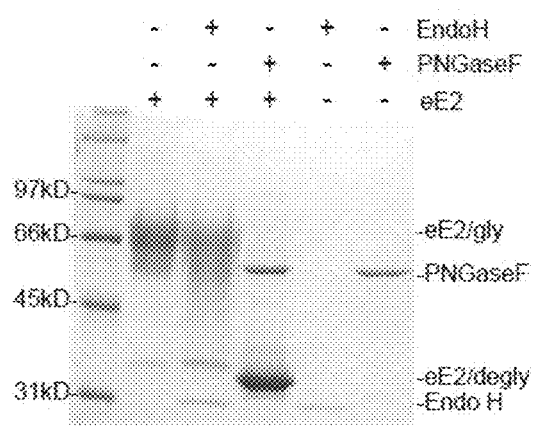
FIG. 9. (A) Shows deglycosylation of eE2 with PNGase F and Endo H. Purified eE2 was deglycosylated with PNGase F or Endo H under denaturing and reducing conditions and analyzed by SDS-PAGE. The position of the enzymes and eE2 are also shown. (B) Shows mapping the N-linked glycosylation sites. The ten panels contain LC-MS data, corresponding to the peptides containing the 11 N-linked glycosylation sites: N417 (SEQ ID NO. 2), N423/430 (SEQ ID No. 3), N448 (SEQ ID No. 4), N477 (SEQ ID No. 5), N534 (SEQ ID No. 6), N542 (SEQ ID. No. 7), N558 (SEQ ID No. 8), N578 (SEQ ID No. 9), N627 (SEQ ID No. 10), and N649 (SEQ ID No. 11). Note that one peptide contains two glycosylation sites. The top spectra are for glycosylated peptides, while the bottom spectra are for peptides deglycosylated with PNGase F. The height of the peak corresponds to relative abundance. The peptide sequence and measured molecular weights are given.
Figure 9B:
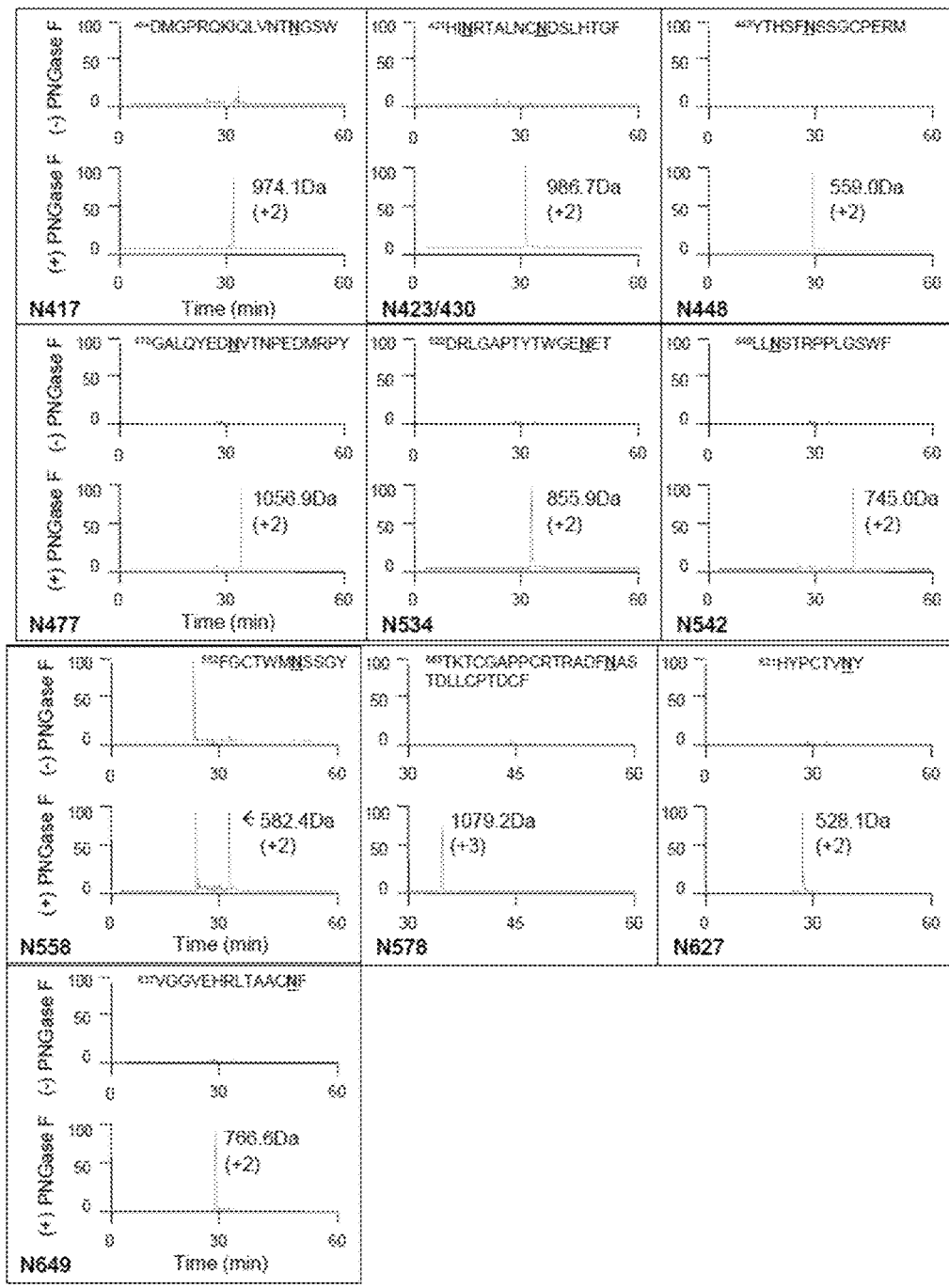
Figure 13:
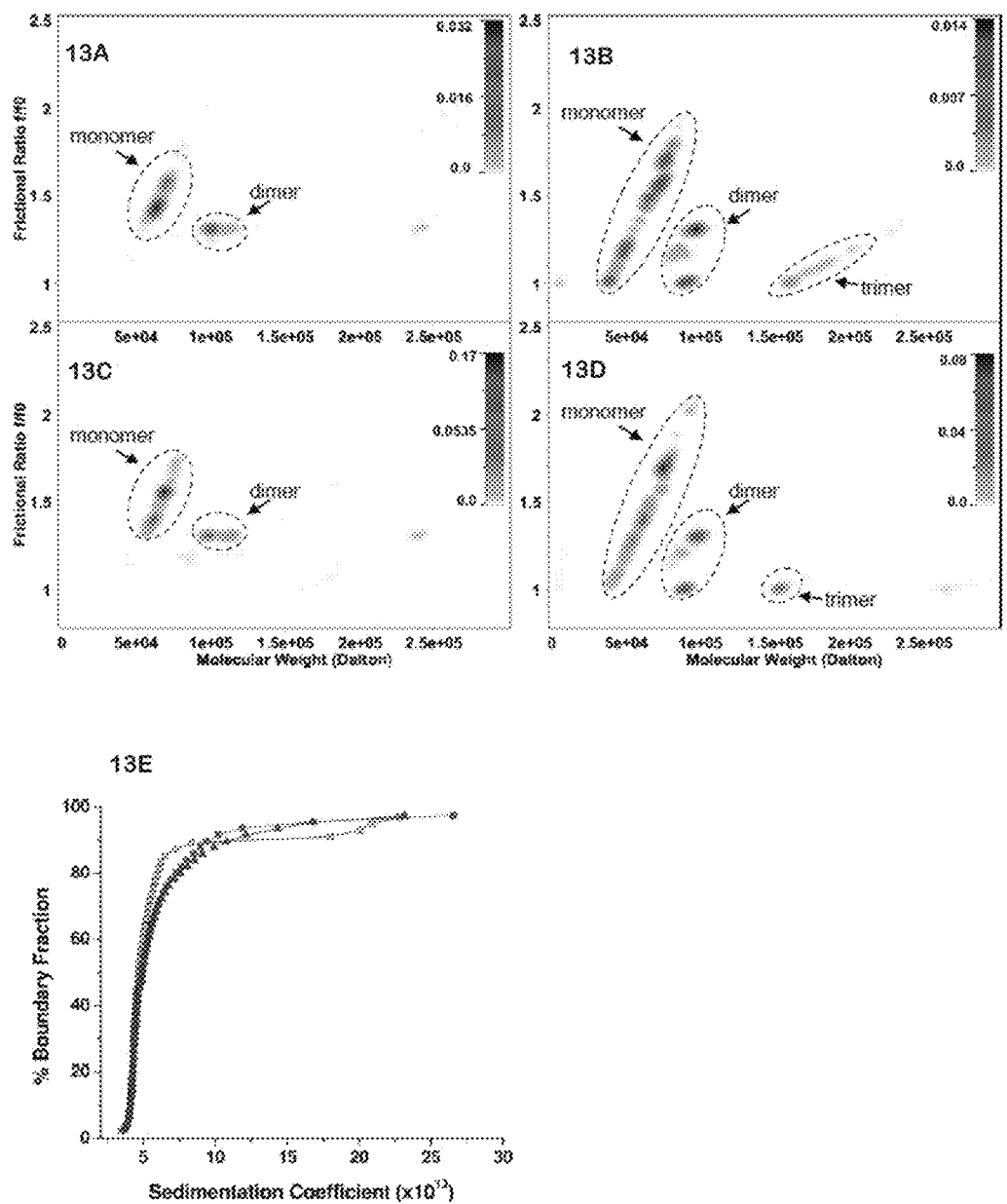
FIG. 13. Shows analytical ultracentrifugation data for eE2-C656S at pH7 and pH5. Two-dimensional spectrum/Monte Carlo analysis of HCN sedimentation velocity data. Measurements of eE2 were made at low concentration (0.25 $OD_{230}$) at pH 5 (A) and (pH 7) (B), and at higher concentration (0.8 $OD_{230}$) at pH 5 (C) and pH 7 (D). All samples show the presence of monomer and dimer. The pH 7 samples show the presence of a trimer species. Heterogeneity in shape and molecular weight is more prominent in the pH 7 samples for both monomer and dimer species. Larger species appear more globular than smaller species according to the frictional coefficients. The units of the color gradient are in $OD_{230}$. (E) Integral van Holde-Weischet distributions from sedimentation velocity experiments with HCV to test pH reversibility. Shown is the distribution for HCV at pH 5 (grey squares), at pH 7 (blue triangles) and at pH 7 after buffer exchange from pH 7 to pH 5, and then back pH 7 (red circles). The distributions all show about 10% high-molecular weight aggregate, as well as about 50% of the protein sedimenting at the same speed. The remaining 40% of the protein sediments slightly faster for samples at pH 7, indicating the presence of higher molecular weight species. Importantly, the sample which has undergone dialysis from pH 7 to pH 5 and then back to pH 7 shows that most of the material has reverted back to the distribution seen for the pH 7 sample that was never exposed to pH 5.

As mentioned previously, expression of HCV eE2 has resulted in the formation of high molecular weight aggregates caused by the presence of intermolecular disulfide bonds that are considered to be misfolded. FIG. 6A displays what is commonly seen for eE2 expression in the presence and absence of reducing agent (image taken from FIG. 3 of Reference 12). Nonreducing SDS-PAGE demonstrated that our purified, glycosylated eE2 was mostly dimer and monomer with higher order aggregates to a lesser extent. Our result is in contrast to what has been published previously, which has shown the E2 is mostly monomer and high molecular weight aggregate under non-reducing conditions (compare FIGS. 6A and 6B). The smeary nature of eE2 made molecular weight determination difficult. So we decided to deglycosylate eE2 with PNGase F under native conditions and then analyze the product by nonreducing, SDS-PAGE, which would allow for sharper bands and better MW estimations (FIG. 6c). Surprisingly, the natively deglycosylated protein appears to be monomeric by nonreducing SDS-PAGE. We confirmed that the PNGase F preparation was purified in the absence of any reducing agent (New England BioLabs). To further characterize the oligomeric state of glycosylated eE2, the protein was subjected to gel filtration chromatography (Superdex 200 column, GE Healthcare) (FIG. 7A). eE2 appears mostly as a single species (estimated to be 75% by peak area) with a smaller second peak as a shoulder after the main peak. There is an extremely small peak in the column void volume, which would represent aggregates with MW greater than 200 kDa (denoted with an arrow). Proteins of defined MW were applied to the gel filtration column under identical buffer conditions and the MWs of the two main peaks were calculated to be 123 kDa and 75 kDa. These MWs would be consistent with a dimer and monomer, assuming that the fully deglycosylated monomer is less than 66 kDa (as determined by SDS-PAGE). There is a striking similarity between the ratio of dimer to monomer in the gel filtration data and in non-reduced SDS-PAGE. eE2 has 17 highly conserved cysteine residues, which could result in the formation of eight disulfide bonds. It is possible that in the absence of reducing agent the protein does not completely unfold and some structure remains in non-reducing SDS-PAGE. It has been shown that aggregated eE2 will not bind to CD81[12]. We performed an enzyme-linked immunoassay to test binding of eE2 to the LEL from mouse and human CD81 (FIG. 7B). The supernatants from our HEK293T cells that express eE2 showed strong and specific binding to only human CD81 and almost no binding to mouse CD81. This species-specific binding to CD81 is consistent with what has been seen previously[5].

DESCRIPTION OF PREFERRED EMBODIMENTS

The following examples are meant to illustrate, but not limit the scope of the invention.

Example 1

Production of eE2 Stable Cell Lines

HEK293T cells were cultured in Dulbecco's Modified Eagle Medium supplemented with 10% FBS (DMEM10). A 6-well plate was seeded with $0.5\times10^6$ cells per well and the pPro-eE2-Fc vector (from J6 strain) was transfected the following day using FuGene-HD (Roche Diagnostics, Basel, Switzerland). After three days, the cells were placed under hygromycin (Calbiochem, San Diego, Calif.) selection at 75 μg/ml. Individual colonies were selected, expanded, and tested for eE2-Fc expression using an anti-Fc ELISA.

Example 2

ELISA for eE2-Fc

MaxiSorp plates (Nunc, Thermo Fisher Scientific, Rochester, N.Y.) were coated with 100 μL of supernatant for two hours at room temperature. The wells were washed 3 times with 200 μL of PBS+0.05% Tween-20 (PBS-T), then blocked with 200 μL of 2% BSA in PBS-T for one hour at room temperature. After three more washes with PBS-T, 100 μL of goat anti-Fc antibody (Pierce, Thermo Fisher Scientific, Rochester, N.Y.) at 1:15,000 dilution (in PBS-T) was incubated for one hour at room temperature. The ELISA was developed with TMB substrate (Pierce) and quantified using the SpectraMAX 250 plate reader and SOFTMax 2.6 software.

Example 3

Expression and Purification of eE2

The supernatant from stable cell lines of Example 1 was harvested, centrifuged to remove cellular debris, and filtered through a 0.22 μm membrane. The eE2-Fc protein was applied to protein A-conjugated resin (GE Healthcare, Piscataway, N.J.) overnight with gentle rocking. The resin was pooled together the next day, washed with buffer (50 mM HEPES pH 7.5, 150 mM KCl, 5% glycerol), and incubated with thrombin protease (GE Healthcare, Piscataway, N.J.) to release the protein from the Fc tag. After cleavage, the protein eluate was consolidated and the concentration determined by Bio-Rad Protein Assay. The protein was analyzed by SDS-PAGE and Coomassie staining Yields are found to be about 2 mg of eE2 per liter of supernatant.

Example 4

Deglycosylation of eE2 eE2 was deglycosylated using either Endo H or PNGase F according to manufacturer's protocol (New England Biolabs, Ipswich, Mass.). 20 μg of eE2 was denatured and 10 Units of Endo H or PNGase F was added. The reaction was incubated at 37° C. for one hour and analyzed by SDS-PAGE followed by Coomassie staining.

Example 5

Mapping the N-Linked Glycosylation Sites

The eE2 protein sample was denatured in 6M urea, then reduced with 10 mM DTT for 30 min at 60° C. After denaturation, 20 mM iodoacetamide was added to alkylate sulfhydryl groups and incubated in the dark for one hour at room temperature. Following this treatment, the sample was buffer-exchanged into 50 mM $NH_4HCO_3$. The sample was digested using either sequencing grade trypsin (Promega, Madison, Wis.) or chymotrypsin (Roche Diagnostics) according to manufacturers' protocol. Digested samples were dried via speed vacuum and reconstituted in 50 mM $NH_4HCO_3$. Deglycosylation with 50 U of PNGase F (New England Biolabs, MA) was incubated for 1 hour at 37° C. and the reaction was stopped with 0.1% trifluoroacetic acid (TFA).

Example 6

Liquid Chromatography Analysis

All LC-MSMS experiments were performed using the U3000 (Dionex, Sunnyvale, Calif.) in nano-LC mode on line with LTQ (Thermo Fisher Scientific). Samples were first solubilized in 0.1% TFA and loaded onto a 75 μm×12 cm emitter column self-packed with Magic C18AQ, 3 μm 200 Å. (Michrom Bioresources Inc, Auburn, Calif.). The sample was eluted using a linear gradient from 98% of 0.1% formic acid in water to 45% of 0.1% formic acid in acetonitrile over 30 min. Mass spectrometry data was acquired using a data-dependent acquisition procedure with a full scan cyclic series. This was followed by zoom scans and MSMS scans of the five most intense ions with a repeat count of two and a dynamic exclusion duration of 60 sec.

The LC-MSMS data was searched against a human database using a local version of the Global Proteome Machine (GPM USB, Beavis Informatics Ltd, Winnipeg, Canada). Carbamidomethylation of cysteine was used as the fixed modification, while oxidation of methionine and deamination of asparagine were used as potential modifications. Manual interpretation and peak integration was performed on all peptide peaks covering potential glycosylation sites (NXT/S).

Example 7

Gel Filtration Analysis of eE2

Purified eE2 protein was loaded onto a Superdex 200 10/300 size exclusion column (GE Healthcare) equilibrated with either HEPES buffer (50 mM HEPES pH 7.5, 150 mM KCl, 5% glycerol) or phosphate buffer (25 mM sodium phosphate pH 5.0 or 7.0, 50 mM KCl).

Example 8

Free Cysteine Analysis

To label free cysteines, the protein sample was incubated with a 20-fold molar excess of N-ethylmaleimide (NEM) and 6M guanidine-HCl at room temperature for one hour in the dark. The sample was then buffer exchanged to 6M guanidine-HCl using a spin filter and washed three times with 400 μl of 6M guanidine-HCl to remove the NEM. Disulfide bonds were reduced by adding 10 mM DTT at 60° C. for 30 min. The newly generated free sulfhydryl groups were alkylated with 20 mM iodoacetamide (JAM) at room temperature for one hour in the dark. After buffer exchange into 50 mM $NH_4HCO_3$, the samples were digested with trypsin protease at 37° C. overnight. The samples were then deglycosylated with PNGaseF (100 U) at 37° C. for three hours and acidified prior to LC-MSMS analysis.

The LC-MSMS data was searched using Sequest against an E. coli genome database (a common contaminant of in-gel digest) and added sequences of the target protein. +57 Da (alkylation by IAM) and +125 Da (alkylation by NEM) on cysteine, oxidation of methionine (+16 Da), and deamination of asparagine (+1 Da) were used as potential modifications. The identification was confirmed manually.

Example 9

Analytical Ultracentrifugation

All sedimentation experiments were performed with a Beckman Optima XL-I at the Center for Analytical Ultracentrifugation of Macromolecular Assemblies at the University of Texas Health Science Center at San Antonio. Sedimentation velocity data were analyzed with UltraScan version 9.9. All measurements were made at 230 nm in intensity mode, at 20° C., and at 37 krpm, using standard upon 2-channel centerpieces. All samples were measured in 25 mM sodium phosphate buffer containing 50 mM KCl, adjusted to either pH 5.0 or 7.0. Concentration dependency of the sedimentation data was assessed by sedimenting the sample at both high concentration (~0.8 optical density (OD) at 230 nm) and at low concentration (~0.25 OD at 230 nm). Hydrodynamic corrections for buffer density and viscosity were made according to methods outlined in Laue et al. and as implemented in UltraScan. The data were analyzed by 2-dimensional spectrum analysis (2DSA) using the AST-FEM-RA solution with simultaneous removal of time-invariant noise. Molecular weight and shape distributions obtained in the 2DSA were further refined by Monte Carlo analysis. Composition comparisons were made by overlaying sedimentation coefficient distributions derived from the van Holde-Weischet analysis. The calculations were performed on the Lonestar cluster at the Texas Advanced Computing Center at the University of Texas at Austin, and at the Bioinformatics Core Facility at the University of Texas Health Science Center at San Antonio.

Example 10

Circular Dichroism

The protein sample was buffer-exchanged into 25 mM sodium phosphate pH 5.0 or 7.0, and 50 mM KCl. The CD spectra in the wavelength range of 195-260 nm were measured at 0.5 nm intervals on an Aviv spectropolarimeter model 400 (Lakewood, N.J.) at 25° C. A quartz cell with a path length of 0.1 cm was used. The CD spectra were analyzed for secondary structure using multilinear regression as described previously.

Example 11 eE2 ELISA Using Human Sera 96-well EIA/RIA plates (Corning, Lowell, Mass.) were coated with 100 μl of a 1 μg/ml solution of eE2 in $NaHCO_3$ overnight at 4° C. The plates were washed twice with 200 μl/well PBS-T, then blocked with a 10% solution of normal goat serum in PBS-T (Jackson ImmunoResearch, West Grove, Pa.) for one hour at 37° C. Human serum was isolated from whole blood samples (Emory University School of Medicine, PI Arash Grakoui, IRB#1358-2004) collected in SST tubes (Becton Dickenson, Franklin Lakes, N.J.) via centrifugation and frozen in aliquots at −80° C. Ten-fold serial dilutions were made for each serum sample using binding buffer composed of 0.1% normal goat serum in PBS-T. 100 μl of the dilutions was added to each well of the plates and incubated for 90 minutes at room temperature. The plates were washed eight times with PBS. 100 μl of goat anti-human IgG-Biotin conjugate (Biosource, Camarillo, Calif.) diluted 1:20,000 in binding buffer was added and allowed to incubate for 90 minutes at room temperature. Finally, 100 μl streptavidin-HRP conjugate (Biosource) was added to each well at a 1:2,000 dilution and incubated for 45 minutes at room temperature. Using TMB substrate solution (Ebioscience, San Diego, Calif.), absorbance was measured using a VersaMax Microplate reader and SoftMax Pro software (Molecular Devices, Sunnyvale, Calif.).

Example 12

HCVcc Infection in the Presence of Purified Proteins

Approximately 100 TCID50 of Cp7 viruses were incubated with two-fold dilutions of the purified eE2, eE2-C656S, GST, GST-CD81LEL or GST-mCD81 starting at 200 μg/ml. $6.0 \times 10^3$ cells were seeded into a collagen-coated 96-well plate. The virus-protein mixture was incubated with the cells for three days at 37° C. Cells were stained by immmunohistochemistry as previously described.

Example 13

Cytotoxicity

Huh-7.5 cells were incubated with various dilutions of the purified proteins as described above. Three days later, cells were washed twice with PBS, harvested by trypsinization, and resuspended in 100 μl of PBS. Cells were stained with BD Via-Probe™ (BD Biosciences, San Jose, Calif.) according to the manufacturer's instructions and counted using FACSCalibur (BD Biosciences) equipment and FlowJo (v8) analysis software.

Example 14

Expression and Purification of GST and GST-CD81-LEL

CD81-LEL was expressed with an amino-terminal GST tag and carboxy-terminal histidine tag. The protein was expressed and purified as described previously. The GST tag alone was expressed and purified using the same method.

Expression of eE2 in *E. coli*, yeast, insect cells, CHO cells, and various other eukaryotic and viral recombinant systems, has consistently resulted in the formation of insoluble, misfolded and aggregrated protein. We sought to develop a system for the expression of HCV eE2 that would yield large amounts of highly purified, active protein for functional studies. Our approach was to utilize cell lines that have been shown to produce functional E2, while adding an affinity tag to increase eE2 stability and facilitate purification. HEK293T cells were chosen owing to a) their ability to produce functional E2 in the form of HCV pseudoparticles (HCVpp), b) their ease of handling and robust growth rate and, c) their excellent transfectability and high capacity for recombinant protein expression. We expressed the J6 (genotype 2a) E2 ectodomain (aa384-664) because this fragment of E2 has been shown to be the minimal functional unit for binding and entry (FIG. 8A). eE2 is preceded by a prolactin signal sequence and signal peptidase cleavage site to promote trafficking through the secretory pathway and followed by a thrombin cleavage site and Fc tag (eE2-Fc). The Fc tag was chosen since it is glycosylated and disulfide-bonded, which may assist similar posttranslational modifications on eE2. We have created a HEK293T cell line that stably secretes eE2-Fc into the media. The eE2-Fc was isolated using protein A resin and eE2 was subsequently separated from the Fc tag via thrombin protease cleavage, leaving the Fc tag bound to the resin (FIG. 8B). The calculated molecular weight of the J6 eE2 protein is 33 kDa, although it migrates around 60 kDa by reducing SDS-PAGE. This molecular weight discrepancy and the diffuse nature of the band are observations consistent with glycosylated proteins.

Example 15

Analysis of Glycosylation

Glycosylation of viral envelope proteins is critical for folding, structural integrity, and immune evasion. The number and conservation of glycosylation sites varies across different HCV genotypes. J6-E2 contains 11 potential N-linked glycosylation sites (N-X-T/S) along with three potential O-linkage consensus sites (FIG. 8A). We investigated the extent of eE2 N-linked glycosylation and the type of oligosaccharide at each site using endoglycosidases. High mannose and complex oligosaccharides can be differentiated by endoglycosidase H (Endo H) sensitivity, since Endo H will only cleave high mannose glycans. Peptide-N-glycosidase F (PNGase F) will remove all types of N-linked glycosylation indiscriminately. Deglycosylation of eE2 with PNGase F under denatured, reducing conditions resulted in a faster migrating band greater than 31 kDa, consistent with its calculated molecular weight of 33 kDa (FIG. 9A). In contrast, eE2 was largely resistant to digestion with Endo H (FIG. 9A). This result suggests that the majority of the N-linked glycans on eE2 are of the complex form, in accordance with its mode of expression by export through the secretory pathway.

To investigate the glycosylation pattern in further detail, we employed high-resolution mass spectrometry. eE2 was digested with either trypsin or chymotrypsin and samples of the protein fragments were deglycosylated with either PNGase F or Endo H. PNGase F deaminates the asparagine residue to which the N-linked glycan is attached and converts it to aspartic acid. If the glycan is of the high mannose form, it will be sensitive to Endo H, which leaves one N-acetylglucosamine (GlcNAc) bound to the Asn. Thus, the gain of 1 Da (Asn to Asp; nitrogen to oxygen) by PNGase F or 203 Da by the GlcNAc residue left by Endo H cleavage can be resolved by MS of the peptides. From the resulting three spectra (untreated, Endo H and PNGase F treated) we are able to map all the glycosylation sites, estimate the approximate usage of each site, and determine whether the glycan at a particular site was complex or high mannose. We achieved 100% coverage of the eE2 sequence using trypsin and chymotrypsin. Peptides from the 11 predicted N-linked glycosylation sites were shown to be fully glycosylated, since we were unable to detect unglycosylated peptides with Asn residues in them (FIG. 9B, upper spectra). Only one of the 11 glycosylation sites was found to be Endo H sensitive (VGGVEHRLTAACNF, data not shown for Endo H), suggesting that the majority of the glycans are complex in nature (FIG. 9B, lower spectra). Peptides containing the potential O-linked glycosylation sites were resolved and shown to be unmodified (data not shown).

Example 16

Oligomeric State of eE2

Since previous reports have shown that E2 tends to aggregate, we set out to define the oligomeric state of eE2, using nonreducing SDS-PAGE, size exclusion chromatography and analytical ultracentrifugation. SDS-PAGE analysis of eE2 under non-reducing conditions demonstrated that the eE2 consisted of a mixture of two components with approximate molecular weights of ~120 kDa (dimer) and ~60 kDa (monomer) without any large, disulfide-linked aggregates (FIG. 10A). The dimer is formed by an intermolecular disulfide bond, since the addition of reducing agent (β-mercaptoethanol) yielded monomer (FIG. 10A). Size exclusion chromatography of eE2 under native conditions yielded two major peaks and a slight peak found in the void volume of the column. (FIG. 10B). The major and minor peaks were measured at ~123 kD and ~75 kDa, respectively, with a significantly greater proportion of dimer. The ratio of dimer to monomer in non-reduced SDS-PAGE (FIG. 10A) and gel filtration (FIG. 10B) is remarkably similar.

Since, there are 18 conserved cysteines in E2, this could result in the formation of nine disulfide bonds. The eE2 fragment contains only 17 cysteines, leaving at least one unpaired. We therefore sought to determine which cysteine residue was responsible for the intermolecular disulfide bond demonstrated in FIG. 10A. Since eE2 contains a mixture of monomer and dimer, we employed differential cysteine labeling followed by high-resolution mass spectrometry to distinguish free cysteine residues from those involved in disulfide bonding. Briefly, eE2 was incubated with a molar excess of N-ethylmaleimide (NEM, 125 Da) under denaturing conditions to label all free cysteine residues. After disulfide bond reduction with DTT, the newly generated free cysteines were alkylated with iodoacetamide (IAM, 57 Da). The modified protein was digested with trypsin, deglycosylated with PNGaseF, and the resulting peptides were resolved by MALDI mass spectrometry. All cysteine-containing peptides were identified and only one peptide ($C^{656}$NLEDRDR) was modified by NEM (FIG. 11A). The expected unmodified molecular weight of this peptide is 1020.45 Da, 1077.45 Da if modified by IAM, or 1145.45 Da if modified by NEM. In FIG. 11A, the spectrum shows a 573.75 Da peak corresponding to this peptide modified by NEM and carrying a +2 charge, while no peptide appears at a position corresponding to a modification by IAM (expected ~538 Da). All other cysteine-containing peptides were shown to have an addition 57 Da, indicating that they were only freed after reduction with DTT. For example, the expected molecular weight of the unmodified SACRSIEAF peptide is 983.46 Da, 1040.46 Da if modified by IAM, or 1108.46 if modified by NEM. This peptide resolves at 521.32 Da, which corresponds to the molecular weight when modified by IAM and carrying a +2 charge. It does not resolve as modified by NEM (expected ~554 Da) (FIG. 11B).

Figure 15:
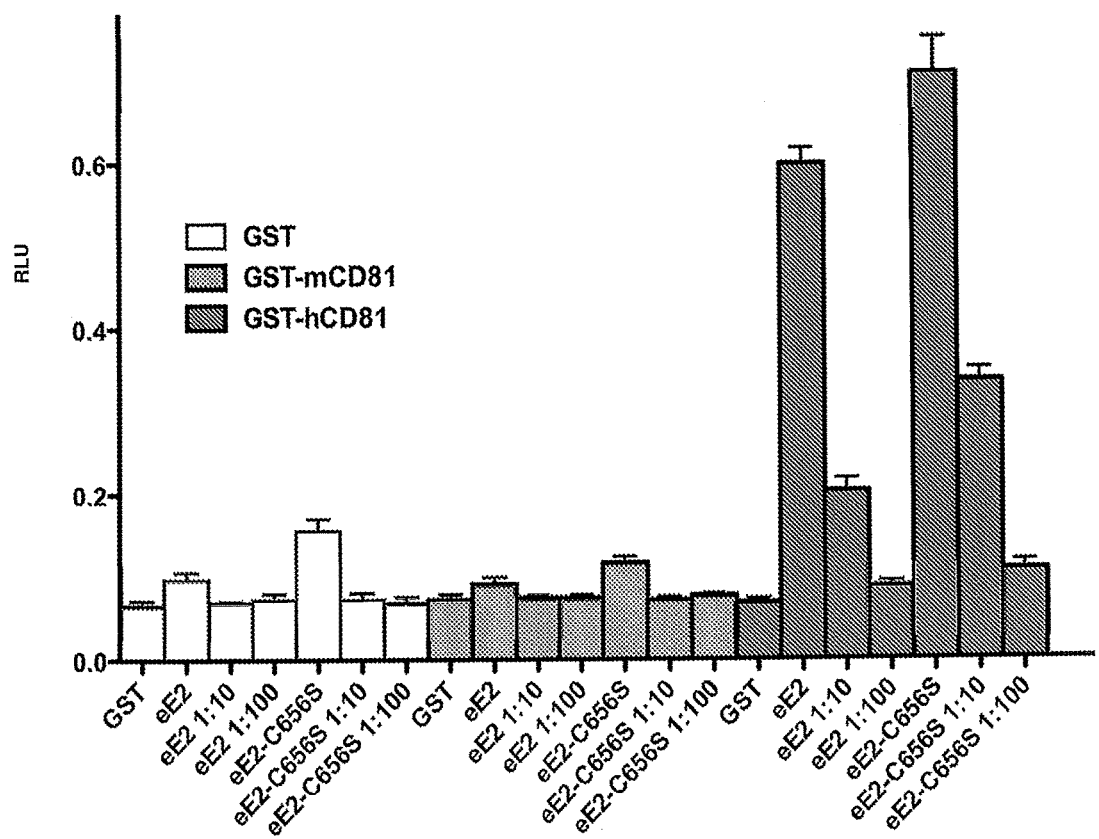
FIG. 15. Shows graphical depictions of functional analyses of eE2 and eE2-C656S. (A) ELISA plates were coated with eE2 and probed with a series of ten-fold dilutions of serum from patients infected with HCV (genotypes 1, 2, or 3) and a healthy donor. Antibodies in HCV-infected patient sera could detect eE2 up to 1:100,000 dilution. (B) Cells were incubated with HCVcc plus GST, GST-mCD81 LEL, GST-hCD81 LEL, eE2, and eE2-C656S. Three days post-infection the cells were fixed, focus forming units were determined, and percent of inhibition was calculated. eE2, eE2-C656S, and hCD81 inhibit HCVcc infection. Error bars represent standard error of the mean for two independent experiments. Each experiment was performed in duplicate. (C) Cells were incubated with eE2, GST and GST-hCD81-LEL at three concentrations (200, or 100 µg/mL). Three days later, cells were analyzed for viability using flow cytometry. The results demonstrate that eE2 is not toxic when applied to cells at the concentration that inhibits HCVcc infection. (D) Enzyme-linked immunoassay for CD81-LEL binding. Tissue culture supernatants of eE2-Fc fusion (no dilution, 1:10 and 1:100 dilutions) were incubated in plates coated with either GST, GST-mouse CD81-LEL, or GST-human CD81-LEL. After washing bound eE2-Fc was detected with anti-human Fc-HRP. PBS, media form wt HEK293T cells and wells without any coating were used as controls. Both eE2 and eE2-C656S bound to only human CD81.

Consequently, we generated a mutant form of eE2 in which C656 was mutated to a serine (eE2-C656S). Serine was chosen to conserve the biochemical properties at this position. We generated a HEK293T cell line that stably expresses eE2-C656S-Fc and the protein was purified as before. eE2-C656S was analyzed by size exclusion chromatography under conditions identical to the eE2 wild type experiment and the results demonstrated that the mutant was predominantly monomeric at pH 7.5 (FIG. 11C).

Example 17

Analysis of eE2 and eE2-C656S at Low pH

Entry of HCV and other flaviviruses is a pH-triggered event. The single envelope protein (E) of flaviviruses undergoes a slight conformation shift upon incubation at low pH, resulting in a change in the oliogomeric state from dimer at neutral pH to trimer at low pH. Therefore we were interested in determining if HCV eE2 or eE2-C656S undergoes any structural or oligomeric changes when the pH is lowered. Gel filtration results for eE2 at pH 5 revealed a slight increase in the amount of monomer relative to pH 7 (FIG. 12A). This was not surprising, since the dimeric form is stabilized by a disulfide bond and should therefore be pH insensitive. Conversely, gel filtration results for eE2-C656S at pH 5 showed an increased proportion of monomer relative to dimer (FIG. 12B) and the disappearance of the peak found in the void volume at pH 7. These results provide the first physical evidence of a possible shift in E2 oligomerization in response to low pH.

Sedimentation velocity experiments by analytical ultracentrifugation can be used to determine frictional properties (mass and shape) of proteins without the use of standards or interactions with sieving matrix. Sedimentation of eE2 at pH 7 indicates the presence of two dominant species, a monomeric form (60-70 kDa) and a dimeric form (80-130 kDa) (FIG. 13A-D). There is a minor third species that has the approximate molecular weight of a trimer (150-200 kDa). This species seems to correspond to the small peak found in the void volume in size exclusion chromatography. The monomer has a frictional ratio in the range of 1.0-2.0 where a perfect sphere would have a frictional ratio of 1.0. It is interesting to note that the frictional ratio shows a decreasing trend with increasing molecular weight, suggesting a more globular shape for the oligomeric forms. Analysis of eE2 at pH 5 changes the percentage of the three species from 65%:29%:6% to 73%:27%:0% (monomer:dimer:trimer). There is no appreciable difference in the molecular weight or shape distributions at the two concentrations used in this analysis (OD230 nm of 0.25 and 0.8), indicating little or no mass action effects. We also investigated if the shift to lower-molecular weight species at pH 5 is reversible when the pH is restored to 7 (FIG. 13E). It is clearly visible that a drop in pH to 5 reduces the sedimentation speed of about 30-40% of the sample by an appreciable amount, and that this portion is essentially restored to the higher sedimentation coefficient when the sample is returned back to pH 7. This demonstrates that the oligomerization behavior of eE2 when undergoing a pH shift is completely reversible.

The HCV glycoproteins are predicted to be class II fusion proteins, due to their similarity to alphaviruses and flaviviruses. These proteins are composed of mostly β sheet structure and do not undergo major structural rearrangements upon exposure to low pH. We investigated this possibility by measuring circular dichroism of eE2 and eE2-C656S at pH 7 and pH 5. The resulting spectra revealed that both eE2 and eE2-C656S contain predominantly β-sheet structure and random coil with a small amount of α-helix (FIG. 14). The CD spectra at pH 7 and pH 5 are superimposable for both constructs, indicating that changes in the oligomeric nature of eE2 by lowering the pH are not due to rearrangement of secondary structure.

Example 18

Recognition of J6 eE2

J6 eE2 is recognized by antibodies from patients chronically infected with different genotypes of HCV. The presence of high levels of anti-E2 antibodies in HCV-infected human serum has been reported. In order to further examine if purified eE2 is conformationally similar to the E2 present on infectious HCV particles, we tested whether eE2 was recognized by antibodies from infected patient sera. An enzyme-linked immunosorbent assay (ELISA) plate was coated with eE2 and probed with serum from patients chronically infected with either genotype 1, 2 or 3. Serum from a healthy donor was tested in parallel as a negative control. Anti-human HRP was used to quantify the result. The serum of infected patients bound to eE2 at similar titers regardless of genotype, while the serum of the uninfected donor responded at background levels (FIG. 15A). This illustrates the capacity of eE2 to be recognized by antibodies in patient sera, while also pointing out the maintenance of cross-reactive epitopes.

Example 19

Inhibition of Virus Entry

The HCV eE2 blocks HCVcc entry. In order to confirm correct folding and function of HCV eE2, we performed a similar assay using cell culture derived HCV (HCVcc). ~100 TCID50 of HCVcc was incubated with serial 2-fold dilutions of purified eE2, eE2-C656S, GST-human-CD81LEL (hCD81), GST-mouse-CD81LEL (mCD81) or GST. eE2, eE2-C656S, and hCD81 reduced the number of focus forming units (FFU) in a concentration dependent manner, while mCD81 and GST protein had no effect. This experiment yielded a 50% blocking efficiency in the range of 25-150 μg/ml for eE2 and eE2-C656S (FIG. 15B). Thus, HCVcc infection can be effectively blocked by eE2 or eE2-C656S. This further supports the congruence between eE2, eE2-C656S, and full length E2 in the context of virus. In order to rule out the possibility that inhibition of viral infection was due to toxicity, we quantified cell death after incubation with purified protein using fluorescence activated cell sorting analysis (FACS). Cells were incubated for 3 days with 2-fold dilutions of eE2, GST and hCD81 followed by staining with Via-Probe™ to estimate viability. As shown in FIG. 14C, purified eE2 and hCD81 are not toxic at 200 μg/mL (the concentration with the highest level of inhibition).

Inhibition of HCVcc entry by eE2 is thought to occur by sequestering cellular receptors. To confirm this, we analyzed the ability of eE2 to bind hCD81 in vitro. We adapted an ELISA first described by Flint et al. for the detection of properly folded E2 based on hCD81 binding. We have obtained identical results using wild type and mutant eE2-Fc supernatants (FIG. 14D) and purified eE2 and eE2-C656S. Plates were coated with GST, mCD81, and hCD81, probed with eE2-Fc or eE2-C656S-Fc cell supernatants, then developed with HRP-conjugated anti-Fc. The assay was executed in triplicate using undiluted cell culture supernatant, supernatant diluted 1:10 in media, or supernatant diluted 1:100 in media. Both eE2-Fc and eE2-C656S-Fc specifically bind hCD81 but not mCD81 or GST alone (FIG. 15D).

DISCUSSION

HCV E1 and E2 are primary determinants of entry and pathogenicity. Deletion mutagenesis has defined the ectodomain of HCV E2 to comprise amino acids 384-664 of E2. Functional and biophysical studies of HCV E2 have been hindered by the formation of mostly aggregated, misfolded material. The eE2 protein produced as described here maintains many of the functionalities associated with E2 found on virions. eE2 can compete with HCVcc to inhibit infection, is recognized by antibodies from chronically infected patients, and can specifically bind the large extracellular loop of human CD81.

All eleven of the predicted N-linked glycosylation sites in E2 are utilized with high efficiency. This is consistent with previous data using HCVpp. Ten of the eleven sites have complex glycans attached, while only the most C-terminal is of the high mannose form. This observation suggests that the glycan at this position is concealed from the modification enzymes in the secretory pathway. This may occur as a result of the dimeric interface formed between two eE2-Fc molecules, or because of steric effects of the Fc tag attached to the C-terminus. As reported by Goffard et al, mutation of the C-terminal glycosylation site does not affect folding, secretion, or E1/E2 heterodimer formation, but does result in less than 50% infectivity when incorporated into HCVpp. Peptides containing the putative O-linked glycosylation sites (FIG. 8A) were not modified, as determined by LC-MS. However, at this time, we cannot rule out that O-linked glycosylation occurs at a low level on eE2 or when expressed as part of the HCV polyprotein.

The HCV glycoproteins, like those from related alphaviruses and flaviviruses, are predicted to be class II fusion proteins. This class of proteins is characterized as mostly beta sheet structures that do not undergo changes in secondary structure upon exposure to low pH. The flavivirus E protein (comprised of three domains) is responsible for receptor binding and membrane fusion. Flaviviruses have icosahedral symmetry, with E arranged as 90 dimers. Cryo-electron microscopy has demonstrated that the E protein lies flat on the surface of the viral lipid bilayer. Upon exposure to low pH there is a slight rotation of domain III, resulting in dissociation of the E dimers and rearrangement into trimers via a monomeric intermediate stage. eE2 appears mostly as a monomer and dimer with a much lower amount of trimer at pH7. Upon exposure to low pH there is an increase in the amount of monomer relative to dimer and trimer. This result represents the first observation of a shift in oligomeric arrangement of the HCV glycoproteins. However, the oligomeric state of E2 may be influenced by the deleted C-terminal portion, the high concentration found on virus particles, and/or heterodimerization with E1. CD spectroscopic analysis of HCV eE2 demonstrated a pronounced minimum at about 203 nm, consistent with a mostly n-sheet protein. Exposure to low pH does not result in a major rearrangement of secondary structure as determined by CD. However, CD cannot rule out the possibility of structural rearrangements that preserve the overall proportion of β-sheet and random coil. These data support the categorization of HCV E2 as a member of the class II fusion proteins.

HCV E2 has 18 highly conserved cysteine residues, although the eE2 construct as defined by Michalak et al. has the first 17. The $18^{th}$ is located between the ectodomain and the C-terminal membrane anchor. Differential labeling of free and disulfide-bonded cysteines has demonstrated the presence of eight disulfide bonds and one free cysteine (C656) in eE2. Mutating C656S did not affect inhibition of HCV entry (FIG. 8B), CD81 binding (FIG. 8D), or binding to HCV patient antibodies (data not shown). Our results are consistent with recently published data, showing that all 18 cysteine residues of E2 are in disulfide bonds and reduction of up to half of these disulfides was compatible with HCV entry as well as antibody and CD81 binding.

Based on the results shown in this study and in accordance with previous studies on the HCV envelope proteins, it is highly possible that E2 may provide an excellent vaccine candidate. Chimpanzees immunized with E1/E2 heterodimeric proteins are protected from infection with low doses of homologous hepatitis C virus. In 1991, Weiner et al. identified hypervariable regions in E2, while it was later shown that deletion of hypervariable region 1 attenuated infection in chimpanzees. Youn et al. did further work in chimpanzees to show that an E2 antibody response correlates with lower viral titres. Most recently, rodents injected with HCV envelope glycoproteins have been shown to produce antibodies that are broadly cross-reactive in their neutralization properties. The production of large quantities of functional and properly folded E2 ectodomain will aid in our understanding of E2 function as well as assist in designing a vaccine and entry inhibitors.

Example 20

Methods and Summary

Recombinant, full-length E2 ectodomain (384-656, genotype J6), eE2(DHVR1) (413-656) and E2 core (456-656) were produced in HEK293T GnTI2cells27 by a lentiviral expression system with a C-terminal, protein-A tag. Stable cell lines were grown in an adherent cell bioreactor. Collected supernatants were purified over IgG sepharose and the E2 proteins were eluted by PreScission Protease digestion. The eluted protein was deglycosylated with endoglycosidase H (EndoH) and purified to homogeneity by heparin affinity and size-exclusion chromatography. Monoclonal antibody 2A12 secreted by hybridoma cells maintained in suspension culture was purified over protein G resin. Fab was generated using papain digestion and subtractive protein A chromatography. E2 and 2A12 Fab complex was purified by size-exclusion chromatography and crystals were obtained in 18% (w/v) PEG 3350, 0.5M $MgCl_2$, 0.1M HEPES (pH7.5), 15% dioxane and 2% formamide at 20° C. by the hanging-drop vapour diffusion method. The crystals belong to space group $P2_12_12$ with cell parameters a=85.96 A°, b=194.57 A° and c=37.92 A°. The structure was determined by molecular replacement to 2.4 A° resolution using a mouse Fab (Protein Data Bank accession 2GSI). The final model has an $R_{work}$ and $R_{free}$ of 0.217 and 0.269, respectively. SAXS measurements were performed on eE2, E2 core, eE2(DHVR1) and eE2(DHVR1)/CD81-LEL. Data were analysed using BioXTAS RAW28 and applications from the ATSAS29 program suite.

J6 eE2 Expression eE2, eE2(ΔHVR1) and E2 core domain encompasses residues 384-656, 413-656 and 456-656 from the HCV J6 genome, respectively. Owing to incomplete deglycosylation at N7 (542) with Endo H, the crystallization construct contained an asparagine to glutamine mutation at this position. The expression constructs consisted of a CMV promoter, a prolactin signal sequence, E2 fragment, PreScission Protease cleavage site and a C-terminal protein-A (ProtA) tag. The entire prolactin-E2-ProtA sequence was PCR amplified and cloned into the pJG lentiviral vector (J. Shires).

Wild-type and GnTI-HEK293T cells[127] (provided by D. Comoletti) were maintained in Dulbecco's Modified Eagle Medium (DMEM) with 10% fetal bovine serum (FBS) at 37° C. with 5% $CO_2$. One day before the planned transfection, a single T-225 monolayer flask was seeded with $6.0 \times 10^6$ HEK293T cells. 90 μg pJG-E2, 60 μg psPAX2 (HIV Gag-Pol packaging vector), 30 μg pMD2.G (VSV glycoprotein vector) and 450 μl of 2 M $CaCl_2$ were mixed and brought to a final volume of 4.5 ml with dd$H_2O$. 4.5 ml of 2×HEPES buffered saline was added at room temperature. After a 2-min incubation, the mixture was added directly to HEK293T cells. After 6-8 h, the media was replaced with DMEM with 10% FBS and 1% antibiotic/antimycotic (A/A) media and incubated for another 70 h.

Two days after transfection, 10,000 GnTI-HEK293T cells were seeded into a single well of a 96-well plate. The supernatant from the transfection, containing the recombinant lentiviruses, was collected and centrifuged for 30 min at 4,000 g at 4° C. to pellet large cellular debris. Clarified supernatant was transferred to a Beckman Ultracentrifuge tube and virus was pelleted for 1.5 h at 25,000 r.p.m. (80,000 g) at 4° C. in an SW28 rotor. Supernatant was discarded and the pellet re-suspended in 120 μl of DMEM containing 20% FBS, 1% A/A, and 8 μg $ml^{-1}$ of polybrene. 60 $μl^{-1}$ of virus suspension was added to the prepared GnTI-HEK293T cells and incubated overnight. Infected cells were expanded and ultimately seeded into an adherent cell bioreactor (Cesco Bioengineering) for long-term growth and protein production.

eE2, eE2(ΔHVR1) and E2 Core Purification

Cell supernatant containing E2-ProtA was centrifuged for 10 min at 7,000 g, filtered through a 0.22-μm membrane, and loaded onto an IgG FF column (GE Healthcare). The column was extensively washed with 20 mM sodium phosphate pH 7.0 and then equilibrated with 20 mM HEPES pH 7.5, 250 mM NaCl and 5% glycerol. PreScission Protease was added into the column at approximately 400 μg $l^{-1}$ of supernatant and incubated overnight at 4° C. For deglycosylation, the pH of the protein solution was adjusted using 1 M sodium citrate pH 5.5 to a final concentration of 100 mM. Endo H was added at a ratio of 1 mg per 2 mg of E2 and the reaction was incubated at room temperature for 3-4 h. The deglycosylated proteins were desalted into 20 mM HEPES pH 7.5, 50 mM NaCl, and 5% glycerol and purified by heparin affinity followed by size-exclusion chromatography over a Superdex 200 column. Final yields for all E2 proteins averaged 30 mg $l^{-1}$ of supernatant.

Crystallization

A 1.1:1 molar ratio of E2 core domain to Fab was incubated for 1-2 h at 4° C. The complex was purified over a Superdex200 column equilibrated with 20 mM HEPES pH 7.5 and 100 mM NaCl. The complex was concentrated to 5-7 mg $ml^{-1}$ and crystals were grown by the hanging-drop vapor diffusion method. Briefly, 2.5 μl of complex was mixed with an equal volume of reservoir solution, comprising of 22% (w/v) PEG 3350, 0.5 M $MgCl_2$, 0.1 M HEPES pH 7.5, and 15% (v/v) dioxane. Initially, clusters of plate-like crystals grew in 3-4 days. Single, plate-like crystals were obtained via microseeding using a similar reservoir solution supplemented with 2% (v/v) formamide. Crystals were cryoprotected using reservoir solution with 24% (v/v) ethylene glycol and flash cooled in liquid nitrogen. Data were collected at a wavelength of 0.979 A using beamline X25 of the National Synchrotron Light Source (NSLS), Brookhaven National Laboratory.

Structure Determination and Refinement

The crystals belong to space group $P2_12_12$ with cell parameters a=85.96 Å, b=194.57 Å, c=37.92 Å. Phases were determined by the molecular replacement method using PHENIX[130] and the coordinates from chains A and B from PDB entry 2GSI. Unambiguous placement of the Fab heavy and light chains provided the necessary phases to extend the map to cover E2 core domain using iterative rounds of model building and density modification by COOT[131], PHENIX, REFMAC[132] and PARROT[133]. The final model was built to a resolution of 2.40 A, comprising residues 492-522, 538-571 and 596-649 of E2 from the J6 genome, 1-217 of 2A12 light chain, and 1-133 and 136-218 of 2A12 heavy chain with two N-linked, N-acetylglucosamine, six molecules of formamide and 141 solvents molecules. The model coordinates were refined to $R_{work}$ 0.217 and $R_{free}$ 0.269. Model validation demonstrated 95.0% of the residues located in the most favorable region of the Ramachandran plot with 4.8% in the generously allowed regions[30]. Statistics of the data processing and structure refinement are summarized in FIG. 25.

Small Angle X-Ray Scattering (SAXS)

Glycosylated E2 proteins were purified over IgG and anion exchange columns. The proteins were equilibrated with either pH 7.5 buffer (50 mM HEPES pH 7.5, 250 mM NaCl and 1% glycerol) or pH 5.0 buffer (50 mM sodium citrate pH 5.0, 250 mM NaCl and 1% glycerol) by Superdex200 gel filtration column. Glycosylated eE2(ΔHVR1) alone or complex with CD81-LEL (1:2 molar ratios) was purified using pH 7.5 buffer by gel filtration chromatography. Three concentrations of each protein were prepared along with their respective buffers as background control. SAXS data was collected on the SIBYLS beamline at the Advanced Light Source, Lawrence Berkeley National Laboratory. Sample analysis and processing was performed using BioSAXS RAW[128], ATSAS[129], and GNOM[134]. The ab initio models were calculated using the application DAMMIF[135]. Consensus models and the normalized spatial discrepancy (NSD) values were calculated by averaging 10 ab initio models using the application DAMAVER[136]. X-ray structures of CD81 (PDB ID 1G8Q), HCV E2 core and ab initio models were aligned using the application SUPCOMB[137].

Hydrogen Deuterium Exchange

HD exchange experiments were conducted as described previously[138]. Briefly, 5 μl of deglycosylated eE2 (1.5 mg $ml^{-1}$), in 200 mM NaCl, 20 mM HEPES pH 7.5, was incubated with 15 μl of the same buffer made with 99.96% $^2H_2O$ (Cambridge Isotope Laboratories) for 10, 100, or 1,000 s and quenched in 30 μl of 2 M urea, 0.8% formic acid and 50 mM tris(2-carboxyethyl)phosphine (TCEP). The reaction mixture was immediately frozen on dry ice until injection. For the zero time point experiment, the protein was incubated in the buffer made with $^1H_2O$ and then quenched and frozen. To correct background exchange, a completely deuterated sample was produced by incubating the protein with 100 mM TCEP in 99.96% $^2H_2O$ overnight before being quenched and frozen. Dionex RSLC with a C18 column (2.1×50 mm, 3 μm, Q-C18, 150A, CMP Scientific) and LTQ Velos Orbitrap pro were used for LC-MS analysis. The mass was measured using Orbitrap with resolution of 60,000 and mass range from 300 to 2,000 m/Z. The LC-MS data were analysed using HDexaminer 1.2.0 (Serra Analytics) with manual checking of each peptide afterwards.

Limited Proteolysis 8-10 μg of deglycosylated eE2 protein was mixed with trypsin, chymotrypsin or GluC at 1:120 (w/w) ratio (endopeptidase:E2) and incubated at room temperature. Samples were taken at noted time points and analysed by reducing SDS-PAGE, mass spectrometry and N-terminal sequencing.

Production of Monoclonal Antibody 2A12

Six to eight week old female BALB/c mice were immunized intraperitoneally with 50 μg eE2 in either complete Freund's adjuvant (first immunization only), or incomplete Freund's adujvant bi-weekly for 8 weeks. A final immunization with 50 μg of eE2 was given intravenously 4 days before collection of splenocytes. Hybridomas were generated using a cloned HAT-sensitive mouse myeloma cell line as a fusion partner. Proliferating hybridomas were screened for their ability to bind eE2 via ELISA, at which point 2A12 was positively identified. Monoclonal antibodies were generated in the laboratory of A. Grakoui (IACUC protocol number YER-2002369-070816GN).

Generation and Purification of 2A12 Fab

Hybridoma cells were expanded to a final volume of 2l in spinner flasks at 100 r.p.m. using Iscove's Modified Dulbecco's Medium, 10% ultra-low IgG FBS, 1% A/A, and 10 mM HEPES (Life Technologies). Cells were collected at 2-3×10$^6$ cells per ml, centrifuged for 10 min at 7,000 g, filtered through a 0.22 μM membrane, and loaded onto a Protein G column (GE Healthcare Life Sciences). After completion, the column was washed with 20 mM sodium phosphate (pH 7.0) followed by phosphate buffered saline (PBS). The antibody was eluted with 0.05% TFA in 2 ml fractions into tubes containing 100 μl of 1 M Tris pH 7.5 for immediate pH neutralization. The eluted antibody was dialysed into 20 mM sodium phosphate pH 7.0 and 10 mM EDTA. Insoluble papain was added to the antibody at 0.15 mg per 1 mg of antibody. Freshly prepared L-cysteine was added to the reaction to a final concentration of 20 mM and mixed at 37° C. for 2 h. The papain was removed by centrifugation at 3,500 g for 2 min and filtration through a 0.22 μM membrane. Fab was purified by subtractive chromatography over Protein A FF column and desalted into 20 mM Tris pH 8.0.

Sequencing Ig H and L Chain Gene Segments of 2A12 Antibody

Total RNA isolated from 2A12 hybridoma cells was reverse transcribed into cDNA using random hexamers. Expressed heavy (H) and light (L) chains were amplified using standard primers that are complimentary to all murine H and L chain gene segments[39]. The PCR products were sequenced either directly or following cloning into pCR 2.1-TOPO vector (Life Technologies).

CD81 Purification and Binding Assays

Human CD81-LEL (residues 112-202) was produced as a fusion with C-terminal ProtA tag in HEK293T cells using the same lentiviral expression system described for eE2. Cell culture supernatants were loaded onto an IgG FF column, washed with 20 mM sodium phosphate pH 7.0, eluted with 100 mM sodium citrate pH 3.0 containing 20 mM KCl and immediately neutralized with 1 M Tris pH 9.0. The ProtA tag was cleaved by PreScission Protease (GE Healthcare Life Sciences) in a ratio of 1:50 (w/w) followed by overnight dialysis in 20 mM HEPES pH 7.5, 250 mM NaCl, and 5% glycerol. High-purity CD81 protein was obtained by anion exchange and size-exclusion chromatography.

For binding studies, a 96-well plate (Nalgene Nunc, Thermo Fisher Scientific) was coated with 50 μg of CD81-LEL overnight at 4° C. All experiments were duplicated against BSA as a negative control. Plates were washed three times with PBS containing 0.05% Tween 20 (PBS-T) and blocked with 3% (w/v) BSA in PBS-T for 1 h at room temperature. 50 μl of eE2 or E2 core at different concentrations was added to appropriate wells and incubated overnight at 4° C. On day 3, the wells were washed three times with PBS-T and incubated with monoclonal antibody 2A12 cell supernatant for 1 h at room temperature. Plates were washed three times with PBS-T and incubated with anti-mouse-HRP conjugated antibody for 1 h at room temperature. Finally, the plate was washed five times with PBS-T. 50 μl of TMB substrate (ThermoFisher Scientific) was added to each well and incubated for 5 min, followed by the addition of 50 μl of 2 M sulphuric acid to stop the reaction. Absorbance readings were acquired at 450 nm using Softmax Pro software on a Spectra Max 250 (Molecular Devices).

Neutralization Assay

Huh-7.5 cells were maintained in DMEM containing 10% FBS (Hyclone) and 100 μg ml$^{-1}$ of penicillin and streptomycin (Cellgro) at 37° C. in 5% $CO_2$. Naive Huh-7.5 cells were seeded at 6,000 cells per well in a 96-well plate. The following day, 100 μl of 2C1, 2A12, or H113 serially diluted in complete media were added per well at various concentrations. In parallel, 100 μl of eE2, E2 core, gp140, or CD81-LEL serially diluted in complete DMEM were added at varying concentrations beginning at 100 μg ml$^{-1}$. Cells were then infected with 100 μl of genotype 2a virus Cp7 encoding the *Renilla* luciferase gene[140]. 72 h after infection, relative light units were measured on a Clarity 4.0 luminometer (Biotek) using the *Renilla* Luciferase Assay System (Promega).

Assessment of Cellular Cytotoxicity

Huh-7.5 cells were incubated with varying concentrations of protein as described above, beginning at 100 μg ml$^{-1}$. After 72 h, cells were washed once with PBS, treated with trypsin, and collected in 100 μl PBS. Cells were stained with 7-AAD according to the manufacturer's instructions (BD Biosciences) and analysed using a BD LSR II and FlowJo software (Tree Star).

Human Plasma ELISA 96-well enzyme immunoassay plates (ThermoFisher Scientific) were coated overnight at 4° C. with 50 μl of a 1 μg ml$^{-1}$ solution of eE2 or E2 core diluted in 0.1 M $Na_2CO_3$. Plates were washed twice with PBS-T and then blocked for 1 h at 37° C. in PBS-T containing 10% fetal calf serum (HyClone). Blood samples were collected in heparin tubes (Becton Dickinson) and plasma was isolated and frozen at −80° C. Plasma was serially diluted in a binding solution composed of 0.1% (v/v) normal goat serum in PBS-T (Jackson ImmunoResearch Laboratories). 100 μl of sample were added per well and incubated at room temperature for 90 min. After eight washes with PBS, 100 μl of mouse anti-human IgG biotin antibody (Mabtech) diluted 1:20,000 in binding solution were added per well and incubated 1 h at room temperature. Following five additional washes with PBS, 100 μl streptavidin-horseradish peroxidase (HRP) conjugate was added to each well at a 1:2,000 dilution in binding buffer and incubated for 45 min at room temperature (Mabtech). Absorbance was measured and analysed using a VersaMax microplate reader and SoftMax Pro software (Molecular Devices) following five washes and the addition of tetramethylbenzidine substrate solution (Ebioscience). Human sera were isolated from whole-blood samples, and informed consent was obtained for all subjects (IRB no. 1358-2004, Emory University School of Medicine, principal investigator A. Grakoui).

Alignment

Secondary structures were assigned using the program DSSP[141]. Sequences were obtained from the National Center for Biotechnology Information (NCBI) using the following accession numbers: J6 ADV40003.1, H77 ACA53555.1, J8 P26661.3, S52 AEB71616.2, ED43 AEB71617.2, SA13 AEB71618.2, HK6a AEB71619.2, QC69 ACM69041.1. The E2 sequences were aligned with multiple alignment using fast Fourier transform (MAFFT)[143] and edited for figure generation using JalView version 2[143] (ref 43).

BIBLIOGRAPHY

101-Lavanchy, D Evolving epidemiology of hepatitis C virus. *Clin. Micliobiol Infect.* 17, 107-115 (2011).

102. Pileri, P. et al. Bindin g of hepatitis C virus to CD81 *Science* 282, 938-941 (1998).

103. Scarselli, E. et al. The human scavenger receptor class B type I is a novel candidate receptor for the hepatitis C virus. *EMBO J.* 21, 5017-5025 (2002).

104. Sautto, G., Tarr, A. W., Mancini, N. & Clementi M Structural and antigenic definition of hepatitis C virus E2 glycoprotein epitopes targeted by monoclonal antibodies. *Clin. Dev. Immunol.* 2013, 450963 (2013).

105. Michalak, J. P. e al. Characterization of truncated forms of hepatitis C virus glycoproteins. *J. Gen. Virol.* 78-2299-2306(1997).

106. Drummer, H. E. & Poumbourios, P. Hepatitis C virus glycoprotein E2 contains a membrane-proximal heptad repeat sequence that is essential for E1E2 glycoprotein heterodimerization and viral entry. *J. Biol. Chem.* 279, 30066-30072 (2004).

107. Wahid, A. & Dubuisson, J. Virus-neuralizing antibodies to hepatitis C virus. *J. Viral Hepat.* 20, 369-376 (2013).

108. Keck, Z. Y. et al. Human monoclonal antibodies to a novel cluster of conformational epitopes on HCV E2 with resistance to neutralization escape in a genotype 2a isolate. *PLoS Pathog.* 8, e1002653 (2012).

109. Kong, L. et al. Structure of hepatitis C virus envelope glycoprotein E2 antigenic site 412 to 423 in complex with antibody AP33. *J. Virol.* 86, 13085-13088 (2012)

110. Kong, L. et al. Structural basis of hepatitis C virus neutralization by broadly neutralizing antibody HCV1. *Proc. Natl Acad. Sci. USA* 109, 9499-9504 (2012).

111. Deng, L. et al. Structural evidence for a bifurcated mode of action in the antibody-mediated neutralization of h epatitis C virus. *Proc. Natl Acad. Sci. USA* 110, 7418-7422 (2013).

112. Whidby, J. et al. Blocking hepatitis C virus infection with recombinant form of envelope protein 2 ectodomain. *J. Virol.* 83, 11078-11089 (2009).

113. Krey, T. et al. The disulfide bonds in glycoprotein E2 of hepatitis C virus reveal the tertiary organization of the molecule. *PLoS Pathog.* 6, e1000762 (2010).

114. Keck, Z. Y. et al. Analysis of a highly flexible conformational immunogenic domain A in hepatitis C virus E2. *J. Virol.* 79, 13199-13208 (2005).

115. Rothwangl, K. B., Manicassamy, B., Uprichard, S. L. & Rong, L. Dissecting the role of putative CD81 binding regions of E2 in mediating HCV entry: putative CD81 binding region 1 is not involved in CD81 binding *Virol. J.* 5, 46 (2008).

116. Lindenbach B. D., Thiel, H.-J. & Rice, C. M. in *Fields Virology* (eds Knipe, D. M. & Howley, P. M.) 1101-1152 (Lippincott Williams & Wilkins, 2007).

117. White J. M., Delos, S. E., Brecher M. & Schornberg, K. Structures and mechanisms of viral membrane fusion proteins: multiple variations common theme. *Crit. Rev. Biochem. Mol. Biol.* 43, 189-219 (2008).

118. Vaney, M. C. & Rey, F. A. Class II enveloped viruses. *Cell. Microbiol.* 13, 1451-1459 (2011).

119. El Omani, K., Iourin, O., Harlos, K., Grimes, J. M. & Stuart, D. I. Structure of a pestivirus envelope glycoprotein E2 clarifies its role in cell entry. *Cell reports* 3, 30-35 (2013).

120. Li, Y., Wang, J., Kanai, R. & Modis, Y. Crystal structure of glycoprotein E2 from bovine viral diarrhea virus. *Proc Natl Acad Sci USA* 110, 6805-6810 (2013).

121. Forns, X. et al. Hepatitis C virus lacking the hypervariable region 1 of the second envelope protein is infectious and causes acute resolving or persistent infection in chimpanzees. *Proc Natl Acad Sci USA* 97, 13318-13323 (2000).

122. Helle, F. et al. Role of N-linked glycans in the functions of hepatitis C virus envelope proteins incorporated into infectious virions. *J. Virol.* 84, 11905-11915 (2010).

123. Lavillette, D. et al. Characterization of fusion determinants points to the involvement of three discrete regions of both E1 and E2 glycoproteins in the membrane fusion process of hepatitis C virus. *J. Virol.* 81, 8752-8765 (2007).

124. Li, H. F., Huang, C. H., Ai, L. S., Chuang, C. K. & Chen, S. S. Mutagenesis of the fusion peptide-like domain of hepatitis C virus E1 glycoprotein: involvement in cell fusion and virus entry. *J. Biomed. Sci.* 16, 89 (2009).

125. Holm, L. & Rosenstrom, P. Dali server: conservation mapping n 3D. *Nucleic Acids Res.* 38, W545-W549 (2010).

126. Kong, L. et al, Hepatitis C virus E2 envelope glycoprotem core structure. *Science* 342, 1090-1094 (2013).

127. Reeves P. J., N Contreras R. & Khorana H. G Structure and function in rhodopsin: high-level expression of rhodopsin with restricted and homogeneous N-glycosylation by a tetracycline-inducible N-acetylglucosammyltransferase I-negative HEK293S stable mammalian cell line. *Proc. Natl Acad. Sci. USA* 99, 13419-13424 (2002).

128. Nielsen, S. S., Moller, M. & Gillilan, R. E. High-throughput biological small-angle X-ray scattering with a robotically loaded capillary cell. *J. Appl. Crystallogr.* 45, 213-223 (2012).

129. Petoukhov, M. V. et al. New developments in the ATSAS program package for small-angle scattering data analysis. *J. Appl. Crystallogr,* 45, 342-350 (2012).

130. Adams, P. D. et al, PHENIX: a comprehensive Python-based system for macromolecular structure solution. *Acta Crystallogr. D* 66, 213-221 (2010).

131. Emsley, P., Lohkamp, B., Scott, W. G. & Cowtan, K. Features and development of Coot. *Acta Crystallogr. D* 66, 486-501 (2010).

132. Murshudov, G. N. et al. REFMAC5 for the refinement of macromolecular crystal structures. *Acta Crystallogr. D* 67, 355-367 (2011).

133. Zhang, K. Y., Cowtan, K. & Main, P. Combining constraints for electron-density modification. *Methods Enzymol.* 277, 53-64 (1997).
134. Semenyuk, A. V. & Svergun, D. I. GNOM—a program package for small-angle scattering data processing. *J. Appl. Crystallogr.* 24, 537-540 (1991).
135. Svergun, D. I. Restoring low resolution structure of biological macromolecules from solution scattering using simulated annealing. *Biophys. J.* 76, 2879-2886 (1999).
136. Volkov, V. V. & Svergun, D. I. Uniqueness of ab initio shape determination in small-angle scattering. *J. Appl. Crystallogr.* 36, 860-864 (2003).
137. Kozin, M. B. & Svergun, D. Automated matching of high- and low-resolution structural models. *J. Appl. Crystallogr.* 34, 33-41 (2001).
138. Sharma, S. et al. Construct optimization for protein NMR structure analysis using amide hydrogen/deuterium exchange mass spectrometry. *Proteins* 76, 882-894 (2009).
139. Tiller, T., Busse, C. E. & Wardemann, H. Cloning and expression of murine Ig genes from single B cells. *J. Immunol. Methods* 350, 183-193 (2009).
140. Mateu, G., Donis R. O. Wakita, T., Bah, J. & Grakoui, A. Intragenotypic JFH1 based recombinant hepatitis C virus produces high levels of infectious particles but causes increased cell death. *Virology* 376, 397-407 (2008).
141. Kabsch, W. & Sander, C. Dictionary of protein secondary structure: pattern recognition of hydrogen-bonded and geometrical features. *Biopolymers* 22, 2577-2637 (1983).
142. Katoh, K., Kuma, K., Toh, H. & Miyata, T. MAFFT version 5: improvement in accuracy of multiple sequence alignment. *Nucleic Acids Res.* 33, 511-518 (2005).
143. Waterhouse, A. M., Procter, J. B., Martin, D. M., Clamp, M. & Barton, G. J. Jalview Version 2-a multiple sequence alignment editor and analysis workbench. *Bioinformatics* 25, 1189-1191 (2009).
144. Abdul Ghafoor Khan, Jillian Whidby, Matthew T. Miller, Hannah Scarborough, Alexandra V. Zatorski, Alicja Cygan, Aryn A. Price, Samantha A. Yost, Caitlin D. Bohannon, Joshy Jacob, Arash Grakoui & Joseph Marcotrigiano, Structure of the core ectodomain of the hepatitis C virus envelope glycoprotein 2, doi:10.1038/nature13117 (2014).

The disclosures of all references cited herein are hereby incorporated by reference in their entireties.

Other modifications and variations of the specific embodiments of the invention as set forth herein will be apparent to those skilled in the art.

What is claimed is:

1. A method of producing a Hepatitis C virus (HCV) eE2 polypeptide comprising:
   (i) providing a construct comprising:
      a cytomegalovirus (CMV) promoter,
      a prolactin signal sequence,
      a nucleic acid sequence encoding an amino acid sequence of an ectodomain of a HCV E2 (HCV eE2) polypeptide,
      a thrombin cleavage site,
      wherein the CMV promoter is followed by the prolactin signal sequence, the prolactin signal sequence is followed by the nucleic acid sequence, the nucleic acid sequence is followed by the thrombin cleavage site, and the amino acid sequence is identical to the amino acid sequence consisting of amino acids 384-656 of SEQ ID NO:1 of HCV 2a genotype, isolate J6, or the corresponding sequence of a different HCV genotype or the corresponding sequence of SEQ ID NO: 15, SEQ ID NO: 16, SEQ ID NO: 17, SEQ ID NO: 18, SEQ

SEQUENCE LISTING

<160> NUMBER OF SEQ ID NOS: 21

<210> SEQ ID NO 1
<211> LENGTH: 281
<212> TYPE: PRT
<213> ORGANISM: Hepatitis C virus

<400> SEQUENCE: 1

```
Arg Thr His Thr Val Gly Gly Ser Ala Ala Gln Thr Thr Gly Arg Leu
1               5                   10                  15

Thr Ser Leu Phe Asp Met Gly Pro Arg Gln Lys Ile Gln Leu Val Asn
            20                  25                  30

Thr Asn Gly Ser Trp His Ile Asn Arg Thr Ala Leu Asn Cys Asn Asp
        35                  40                  45

Ser Leu His Thr Gly Phe Ile Ala Ser Leu Phe Tyr Thr His Ser Phe
    50                  55                  60

Asn Ser Ser Gly Cys Pro Glu Arg Met Ser Ala Cys Arg Ser Ile Glu
65                  70                  75                  80

Ala Phe Arg Val Gly Trp Gly Ala Leu Gln Tyr Glu Asp Asn Val Thr
                85                  90                  95

Asn Pro Glu Asp Met Arg Pro Tyr Cys Trp His Tyr Pro Pro Arg Gln
            100                 105                 110

Cys Gly Val Val Ser Ala Lys Thr Val Cys Gly Pro Val Tyr Cys Phe
        115                 120                 125

Thr Pro Ser Pro Val Val Val Gly Thr Thr Asp Arg Leu Gly Ala Pro
    130                 135                 140

Thr Tyr Thr Trp Gly Glu Asn Glu Thr Asp Val Phe Leu Leu Asn Ser
145                 150                 155                 160

Thr Arg Pro Pro Leu Gly Ser Trp Phe Gly Cys Thr Trp Met Asn Ser
                165                 170                 175

Ser Gly Tyr Thr Lys Thr Cys Gly Ala Pro Pro Cys Arg Thr Arg Ala
            180                 185                 190

Asp Phe Asn Ala Ser Thr Asp Leu Leu Cys Pro Thr Asp Cys Phe Arg
```

```
                195                 200                 205
Lys His Pro Asp Thr Thr Tyr Leu Lys Cys Gly Ser Gly Pro Trp Leu
        210                 215                 220

Thr Pro Arg Cys Leu Ile Asp Tyr Pro Tyr Arg Leu Trp His Tyr Pro
225                 230                 235                 240

Cys Thr Val Asn Tyr Thr Ile Phe Lys Ile Arg Met Tyr Val Gly Gly
                245                 250                 255

Val Glu His Arg Leu Thr Ala Ala Cys Asn Phe Thr Arg Gly Asp Arg
            260                 265                 270

Cys Asn Leu Glu Asp Arg Asp Arg Ser
                275                 280

<210> SEQ ID NO 2
<211> LENGTH: 17
<212> TYPE: PRT
<213> ORGANISM: Hepatitis C virus

<400> SEQUENCE: 2

Asp Met Gly Pro Arg Gln Lys Ile Gln Leu Val Asn Thr Asn Gly Ser
1               5                   10                  15

Trp

<210> SEQ ID NO 3
<211> LENGTH: 17
<212> TYPE: PRT
<213> ORGANISM: Hepatitis C virus

<400> SEQUENCE: 3

His Ile Asn Arg Thr Ala Leu Asn Cys Asn Asp Ser Leu His Thr Gly
1               5                   10                  15

Phe

<210> SEQ ID NO 4
<211> LENGTH: 14
<212> TYPE: PRT
<213> ORGANISM: Hepatitis C virus

<400> SEQUENCE: 4

Tyr Thr His Ser Phe Asn Ser Ser Gly Cys Pro Glu Arg Met
1               5                   10

<210> SEQ ID NO 5
<211> LENGTH: 18
<212> TYPE: PRT
<213> ORGANISM: Hepatitis C virus

<400> SEQUENCE: 5

Gly Ala Leu Gln Tyr Glu Asp Asn Val Thr Asn Pro Glu Asp Met Arg
1               5                   10                  15

Pro Tyr

<210> SEQ ID NO 6
<211> LENGTH: 15
<212> TYPE: PRT
<213> ORGANISM: Hepatitis C virus

<400> SEQUENCE: 6

Asp Arg Leu Gly Ala Pro Thr Tyr Thr Trp Gly Glu Asn Glu Thr
1               5                   10                  15
```

```
<210> SEQ ID NO 7
<211> LENGTH: 13
<212> TYPE: PRT
<213> ORGANISM: Hepatitis C virus

<400> SEQUENCE: 7

Leu Leu Asn Ser Thr Arg Pro Pro Leu Gly Ser Trp Phe
1               5                   10

<210> SEQ ID NO 8
<211> LENGTH: 11
<212> TYPE: PRT
<213> ORGANISM: Hepatitis C virus

<400> SEQUENCE: 8

Phe Gly Cys Thr Trp Met Asn Ser Ser Gly Tyr
1               5                   10

<210> SEQ ID NO 9
<211> LENGTH: 28
<212> TYPE: PRT
<213> ORGANISM: Hepatitis C virus

<400> SEQUENCE: 9

Thr Lys Thr Cys Gly Ala Pro Pro Cys Arg Thr Arg Ala Asp Phe Asn
1               5                   10                  15

Ala Ser Thr Asp Leu Leu Cys Pro Thr Asp Cys Phe
            20                  25

<210> SEQ ID NO 10
<211> LENGTH: 8
<212> TYPE: PRT
<213> ORGANISM: Hepatitis C virus

<400> SEQUENCE: 10

His Tyr Pro Cys Thr Val Asn Tyr
1               5

<210> SEQ ID NO 11
<211> LENGTH: 14
<212> TYPE: PRT
<213> ORGANISM: Hepatitis C virus

<400> SEQUENCE: 11

Val Gly Gly Val Glu His Arg Leu Thr Ala Ala Cys Asn Phe
1               5                   10

<210> SEQ ID NO 12
<211> LENGTH: 7
<212> TYPE: PRT
<213> ORGANISM: Hepatitis C virus

<400> SEQUENCE: 12

Asn Leu Glu Asp Arg Asp Arg
1               5

<210> SEQ ID NO 13
<211> LENGTH: 6
<212> TYPE: PRT
<213> ORGANISM: Hepatitis C virus

<400> SEQUENCE: 13

Arg Ser Ile Glu Ala Phe
1               5
```

<210> SEQ ID NO 14
<211> LENGTH: 281
<212> TYPE: PRT
<213> ORGANISM: Hepatitis C virus

<400> SEQUENCE: 14

Arg Thr His Thr Val Gly Gly Ser Ala Ala Gln Thr Gly Arg Leu
1               5                   10                  15

Thr Ser Leu Phe Asp Met Gly Pro Arg Gln Lys Ile Gln Leu Val Asn
            20                  25                  30

Thr Asn Gly Ser Trp His Ile Asn Arg Thr Ala Leu Asn Cys Asn Asp
        35                  40                  45

Ser Leu His Thr Gly Phe Ile Ala Ser Leu Phe Tyr Thr His Ser Phe
    50                  55                  60

Asn Ser Ser Gly Cys Pro Glu Arg Met Ser Ala Cys Arg Ser Ile Glu
65                  70                  75                  80

Ala Phe Arg Val Gly Trp Gly Ala Leu Gln Tyr Glu Asp Asn Val Thr
                85                  90                  95

Asn Pro Glu Asp Met Arg Pro Tyr Cys Trp His Tyr Pro Pro Arg Gln
            100                 105                 110

Cys Gly Val Val Ser Ala Lys Thr Val Cys Gly Pro Val Tyr Cys Phe
        115                 120                 125

Thr Pro Ser Pro Val Val Gly Thr Thr Asp Arg Leu Gly Ala Pro
    130                 135                 140

Thr Tyr Thr Trp Gly Glu Asn Glu Thr Asp Val Phe Leu Leu Asn Ser
145                 150                 155                 160

Thr Arg Pro Pro Leu Gly Ser Trp Phe Gly Cys Thr Trp Met Asn Ser
                165                 170                 175

Ser Gly Tyr Thr Lys Thr Cys Gly Ala Pro Pro Cys Arg Thr Arg Ala
            180                 185                 190

Asp Phe Asn Ala Ser Thr Asp Leu Leu Cys Pro Thr Asp Cys Phe Arg
        195                 200                 205

Lys His Pro Asp Thr Thr Tyr Leu Lys Cys Gly Ser Gly Pro Trp Leu
    210                 215                 220

Thr Pro Arg Cys Leu Ile Asp Tyr Pro Tyr Arg Leu Trp His Tyr Pro
225                 230                 235                 240

Cys Thr Val Asn Tyr Thr Ile Phe Lys Ile Arg Met Tyr Val Gly Gly
                245                 250                 255

Val Glu His Arg Leu Thr Ala Ala Cys Asn Phe Thr Arg Gly Asp Arg
            260                 265                 270

Cys Asn Leu Glu Asp Arg Asp Arg Ser
        275                 280

<210> SEQ ID NO 15
<211> LENGTH: 277
<212> TYPE: PRT
<213> ORGANISM: Hepatitis C virus

<400> SEQUENCE: 15

Glu Thr His Val Thr Gly Gly Ser Ala Gly Arg Thr Ala Gly Leu
1               5                   10                  15

Val Gly Leu Leu Thr Pro Gly Ala Lys Gln Asn Ile Gln Leu Ile Asn
            20                  25                  30

Thr Asn Gly Ser Trp His Ile Asn Ser Thr Ala Leu Asn Cys Asn Glu
        35                  40                  45

```
Ser Leu Asn Thr Gly Trp Leu Ala Gly Leu Phe Tyr Gln His Lys Phe
 50                  55                  60

Asn Ser Ser Gly Cys Pro Glu Arg Leu Ala Ser Cys Arg Arg Leu Thr
 65                  70                  75                  80

Asp Phe Ala Gln Gly Trp Gly Pro Ile Ser Tyr Ala Asn Gly Ser Gly
                 85                  90                  95

Leu Asp Glu Arg Pro Tyr Cys Trp His Tyr Pro Arg Pro Cys Gly
            100                 105                 110

Ile Val Pro Ala Lys Ser Val Cys Gly Pro Val Tyr Cys Phe Thr Pro
            115                 120                 125

Ser Pro Val Val Gly Thr Thr Asp Arg Ser Gly Ala Pro Thr Tyr
135                 135                 140

Ser Trp Gly Ala Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
                165                 170                 175

Phe Thr Lys Val Cys Gly Ala Pro Pro Cys Val Ile Gly Gly Val Gly
            180                 185                 190

Asn Asn Thr Leu Leu Cys Pro Thr Asp Cys Phe Arg Lys His Pro Glu
            195                 200                 205

Ala Thr Tyr Ser Arg Cys Gly Ser Gly Pro Trp Ile Thr Pro Arg Cys
210                 215                 220

Met Val Asp Tyr Pro Tyr Arg Leu Trp His Tyr Pro Cys Thr Ile Asn
225                 230                 235                 240

Tyr Thr Ile Phe Lys Val Arg Met Tyr Val Gly Gly Val Glu His Arg
                245                 250                 255

Leu Glu Ala Ala Cys Asn Trp Thr Arg Gly Glu Arg Cys Asp Leu Glu
            260                 265                 270

Asp Arg Asp Arg Ser
            275

<210> SEQ ID NO 16
<211> LENGTH: 281
<212> TYPE: PRT
<213> ORGANISM: Hepatitis C virus

<400> SEQUENCE: 16

Thr Thr Tyr Ser Ser Gly Gln Glu Ala Gly Arg Thr Val Ala Gly Phe
 1               5                  10                  15

Ala Gly Leu Phe Thr Thr Gly Ala Lys Gln Asn Leu Tyr Leu Ile Asn
                 20                  25                  30

Thr Asn Gly Ser Trp His Ile Asn Arg Thr Ala Leu Asn Cys Asn Asp
             35                  40                  45

Ser Leu Gln Thr Gly Phe Leu Ala Ser Leu Phe Tyr Thr His Lys Phe
 50                  55                  60

Asn Ser Ser Gly Cys Pro Glu Arg Leu Ser Ser Cys Arg Gly Leu Asp
 65                  70                  75                  80

Asp Phe Arg Ile Gly Trp Gly Thr Leu Glu Tyr Glu Thr Asn Val Thr
                 85                  90                  95

Asn Asp Gly Asp Met Arg Pro Tyr Cys Trp His Tyr Pro Pro Arg Pro
            100                 105                 110

Cys Gly Ile Val Pro Ala Arg Thr Val Cys Gly Pro Val Tyr Cys Phe
            115                 120                 125

Thr Pro Ser Pro Val Val Gly Thr Thr Asp Lys Gln Gly Val Pro
130                 135                 140
```

```
Thr Tyr Thr Trp Gly Glu Asn Glu Thr Asp Val Phe Leu Leu Asn Ser
145                 150                 155                 160

Thr Arg Pro Pro Arg Gly Ala Trp Phe Gly Cys Thr Trp Met Asn Gly
                165                 170                 175

Thr Gly Phe Thr Lys Thr Cys Gly Ala Pro Pro Cys Arg Ile Arg Lys
            180                 185                 190

Asp Tyr Asn Ser Thr Ile Asp Leu Leu Cys Pro Thr Asp Cys Phe Arg
            195                 200                 205

Lys His Pro Asp Ala Thr Tyr Leu Lys Cys Gly Ala Gly Pro Trp Leu
        210                 215                 220

Thr Pro Arg Cys Leu Val Asp Tyr Pro Tyr Arg Leu Trp His Tyr Pro
225                 230                 235                 240

Cys Thr Val Asn Phe Thr Ile Phe Lys Ala Arg Met Tyr Val Gly Gly
                245                 250                 255

Val Glu His Arg Phe Ser Ala Ala Cys Asn Phe Thr Arg Gly Asp Arg
                260                 265                 270

Cys Arg Leu Glu Asp Arg Asp Arg Gly
            275                 280

<210> SEQ ID NO 17
<211> LENGTH: 283
<212> TYPE: PRT
<213> ORGANISM: Hepatitis C virus

<400> SEQUENCE: 17

Glu Thr Tyr Val Thr Gly Gly Ser Val Ala His Ser Ala Arg Gly Leu
1               5                   10                  15

Thr Ser Leu Phe Ser Met Gly Ala Lys Gln Lys Leu Gln Leu Val Asn
                20                  25                  30

Thr Asn Gly Ser Trp His Ile Asn Ser Thr Ala Leu Asn Cys Asn Glu
            35                  40                  45

Ser Ile Asn Thr Gly Phe Ile Ala Gly Leu Phe Tyr Tyr His Lys Phe
50                  55                  60

Asn Ser Thr Gly Cys Pro Gln Arg Leu Ser Ser Cys Lys Pro Ile Ile
65                  70                  75                  80

Ser Phe Arg Gln Gly Trp Gly Pro Leu Thr Asp Ala Asn Ile Thr Gly
                85                  90                  95

Pro Ser Asp Asp Arg Pro Tyr Cys Trp His Tyr Ala Pro Arg Pro Cys
            100                 105                 110

Ser Val Val Pro Ala Ser Ser Val Cys Gly Pro Val Tyr Cys Phe Thr
            115                 120                 125

Pro Ser Pro Val Val Val Gly Thr Thr Asp Ile Lys Gly Lys Pro Thr
        130                 135                 140

Tyr Asn Trp Gly Glu Asn Glu Thr Asp Val Phe Leu Leu Glu Ser Leu
145                 150                 155                 160

Arg Pro Pro Ser Gly Arg Trp Phe Gly Cys Ala Trp Met Asn Ser Thr
                165                 170                 175

Gly Phe Leu Lys Thr Cys Gly Ala Pro Pro Cys Asn Ile Tyr Gly Gly
            180                 185                 190

Glu Gly Asp Pro Glu Asn Glu Thr Asp Leu Phe Cys Pro Thr Asp Cys
            195                 200                 205

Phe Arg Lys His Pro Glu Ala Thr Tyr Ser Arg Cys Gly Ala Gly Pro
        210                 215                 220

Trp Leu Thr Pro Arg Cys Met Val Asp Tyr Pro Tyr Arg Leu Trp His
```

```
                225                 230                 235                 240
Tyr Pro Cys Thr Val Asn Phe Thr Leu Phe Lys Val Arg Met Phe Val
                    245                 250                 255

Gly Gly Phe Glu His Arg Phe Thr Ala Ala Cys Asn Trp Thr Arg Gly
                260                 265                 270

Glu Arg Cys Asn Ile Glu Asp Arg Asp Arg Ser
                275                 280

<210> SEQ ID NO 18
<211> LENGTH: 277
<212> TYPE: PRT
<213> ORGANISM: Hepatitis C virus

<400> SEQUENCE: 18

Glu Thr His Val Ser Gly Ala Ala Val Gly Arg Ser Thr Ala Gly Leu
1               5                   10                  15

Ala Asn Leu Phe Ser Ser Gly Ser Lys Gln Asn Leu Gln Leu Ile Asn
                20                  25                  30

Ser Asn Gly Ser Trp His Ile Asn Arg Thr Ala Leu Asn Cys Asn Asp
            35                  40                  45

Ser Leu Asn Thr Gly Phe Leu Ala Ser Leu Phe Tyr Thr His Lys Phe
        50                  55                  60

Asn Ser Ser Gly Cys Ser Glu Arg Leu Ala Cys Cys Lys Ser Leu Asp
65                  70                  75                  80

Ser Tyr Gly Gln Gly Trp Gly Pro Leu Gly Val Ala Asn Ile Ser Gly
                85                  90                  95

Ser Ser Asp Asp Arg Pro Tyr Cys Trp His Tyr Ala Pro Arg Pro Cys
                100                 105                 110

Gly Ile Val Pro Ala Ser Ser Val Cys Gly Pro Val Tyr Cys Phe Thr
            115                 120                 125

Pro Ser Pro Val Val Val Gly Thr Thr Asp His Val Gly Val Pro Thr
        130                 135                 140

Tyr Thr Trp Gly Glu Asn Glu Thr Asp Val Phe Leu Leu Asn Ser Thr
145                 150                 155                 160

Arg Pro Pro His Gly Ala Trp Phe Gly Cys Val Trp Met Asn Ser Thr
                165                 170                 175

Gly Phe Thr Lys Thr Cys Gly Ala Pro Pro Cys Glu Val Asn Thr Asn
                180                 185                 190

Asn Gly Thr Trp His Cys Pro Thr Asp Cys Phe Arg Lys His Pro Glu
            195                 200                 205

Thr Thr Tyr Ala Lys Cys Gly Ser Gly Pro Trp Ile Thr Pro Arg Cys
        210                 215                 220

Leu Ile Asp Tyr Pro Tyr Arg Leu Trp His Phe Pro Cys Thr Ala Asn
225                 230                 235                 240

Phe Ser Val Phe Asn Ile Arg Thr Phe Val Gly Gly Ile Glu His Arg
                245                 250                 255

Met Gln Ala Ala Cys Asn Trp Thr Arg Gly Glu Val Cys Gly Leu Glu
                260                 265                 270

His Arg Asp Arg Val
        275

<210> SEQ ID NO 19
<211> LENGTH: 278
<212> TYPE: PRT
<213> ORGANISM: Hepatitis C virus
```

<400> SEQUENCE: 19

Ser Thr Arg Thr Val Gly Gly Ser Ala Ala Gln Gly Ala Arg Gly Leu
1               5                   10                  15

Ala Ser Leu Phe Thr Pro Gly Pro Gln Gln Asn Leu Gln Leu Ile Asn
                20                  25                  30

Thr Asn Gly Ser Trp His Ile Asn Arg Thr Ala Leu Asn Cys Asn Asp
            35                  40                  45

Ser Leu Gln Thr Gly Phe Val Ala Gly Leu Leu Tyr Tyr His Lys Phe
        50                  55                  60

Asn Ser Thr Gly Cys Pro Gln Arg Met Ala Ser Cys Arg Pro Leu Ala
65                  70                  75                  80

Ala Phe Asp Gln Gly Trp Gly Thr Ile Ser Tyr Ala Ala Val Ser Gly
                85                  90                  95

Pro Ser Asp Asp Lys Pro Tyr Cys Trp His Tyr Pro Arg Pro Cys
            100                 105                 110

Gly Ile Val Pro Ala Arg Gly Val Cys Gly Pro Val Tyr Cys Phe Thr
            115                 120                 125

Pro Ser Pro Val Val Gly Thr Thr Asp Arg Lys Gly Asn Pro Thr
        130                 135                 140

Tyr Ser Trp Gly Glu Asn Glu Thr Asp Ile Phe Leu Leu Asn Asn Thr
145                 150                 155                 160

Arg Pro Pro Thr Gly Asn Trp Phe Gly Cys Thr Trp Met Asn Ser Thr
                165                 170                 175

Gly Phe Val Lys Thr Cys Gly Ala Pro Pro Cys Asn Leu Gly Pro Thr
            180                 185                 190

Gly Asn Asn Ser Leu Lys Cys Pro Thr Asp Cys Phe Arg Lys His Pro
        195                 200                 205

Asp Ala Thr Tyr Thr Lys Cys Gly Ser Gly Pro Trp Leu Thr Pro Arg
            210                 215                 220

Cys Leu Val His Tyr Pro Tyr Arg Leu Trp His Tyr Pro Cys Thr Leu
225                 230                 235                 240

Asn Tyr Thr Ile Phe Lys Val Arg Met Tyr Ile Gly Gly Leu Glu His
                245                 250                 255

Arg Leu Glu Val Ala Cys Asn Trp Thr Arg Gly Glu Arg Cys Asp Leu
            260                 265                 270

Glu Asp Arg Asp Arg Ala
        275

<210> SEQ ID NO 20
<211> LENGTH: 282
<212> TYPE: PRT
<213> ORGANISM: Hepatitis C virus

<400> SEQUENCE: 20

Thr Thr Thr Ile Gly His Gln Val Gly Arg Thr Thr Gly Gly Leu Ala
1               5                   10                  15

Ser Leu Phe Ser Ile Gly Pro Arg Gln Asn Leu Gln Leu Ile Asn Thr
                20                  25                  30

Thr Gly Ser Trp His Ile Asn Arg Thr Ala Leu Asn Cys Asn Asp Ser
            35                  40                  45

Leu Lys Thr Gly Phe Ile Thr Ser Leu Phe Tyr Ala Lys Asn Val Asn
        50                  55                  60

Ser Ser Gly Cys Pro Glu Arg Met Ala Ala Cys Lys Pro Leu Ala Asp
65                  70                  75                  80

```
Phe Arg Gln Gly Trp Gly Gln Ile Thr Tyr Lys Val Asn Ile Ser Gly
                85                  90                  95

Pro Ser Asp Asp Arg Pro Tyr Cys Trp His Tyr Ala Thr Arg Pro Cys
            100                 105                 110

Asp Val Val Ser Ala Arg Thr Val Cys Gly Pro Val Tyr Cys Phe Thr
        115                 120                 125

Pro Ser Pro Val Val Ile Gly Thr Thr Asp Lys Leu Gly Ile Pro Thr
    130                 135                 140

Tyr Asn Trp Gly Glu Asn Glu Thr Asp Val Phe Met Leu Glu Ser Leu
145                 150                 155                 160

Arg Pro Pro Thr Gly Gly Trp Phe Gly Cys Thr Trp Met Asn Ser Thr
                165                 170                 175

Gly Phe Thr Lys Thr Cys Gly Ala Pro Pro Cys Gln Ile Val Pro Gly
            180                 185                 190

Asp Tyr Asn Ser Ser Ala Asn Glu Leu Leu Cys Pro Thr Asp Cys Phe
        195                 200                 205

Arg Lys His Pro Glu Ala Thr Tyr Gln Arg Cys Gly Ser Gly Pro Trp
    210                 215                 220

Ile Thr Pro Arg Cys Leu Val Asp Tyr His Tyr Arg Leu Trp His Tyr
225                 230                 235                 240

Pro Cys Thr Val Asn Phe Thr Leu His Lys Val Arg Met Phe Val Gly
                245                 250                 255

Gly Ile Glu His Arg Phe Asp Ala Ala Cys Asn Trp Thr Arg Gly Glu
            260                 265                 270

Arg Cys Asp Leu His Asp Arg Asp Arg Ile
    275                 280

<210> SEQ ID NO 21
<211> LENGTH: 281
<212> TYPE: PRT
<213> ORGANISM: Hepatitis C virus

<400> SEQUENCE: 21

Glu Thr Met Ala Val Gly Ala Arg Ala Ala His Thr Thr Gly Ala Leu
1               5                   10                  15

Val Ser Leu Leu Asn Pro Gly Pro Ser Gln Arg Leu Gln Leu Ile Asn
                20                  25                  30

Thr Asn Gly Ser Trp His Ile Asn Arg Thr Ala Leu Asn Cys Asn Asp
            35                  40                  45

Ser Leu Gln Thr Gly Phe Ile Ala Ala Leu Phe Tyr Thr His Arg Phe
        50                  55                  60

Asn Ser Ser Gly Cys Pro Glu Arg Met Ala Ser Cys Lys Pro Leu Ser
65                  70                  75                  80

Asp Phe Asp Gln Gly Trp Gly Pro Leu Trp Tyr Asn Ser Thr Glu Arg
                85                  90                  95

Pro Ser Asp Gln Arg Pro Tyr Cys Trp His Tyr Ala Pro Ser Pro Cys
            100                 105                 110

Gly Ile Val Pro Ala Lys Asp Val Cys Gly Pro Val Tyr Cys Phe Thr
        115                 120                 125

Pro Ser Pro Val Val Val Gly Thr Thr Asp Arg Arg Gly Val Pro Thr
    130                 135                 140

Tyr Thr Trp Gly Glu Asn Glu Ser Asp Val Phe Leu Leu Asn Ser Thr
145                 150                 155                 160

Arg Pro Pro Gln Gly Ser Trp Phe Gly Cys Ser Trp Met Asn Thr Thr
                165                 170                 175
```

```
Gly Phe Thr Lys Thr Cys Gly Gly Pro Pro Cys Lys Ile Arg Pro Gln
            180             185             190

Gly Ala Gln Ser Asn Thr Ser Leu Thr Cys Pro Thr Asp Cys Phe Arg
            195             200             205

Lys His Pro Arg Ala Thr Tyr Ser Ala Cys Gly Ser Gly Pro Trp Leu
    210             215             220

Thr Pro Arg Cys Met Val His Tyr Pro Tyr Arg Leu Trp His Tyr Pro
225             230             235             240

Cys Thr Val Asn Phe Thr Ile His Lys Val Arg Leu Tyr Ile Gly Gly
                245             250             255

Val Glu His Arg Leu Asp Ala Ala Cys Asn Trp Thr Arg Gly Glu Arg
            260             265             270

Cys Asp Leu Glu Asp Arg Asp Arg Val
            275             280
```